US009717949B1

(12) United States Patent
Tran et al.

(10) Patent No.: US 9,717,949 B1
(45) Date of Patent: *Aug. 1, 2017

(54) SMART SPORT DEVICE

(71) Applicant: Bao Tran, Saratoga, CA (US)

(72) Inventors: Bao Tran, Saratoga, CA (US); Ha Tran, Saratoga, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/407,248

(22) Filed: Jan. 16, 2017

Related U.S. Application Data

(63) Continuation of application No. 15/144,773, filed on May 2, 2016, now Pat. No. 9,610,476.

(51) Int. Cl.
| | | |
|---|---|---|
| *A63B 71/00* | (2006.01) | |
| *A63B 24/00* | (2006.01) | |
| *A63B 60/46* | (2015.01) | |
| *A63B 69/36* | (2006.01) | |
| *A63B 69/38* | (2006.01) | |
| *H04L 29/08* | (2006.01) | |
| *H04B 1/04* | (2006.01) | |
| *H04W 88/02* | (2009.01) | |

(52) U.S. Cl.
CPC .......... *A63B 24/0006* (2013.01); *A63B 60/46* (2015.10); *A63B 69/36* (2013.01); *A63B 69/38* (2013.01); *A63B 2208/0204* (2013.01); *A63B 2220/40* (2013.01); *A63B 2220/53* (2013.01); *A63B 2220/803* (2013.01); *A63B 2220/833* (2013.01); *A63B 2230/06* (2013.01); *H04B 1/04* (2013.01); *H04L 67/10* (2013.01); *H04W 88/02* (2013.01)

(58) Field of Classification Search
USPC ...................................... 463/16–42
See application file for complete search history.

(56) References Cited

U.S. PATENT DOCUMENTS

| | | | |
|---|---|---|---|
| 4,904,132 A | 2/1990 | Popenoe | |
| 4,991,249 A | 2/1991 | Suroff | |
| 5,386,741 A | 2/1995 | Rennex | |
| 5,723,786 A | 3/1998 | Klapman | |
| 5,894,620 A | 4/1999 | Polaert | |
| 6,244,644 B1 | 6/2001 | Lovchik | |
| 6,536,068 B1 | 3/2003 | Yang | |
| 6,720,984 B1 * | 4/2004 | Jorgensen | G06F 3/015 600/300 |
| 7,001,270 B2 | 2/2006 | Taub | |
| 7,581,272 B2 | 9/2009 | Xie | |
| 8,174,934 B2 | 5/2012 | Li | |
| 8,390,700 B2 | 3/2013 | Yoshizaki | |
| 8,460,216 B2 | 6/2013 | Miller | |
| 8,540,468 B2 | 9/2013 | Mekid | |
| 8,572,764 B2 | 11/2013 | Thellmann | |
| 8,715,096 B2 | 5/2014 | Cherbini | |
| 8,747,336 B2 | 6/2014 | Tran | |
| 8,974,734 B2 | 3/2015 | Tian | |
| 9,212,933 B2 | 12/2015 | Jetcheva | |
| 2002/0065121 A1 * | 5/2002 | Fukunaga | A63F 13/08 463/8 |

(Continued)

FOREIGN PATENT DOCUMENTS

WO  WO/2015/073062  5/2015

*Primary Examiner* — Masud Ahmed
(74) *Attorney, Agent, or Firm* — Tran & Associates

(57) ABSTRACT

An Internet of Thing (IoT) sport device includes a body with a processor, a camera and a wireless transceiver coupled to the processor.

20 Claims, 15 Drawing Sheets

(56) References Cited

U.S. PATENT DOCUMENTS

| | | | |
|---|---|---|---|
| 2006/0160616 A1* | 7/2006 | Kato | A63F 13/10 463/30 |
| 2006/0166737 A1* | 7/2006 | Bentley | A61B 5/1122 463/30 |
| 2012/0269494 A1 | 10/2012 | Satyanarayana | |
| 2013/0066448 A1* | 3/2013 | Alonso | H04Q 9/00 700/91 |
| 2014/0072278 A1* | 3/2014 | Kramer | H04N 5/23296 386/240 |
| 2014/0073481 A1* | 3/2014 | Aibara | A63B 24/0084 482/1 |
| 2014/0206481 A1 | 7/2014 | Zuger | |
| 2015/0201694 A1 | 7/2015 | Boyce | |
| 2015/0279366 A1 | 10/2015 | Krestnikov | |
| 2015/0283450 A1 | 10/2015 | Mcroberts | |
| 2015/0319829 A1 | 11/2015 | Shu | |
| 2016/0055422 A1 | 2/2016 | Li | |
| 2016/0077593 A1* | 3/2016 | Zuger | G06F 1/163 345/173 |
| 2016/0098860 A1 | 4/2016 | Basra | |

* cited by examiner

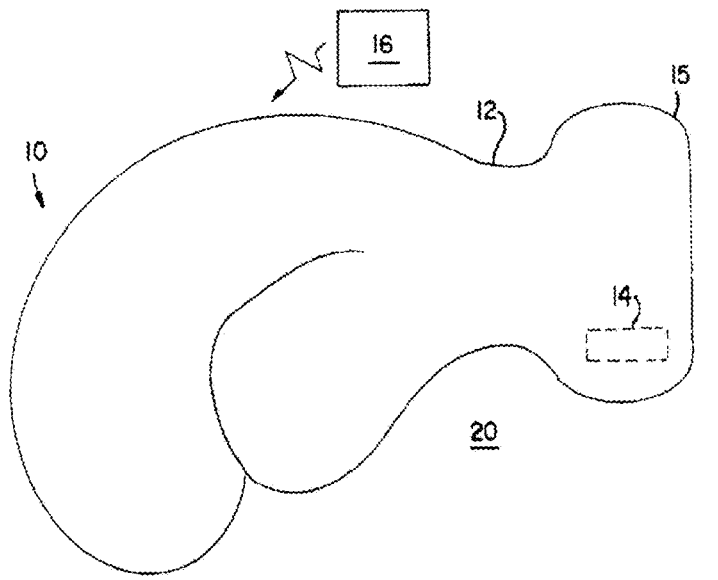
FIG. 7
FIG. 8
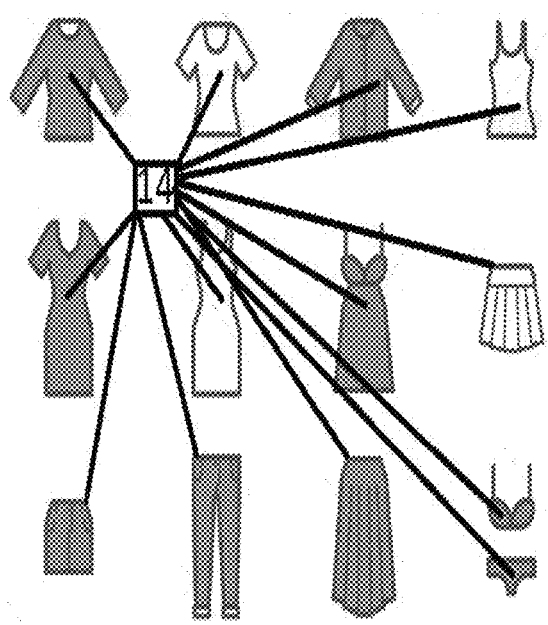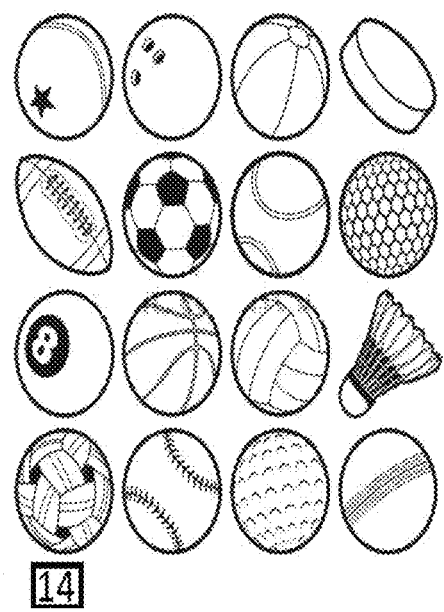
FIG. 9
FIG. 10

US 9,717,949 B1

SMART SPORT DEVICE

BACKGROUND

The present invention relates to the Internet of Things (IoT).

The world's top sports include the following. Soccer is the biggest global sport and a top 10 sport in all countries measured, as well as the dominant sport in South America, Europe and Africa. The world cup final is watched by an estimated 600 million people and the annual final by more than 300 million. Basketball is a massive sport in US and China, as well as major across continental Europe and South America, making it one of the biggest global sports. Tennis is probably the world's most universal sport being in the top 7 sports in every single country measured and a major sport of interest in Asia, Europe, Australasia, Latin and North America, thus making it 3rd in world's biggest sports. Cricket dominates sports media coverage for around a quarter of the world's population in the Indian sub-continent. Also huge in UK, Australia and South Africa. 2011 world cup final watched by more than 400 million globally and semi-final between Pakistan and India by reported 1 billion. Baseball is a huge sport in 2 economic powerhouses of US and Japan, being the biggest sport in the latter. American Football is the biggest sport in the US, with popularity fueled by the US domestic market, where the Superbowl is regularly the most watched annual event. Car racing is a major sport in Europe and US. Golf is a major sport in US, Japan, Korea, and UK. Ice Hockey is the biggest sport in Canada, Russia, and the US, making it the biggest winter sport. Other popular sports include boxing, badminton, volleyball, cycling, swimming, snooker, martial arts, rugby, motorbike, hockey, table tennis, horse racing, gymnastics, handball, figure skating, wrestling, skiing, diving, skating, archery, sailing, wrestling, fencing, equestrian, rowing, surfing, Beach Volleyball, Pool/Billiards, Lacrosse, Windsurfing, Polo, Tenpin Bowling, Racquetball, Competitive Climbing, Mountain Biking, among others.

In various sports such a baseball, tennis and golf, proper stroke is key to success. Swing fluidity alongside improved movement, balance, and precise positioning at the proper distance to each ball is important in tennis. Correspondingly, one of the most difficult decisions a golfer must make when playing golf is the selection of one of their golf clubs to use for each stroke during a golf game. This decision is repeatedly made for each stroke in view of the relatively large number of golf clubs that are used to play golf. The impact of each different golf club against the golf ball will result in a different carrying distance of the golf ball and therefore it is extremely important for a golfer to select the most suitable golf club to use for each shot. Moreover, each golf club is often used in one of several possible clock or swing positions. The carrying distance of the golf ball when struck by the same golf club will vary as a function of the swing position. It is therefore important for the golfer to select not only the most suitable golf club to use for each shot, but also the swing position in which to use the selected golf club.

SUMMARY

In one aspect, an Internet of Thing (IoT) device for sport deviceing includes thistles, a light source; sensors including a camera; a processor coupled to the light source and the sensor; and a wireless transceiver coupled to the processor.

These and other features of the present invention will become readily apparent upon further review of the following specification and drawings.

BRIEF DESCRIPTION OF THE DRAWINGS

FIG. 7 shows an exemplary glove,

FIG. 8 shows an exemplary smart band,

FIG. 9 shows exemplary smart clothing,

FIG. 10 shows exemplary smart balls.

FIG. 11A shows exemplary smart rackets while

FIG. 12A-12B show exemplary protective gears, while

FIG. 16A-16C shows exemplary coaching system for skiing, bicycling, and weightlifting/free style exercise, respectively, while

Similar reference characters denote corresponding features consistently throughout the attached drawings.

DETAILED DESCRIPTION OF THE PREFERRED EMBODIMENTS

According to various embodiments of the present disclosure, an electronic device may include communication functionality. For example, an electronic device may be a smart phone, a tablet Personal Computer (PC), a mobile phone, a video phone, an e-book reader, a desktop PC, a laptop PC, a netbook PC, a Personal Digital Assistant (PDA), a Portable Multimedia Player (PMP), an MP3 player, a mobile medical device, a camera, a wearable device (e.g., a Head-Mounted Device (HMD), electronic clothes, electronic braces, an electronic necklace, an electronic accessory, an electronic tattoo, or a smart watch), and/or the like.

According to various embodiments of the present disclosure, an electronic device may be a smart home appliance with communication functionality. A smart home appliance may be, for example, a television, a Digital Video Disk (DVD) player, an audio, a refrigerator, an air conditioner, a vacuum cleaner, an oven, a microwave oven, a washer, a dryer, an air purifier, a set-top box, a TV box (e.g., Samsung HomeSync™, Apple TV™, or Google TV™), a gaming console, an electronic dictionary, an electronic key, a camcorder, an electronic picture frame, and/or the like.

According to various embodiments of the present disclosure, an electronic device may be a medical device (e.g., Magnetic Resonance Angiography (MRA) device, a Magnetic Resonance Imaging (MRI) device, Computed Tomography (CT) device, an imaging device, or an ultrasonic device), a navigation device, a Global Positioning System (GPS) receiver, an Event Data Recorder (EDR), a Flight Data Recorder (FDR), an automotive infotainment device, a naval electronic device (e.g., naval navigation device, gyroscope, or compass), an avionic electronic device, a security device, an industrial or consumer robot, and/or the like.

According to various embodiments of the present disclosure, an electronic device may be furniture, part of a building/structure, an electronic board, electronic signature receiving device, a projector, various measuring devices (e.g., water, electricity, gas or electro-magnetic wave measuring devices), and/or the like that include communication functionality.

According to various embodiments of the present disclosure, an electronic device may be any combination of the foregoing devices. In addition, it will be apparent to one having ordinary skill in the art that an electronic device according to various embodiments of the present disclosure is not limited to the foregoing devices.

In one embodiment, a smart device includes sensor(s) and wireless communication therein. The device can detect tension and communicate to a computer for storage and analysis. The smart device provides an automatic electronic process that eliminates the need for a manual inspection process, and uses electronic detection of stress, eliminating subjective human judgments and producing greater uniformity in maintenance, inspection, and emergency detection procedures.

Figure 1A:
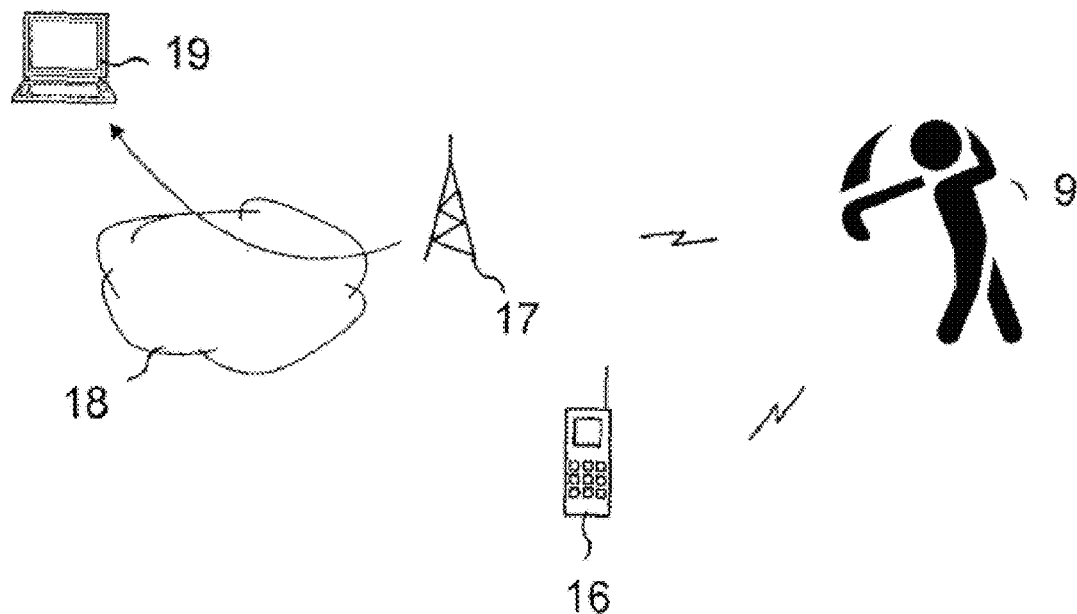
FIG. 1A illustrates an exemplary environment for communicating data from a monitoring device to external computers

FIG. 1A illustrates an exemplary environment for communicating data from a monitoring device to external computers. In FIG. 1A, the monitoring device used for a sport device 9 includes an interface with a radio transmitter for forwarding the result of the comparison to a remote device. In one example, the monitoring device may include an additional switch and user interface. The user interface may be used by the user in order to trigger transmission of the comparison of the hand or foot pattern reference data with the stroke patterns data to the remote device. Alternatively, the transmission may occur automatically each time the device has been used, or may be triggered by placing the sport device in a cradle or base. All parts of the monitoring device may be encapsulated with each other and/or may be integrated into or attached to the body of the sport device 9. Alternatively, a radio transmitter may be arranged separately from the other parts, for instance, in a battery charger, cradle or base of the sport device 9. In that example, the interface 7 may include contact terminals in the sport device 9, which are connected to the corresponding terminals in the battery charger for forwarding the result of the comparison via a wired connection to the transmitter in the battery charger or may be connected by induction or short range wireless communications. The radio transmitter in the battery charger then transmits this comparison result further via the wireless radio connection to the remote device. In FIG. 1A, the remote device may be a mobile phone 16, PDA or computer 19, which receives the information directly from the monitoring device via a short range radio connection, as one example of a transmitter, such as a Bluetooth or a Wifi or a Zigbee connection. In one example, the user of the remote device may receive information about how thoroughly the sport device 9 has been used or the need to provide a replacement sport device. FIG. 1A also illustrates an alternate example of a transmitter, using an intermediate receiver 17 and a network 18, such as a cellular radio system. Also in this example, the radio transmitter may be located in connection with the sport device 9 or alternatively in connection, with a charger, cradle or base station of the sport device 9. In such an example, the comparison result may be transmitted via an intermediate receiver 17 and the network 18 to a remote device 19, 16 located further away than the range of a short range radio system, for example. The remove device 19, 16 may be any device suitable for receiving the signals from the network 18 and providing feedback on an output device. The transmission of information via a cellular radio system to the remote device may allow an advertiser provide an advertisement. For example, an advertisement may be added to the comparison result using network elements in the cellular radio system. The user may receive an advertisement with the comparison result. An advantage with such a solution is that the advertiser may provide revenue offsetting all or a portion of the cost for the transmission of the comparison result from the sport device 9 to the remote device 19, 16.

Figure 1B:
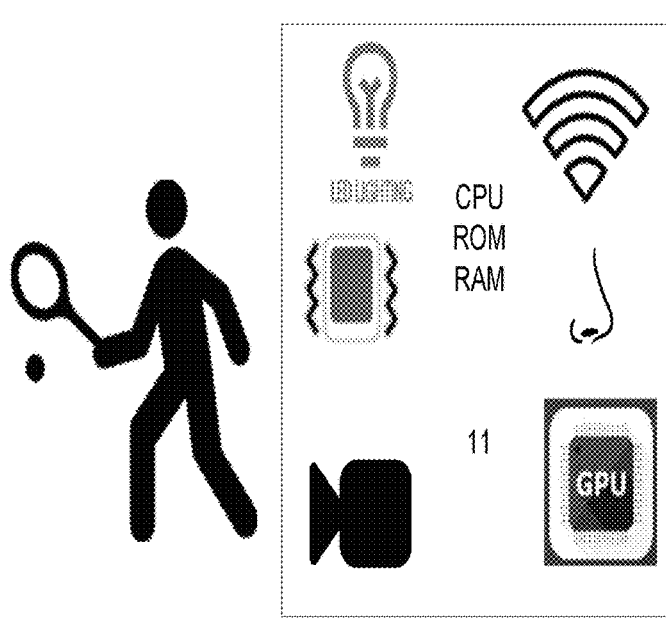
FIG. 1B is a perspective view of an exemplary IoT sport device system.

FIG. 1B shows a block diagram of the unit 9 with processor/RAM/ROM 11. The unit 9 includes a motion sensor, a multi-axis accelerometer, and a strain gage 42. The multi-axis accelerometer may be a two-axis or three-axis accelerometer. Strain gage 21 is mounted in the neck of the racket, and measures force applied to the ball, i.e., force in a z direction. Acceleration and force data are acquired by the microprocessor at a data acquisition rate (sampling rate) of from about 10 to 50 samples/second, e.g., about 20 samples/second. The acceleration data is used to infer motion, using an algorithm discussed below; it is not converted to position data. In this embodiment, because the sensors and strain gage are not in the head region, the head can be removable and replaceable, e.g., by threaded engagement with the handle (not shown), so that the sport device can continue to be used after instrument wear has occurred. Any desired type of removable head or cartridge can be used.

The unit 11 also includes a camera, which can be a 360 degree camera. Alternatively, the camera can be a 3D camera such as the Kinect camera or the Intel RealSense camera for ease of generating 3D models and for detecting distance of objects. To reduce image processing load, each camera has a high performance GPU to perform local processing, and the processed images, sound, and odor data are uploaded to a cloud storage for subsequent analysis.

The unit 11 includes an electronic nose to detect odor. The electronic nose can simply be a MEMS device acting as a particle counter. An embodiment of the electronic nose can be used that includes a fan module, a gas molecule sensor module, a control unit and an output unit. The fan module is used to pump air actively to the gas molecule sensor module. The gas molecule sensor module detects the air pumped into by the fan module. The gas molecule sensor module at least includes a gas molecule sensor which is covered with a compound. The compound is used to combine preset gas molecules. The control unit controls the fan module to suck air into the electronic nose device. Then the fan module transmits an air current to the gas molecule sensor module to generate a detected data. The output unit calculates the detected data to generate a calculation result and outputs an indicating signal to an operator or compatible host computer according to the calculation result.

An electronic tongue sensor can be provided to sense quality of sweat or liquid. The tongue includes a liquid molecule sensor module, a control unit and an output unit. Body liquid is applied or swiped on to the liquid molecule sensor module. The molecule sensor module detects the liquid molecules pumped into by the stirring module. The liquid molecule sensor module at least includes a molecule sensor which is covered with a compound. The compound is used to combine preset liquid molecules. The control unit controls the stirring module to pump liquid to be "tasted" into the electronic tongue device. Then the module transmits a flow current to the liquid molecule sensor module to generate a detected data. The output unit calculates the detected data to generate a calculation result and outputs an indicating signal to an operator or compatible host computer according to the calculation result. Such electronic tongue can detect quality of fog or liquid, among others.

In one embodiment for analyzing tooth structure, restorative materials within a tooth structure, and disease states of a tooth, the unit 11 includes a probe 20 which may be attached to a variety of sport probes, and instruments to afford adaptability to a variety of situations in providing diagnostic information on an object such as a naturally occurring structure, man-made materials placed or found within the structure, diseased or otherwise affected, infected or effected structure, as well as structure that has been eroded, worn by attrition, abraded, abfracted, fractured, crazed, broken or otherwise compromised through sport enthusiast use, misuse, fatigue or longevity of use. The probe 20 generates electrical outputs which are interpreted by a smart phone or computer.

In one embodiment, the probe 20 can be a vibratory transducer that sends out vibrations at known frequency and amplitude. The probe 20 also includes a receiver which can be an accelerometer, for example. The accelerometer is attached to the teeth and connected to a computer. The accelerometer digitizes the received vibrations and provides them into the phone or computer. The transducer can be a single piezoelectric transducer or an array with elements arranged to fit in a mouthpiece or an appliance to be worn over the oral arch. The transducer elements can be mounted in silicone rubber or other material suitable for damping mechanical coupling between the elements. Other materials may also be used for the array construction. For example, the transducer may be formed from one or more pieces of piezocomposite material, or any material that converts electrical energy to acoustic energy. The receiver can also be positioned to fit in the mouthpiece or appliance. One embodiment of the receiver is an accelerometer, but a suitable piezoelectric transducer can serve as the receiver as well.

The software in the computer compares these inputs to known vibration responses corresponding to striking states on a ball or sport object. The computer 30 displays a response on the computer screen for that user.

Figure 1C:
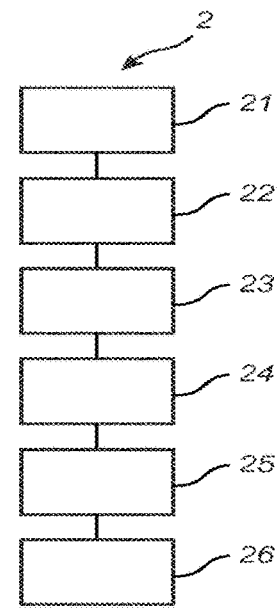
FIG. 1C is an exemplary process supported by the device according to the present invention.

FIG. 1C schematically shows a method or app 2 which may be implemented by the computing unit 11 shown in FIG. 1B. For example, the app 2 may be a computer implemented method. A computer program may be provided for executing the app 2. The app 2 includes code for:

(21) capture user motion with accelerometer or gyroscope
(22) capture VR views through camera and process using GPU
(23) capture user emotion using facial recognition or GSR
(24) model user action using kinematic model
(25) compare user action with idea action
(26) coach user on improvement to user sport techniques.

Figure 2A:
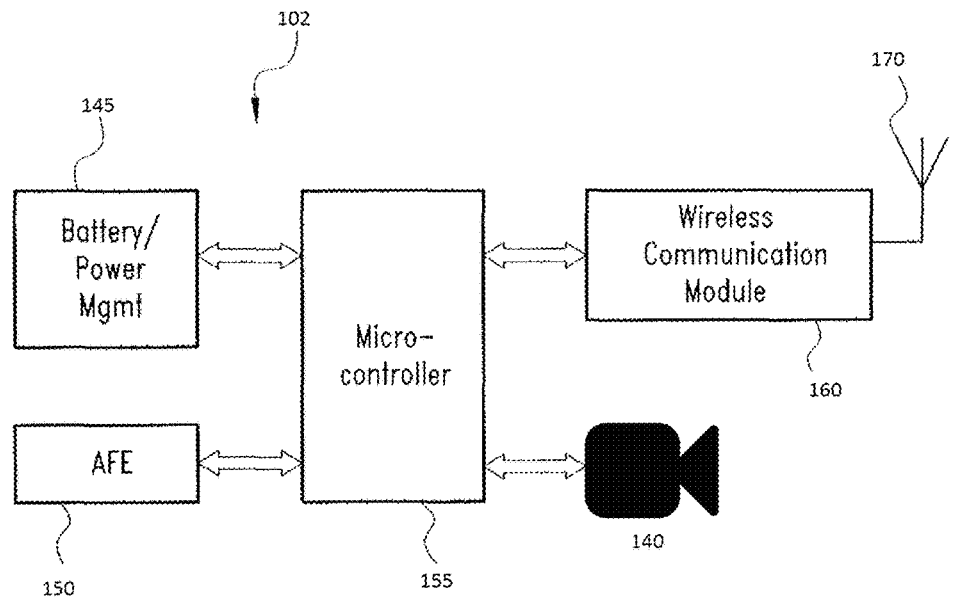
FIG. 2A is a block diagram of an electronic circuit for a smart device.

As shown in FIG. 2A, a microcontroller 155 receives and processes signals from the sensor 112-114, and converts those signals into an appropriate digital electronic format. The microcontroller 155 wirelessly transmits tension information in the appropriate digital electronic format, which may be encoded or encrypted for secure communications, corresponding to the sensed traffic and/or crime indication through a wireless communication module or transceiver 160 and antenna 170. Optionally, a camera 140 can be provided to visually detect traffic and/or crime and movement of the structure. While monitoring of the smart device 100 traffic and/or crime is continuous, transmission of tension information can be continuous, periodic or event-driven, such as when the tension enters into a warning or emergency level. Typically the indicated tension enters a warning level, then an emergency level as tension drops below the optimal range, but corresponding warning and emergency levels above the optimal range can also be used if supported by the smart device 100. The microcontroller 155 is programmed with the appropriate warning and emergency levels, as well as internal damage diagnostics and self-recovery features.

The tension information can take any form, including a simple warning/emergency indication that the tension is approaching or exceeding tension specifications, respectively. While under-tension is known to be the primary cause of structural or mechanical problems associated with devices, over-tension can also be a problem and can also be reported by the smart device 100.

The sensors can detect force, load, tension and compression forces on the device such as the device. Other data includes Acceleration; Velocity; Global absolute displacement; Local relative displacement; Rotation; Strain; Stress; Force; and Static-position video. Wind speed/direction; External temperature; weather parameters (rainfall, humidity, solar radiation, etc.); Internal or structural temperature; Mass loading (occupant count, etc.); Static tilt; Fatigue damage; Corrosion; Acoustic emission; and Moving-position video. A force is simply a push or pull to an object and can be detected by a load cell, pressure cell or strain sensor. A Load: Is simply a force applied to a structure. Ex: weight of vehicles or pedestrians, weight of wind pushing on sides. Tension & Compression are internal forces that make a member longer or shorter. Tension stretches a member and Compression pushes the member closer together. Acceleration can also be detected by Force-Balance (Servo) Piezoelectric Piezoresistive MEMS. Velocity can be measured by force-balance (servo) MEMS, or Mechanical Doppler Heated wire. A local Displacement sensor can be LVDT/ Cable potentiometer Acoustic Optical/laser Temperature Electrical Optical fiber. A rotation sensor can be Gyro MEMS Gyro Tilt Electro-mechanical MEMS. A strain sensor can be a resistance gauge Vibrating wire Optical fiber Corrosion Electrical Chemical sensors. A traffic and/or crime sensor can be a microphone listening to acoustic emission, or Piezoelectric MEMS, for example, and sonar sound processing can be used to detect where crime activity is coming from.

The sensor 112-114, transceiver 160/antenna 170, and microcontroller 155 are powered by and suitable power source, which may optionally include an electromagnetic field (EMF) scavenging device 145, such as those known in the art, that convert ambient EMF (such as that emitted by radio station broadcasts) into small amounts of electrical power. The EMF scavenging device 145 includes a battery to buffer and store energy for the microcontroller 155, sensor 112-114, camera 140 and wireless communications 160/170, among others.

The circuit of FIG. 2A contains an analog front-end ("AFE") transducer 150 for interfacing signals from the sensor 112-114 to the microcontroller 155. The AFE 150 electrically conditions the signals coming from the sensor 112-114 prior to their conversion by the microcontroller 155 so that the signals are electrically compatible with the specified input ranges of the microcontroller 155. The microcontroller 155 can have a CPU, memory and peripheral circuitry. The microcontroller 155 is electrically coupled to a wireless communication module 160 using either a standard or proprietary communication standard. Alternatively, the microcontroller 155 can include internally any or all circuitry of the smart device 100, including the wireless communication module 160. The microcontroller 155 preferably includes power savings or power management circuitry 145 and modes to reduce power consumption significantly when the microcontroller 155 is not active or is less active. The microcontroller 155 may contain at least one Analog-to-Digital Converter (ADC) channel for interfacing to the AFE 150.

The battery/power management module 145 preferably includes the electromagnetic field (EMF) scavenging device, but can alternatively run off of previously stored electrical power from the battery alone. The battery/power management module 145 powers all the circuitry in the smart device 100, including the camera 140, AFE 150, microcontroller 155, wireless communication module 160, and antenna 170. Even though the smart device 100 is preferably powered by continuously harvesting RF energy, it is beneficial to minimize power consumption. To minimize power consumption, the various tasks performed by the circuit should be repeated no more often than necessary under the circumstances.

Stress information from the smart device 100 and other information from the microcontroller 155 is preferably transmitted wirelessly through a wireless communication module 160 and antenna 170. As stated above, the wireless communication component can use standard or proprietary communication protocols. Smart lids 100 can also communicate with each other to relay information about the current status of the structure or machine and the smart device 100 themselves. In each smart device 100, the transmission of this information may be scheduled to be transmitted periodically. The smart lid 100 has a data storage medium (memory) to store data and internal status information, such as power levels, while the communication component is in an OFF state between transmission periods. On the other hand, once the communication commences in the ON state, the microcontroller 155 can execute the following tasks:

1. Neighbor discovery: in this task each smart device 100 sends a beacon identifying its location, capabilities (e.g. residual energy), status. 2. Cluster formation: cluster head will be elected based on the findings in (1). The cluster children communicate directly with their cluster head (CH). 3. Route discovery: this task interconnects the elected cluster heads together and finds the route towards the sink smart device (node) so that minimum energy is consumed. 4. Data transmission: the microcontroller processes the collected color data and based on the adopted data dissemination approach, the smart device 100 will do one of the following. (a) Transmit the data as is without considering the previous status; or (b) transmit the data considering the previous status. Here we can have several scenarios, which include: (i) transmitting the data if the change in reported tension exceeds the warning or emergency levels; and (ii) otherwise, do not transmit.

Figure 2B:
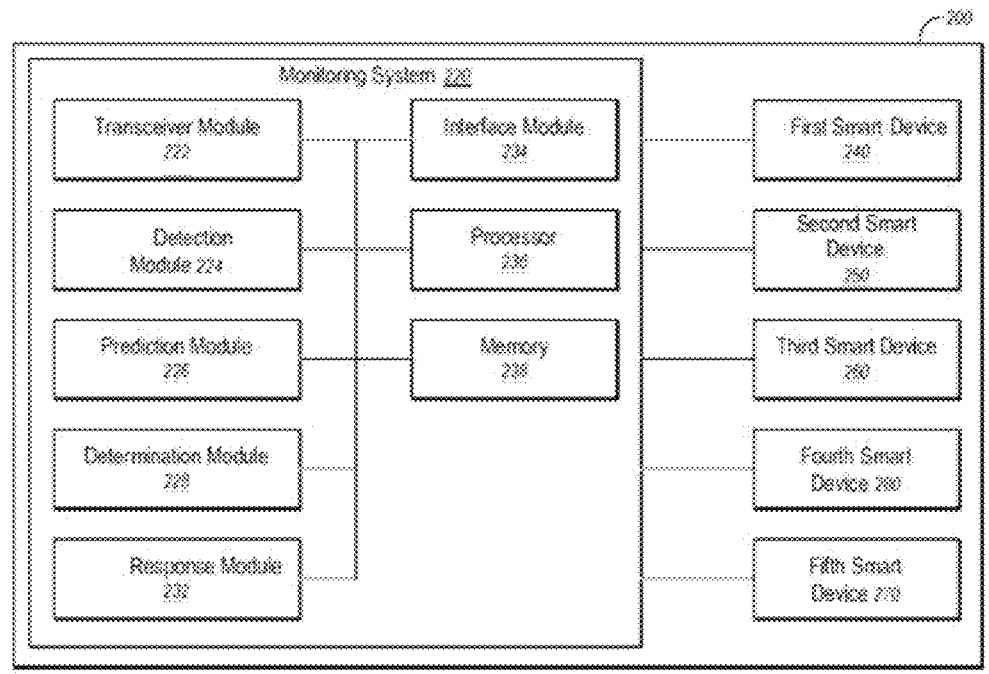
FIG. 2B is a block diagram of a big data system for predicting stress experienced by a structural unit such as a bridge, a building, or a plane, for example.

The electronic of FIG. 2A operates with a big data discovery system of FIG. 2B that determines events that may lead to failure. FIG. 2B is a block diagram of an example stress monitoring system 200 that may be process the stress detected by the smart device 100 of FIG. 1, arranged in accordance with at least some embodiments described herein. Along with the stress monitoring system 220, a first smart device such as a smart device 240, a second smart device 250, a third smart device 260, a fourth smart device 280, and additional sensors 270 may also be associated with the unit 200. The stress monitoring system 220 may include, but is not limited to, a transceiver module 222, a stress detection module 224, a stress prediction module 226, a determination module 228, a stress response module 232, an interface module 234, a processor 236, and a memory 238.

The transceiver module 222 may be configured to receive a stress report from each of the first, second, and third sport smart devices 240, 250, 260. In some embodiments, the transceiver module 222 may be configured to receive the stress reports over a wireless network. For example, the transceiver module 222 and the first, second, and third smart devices 240, 250, 260 may be connected over a wireless network using the IEEE 802.11 or IEEE 802.15 standards, for example, among potentially other standards. Alternately or additionally, the transceiver module 222 and the first, second, and third smart devices 240, 250, 260 may communicate by sending communications over conductors used to carry electricity to the first, second, and third smart devices 240, 250, 260 and to other electrical devices in the unit 200. The transceiver module 222 may send the stress reports from the first, second, and third smart devices 240, 250, 260 to the prediction module 226, the stress detection module 224, and/or the determination module 228.

The stress module 224 may be configured to detect stress on the sport object as detected by the devices 100. The signal sent by the devices 100 collectively may indicate the amount of stress being generated and/or a prediction of the amount of stress that will be generated. The stress detection module 224 may further be configured to detect a change in stress of non-smart devices associated with the unit 200.

The prediction module 226 may be configured to predict future stress based on past stress history as detected, environmental conditions, forecasted stress loads, among other factors. In some embodiments, the prediction module 226 may predict future stress by building models of usage and weight being transported. For example, the prediction module 226 may build models using machine learning based on support vector machines, artificial neural networks, or using other types of machine learning. For example, stress may correlate with the load carried by a bridge or an airplane structure. In other example, stress may correlate with temperature cycling when a structure is exposed to constant changes (such as that of an airplane).

The prediction module 226 may gather data for building the model to predict stress from multiple sources. Some of these sources may include, the first, second, and third smart devices 240, 250, 260; the stress detection module 224; networks, such as the World Wide Web; the interface module 234; among other sources. For example, the first, second, and third smart devices 240, 250, 260 may send information regarding human interactions with the first, second, and third smart devices 240, 250, 260. The human interactions with the first, second, and third smart devices 240, 250, 260 may indicate a pattern of usage for the first, second, and third smart devices 240, 250, 260 and/or other human behavior with respect to stress in the unit 200.

In some embodiments, the first, second, and third smart devices 240, 250, 260 may perform predictions for their own stress based on history and send their predicted stress in reports to the transceiver module 222. The prediction module 226 may use the stress reports along with the data of human interactions to predict stress for the system 200. Alternately or additionally, the prediction module 226 may make predictions of stress for the first, second, and third smart devices 240, 250, 260 based on data of human interactions and passed to the transceiver module 222 from the first, second, and third smart devices 240, 250, 260. A discussion of predicting stress for the first, second, and third smart devices 240, 250, 260 is provided below with respect to FIGS. 5 and 6.

The prediction module 224 may predict the stress for different amounts of time. For example, the prediction module 224 may predict stress of the system 200 for 1 hour, 2 hours, 12 hours, 1 day, or some other period. The prediction module 224 may also update a prediction at a set interval or when new data is available that changes the prediction. The prediction module 224 may send the predicted stress of the system 200 to the determination module 228. In some embodiments, the predicted stress of the system 200 may contain the entire stress of the system 200 and may incorporate or be based on stress reports from the first, second, and third smart devices 240, 250, 260. In other embodiments, the predicted stress of the system 200 may not incorporate or be based on the stress reports from the first, second, and third smart devices 240, 250, 260.

The determination module 228 may be configured to generate a unit stress report for the system 200. The determination module 228 may use the current stress of the system 200, the predicted stress of the system 200 received from the prediction module 224; stress reports from the first, second, and/or third smart devices 240, 250, 260, whether incorporated in the predicted stress of the system 200 or separate from the predicted stress of the system 200; and an amount of stress generated or the predicted amount of stress, to generate a unit stress report.

In some embodiments, one or more of the stress reports from the first, second, and/or third smart device 240, 250, 260 may contain an indication of the current operational profile and not stress. In these and other embodiments, the determination module 228 may be configured to determine the stress of a smart device for which the stress report indicates the current operational profile but not the stress. The determination module 228 may include the determined amount of stress for the smart device in the unit stress report. For example, both the first and second smart device 240, 250 may send stress report. The stress report from the first smart device 240 may indicate stress of the first smart device 240. The stress report from the second smart device 250 may indicate the current operational profile but not the stress of the second smart device 250. Based on the current operational profile of the second smart device 250, the determination module 228 may calculate the stress of the second smart device 250. The determination module 228 may then generate a unit stress report that contains the stress of both the first and second smart devices 240, 250.

In some embodiments, the stress monitoring system 220 may not include the prediction module 226. In these and other embodiments, the determination module 228 may use stress reports from the first, second, and/or third smart devices 240, 250, 260, with the received amount of stress inferred on non-smart devices, if any, to generate the unit stress report. The determination module 228 may send the unit stress report to the transceiver module 222.

In some embodiments, the processor 236 may be configured to execute computer instructions that cause the stress monitoring system 220 to perform the functions and operations described herein. The computer instructions may be loaded into the memory 238 for execution by the processor 236 and/or data generated, received, or operated on during performance of the functions and operations described herein may be at least temporarily stored in the memory 238.

Although the stress monitoring system 220 illustrates various discrete components, such as the prediction module 226 and the determination module 228, various components may be divided into additional components, combined into fewer components, or eliminated, depending on the desired implementation. In some embodiments, the unit 200 may be associated with more or less smart devices than the three smart devices 240, 250, 260 illustrated in FIG. 2.

Figure 3:
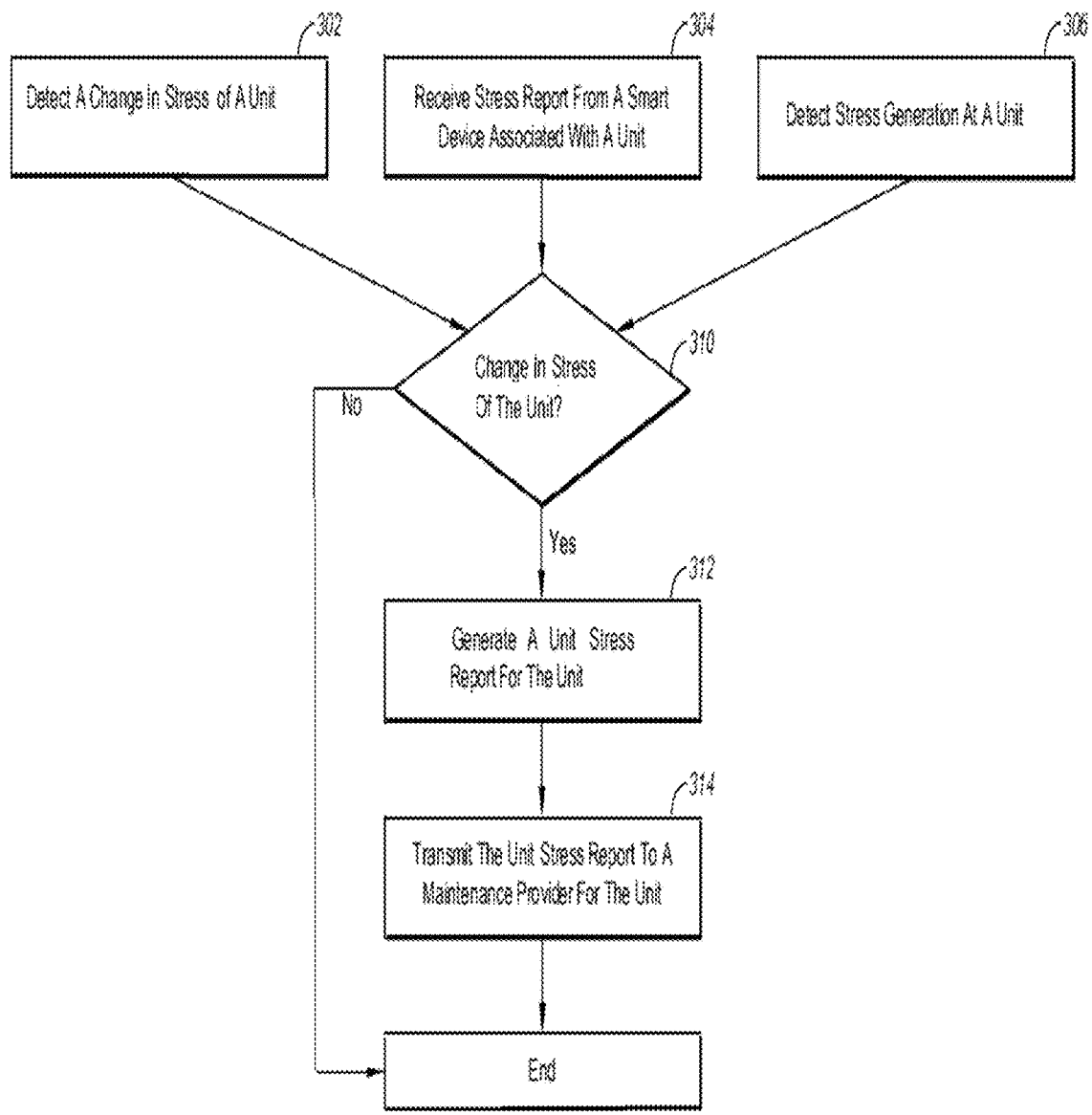
FIG. 3 is a flowchart illustrating one operation of the system of FIG. 2A-2B in detecting stress on a unit.

FIG. 3 is a flow chart of an example method 300 of monitoring stress of a sport or game unit, arranged in accordance with at least some embodiments described herein. The method 300 may be implemented, in some embodiments, by an stress monitoring system, such as the stress monitoring system 220 of FIG. 2. For instance, the processor 236 of FIG. 2B may be configured to execute computer instructions to perform operations for monitoring stress as represented by one or more of blocks 302, 304, 306, 310, 312, and/or 314 of the method 300. Although illustrated as discrete blocks, various blocks may be divided into additional blocks, combined into fewer blocks, or eliminated, depending on the desired implementation.

The method 300 may begin at one or more of blocks 302, 304, and/or 306. The blocks 302, 304, and/or 306 may occur at the same time or at different times and may or may not depend on one another. Furthermore, one or more of the block 302, 304, 306 may occur during the method 300. For example, the method 300 may complete when blocks 304, 310, and 312 occurs and without the occurrence of block 302 and 306.

In block 302, a change in stress of a device (device or beam) associated with a unit may be detected. A non-smart device may by any device that receives stress and does not generate an stress report indicating its stress, for example a legacy racket without IoT electronics. A change in the stress of a non-smart device may be detected using an stress detection module and/or usage meter associated with the unit, such as the stress detection module 224 and/or the smart device 100. For example, non-smart device stress can be estimated by the load the unit carries, the temperature cycling experienced by the unit, for example.

After a change in stress of the non-smart device is detected, the method 300 proceeds to block 310. In block 304, an stress report from a smart device such as the smart device 100 associated with the unit may be received. A smart device may be a device that detects stress and generates and transmits an stress report indicating the stress on the smart device. The stress report may indicate predicted future stress of the smart device. In some embodiments, an stress report may be received at set intervals from the smart device regardless of a change in the stress report. Alternately or additionally, a stress report may be received after a change in the stress of the smart device results in a change to the stress report. After a stress report is received from the smart device, the method 300 proceeds to block 310.

In block 306, stress experienced at the unit may be detected. Stress at the unit may be detected using a stress detection module, such as the stress detection module 224 of FIG. 2B. After detecting stress at the unit, the method proceeds to block 310. At block 310, it is determined if a change in the stress occurred. For example, if an increase in stress occurs at the same time and at the same amount as an increase in the stress of a non-smart device, a change in the stress may not occur. If a change in the stress occurs, the method 300 proceeds to block 312. If no change occurs, the method 300 ends.

At block 312, a unit stress report is generated for the unit. In some embodiments, the unit stress report may indicate the current stress of the unit. Alternately or additionally, the unit stress report may indicate a current and predicted future stress of the unit. At block 314, the unit stress report is transmitted to a maintenance provider. In some embodiments, the unit stress report may be transmitted when the unit stress report indicates a change in stress for the unit that is greater than a predetermined threshold. If the unit stress report indicates a change in stress for the unit that is less than the predetermined threshold, the unit stress report may not be transmitted to the provider of maintenance services.

Figure 5:
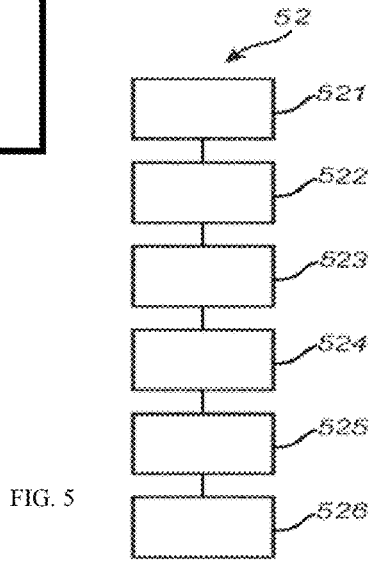
FIG. 5 shows an exemplary process for augmented and/or virtual reality for viewers participating in a game.

FIG. 5 shows in more details the computer 30 and the interface to the probe 20. An amplifier 90 amplifies vibratory output from a transducer 92. A pick up unit having an accelerometer (or an array) 96 receives reflected vibrations from user arm or leg 94, among others. A computer 98 includes a digital converter to digitize output from the pick-up unit and software on the computer 98 can process the captured diagnostic data. Diagnostic software 100 can include a database of known restorations, diseases, and tissue conditions whose signatures can be matched against the capture diagnostic data, and the result can be displayed on a screen for review by the athlete.

Included in one embodiment of the instrumentation is the transmitter or transducer, which will emit the vibrations that will be imparted to the teeth and jaws. This will be connected to a power supply and amplifier, which will allow for a frequency range. On electrical excitation, the transducer emits an outgoing vibration. That vibration will then travel into the arm or leg and down is root into the soft tissues and out into the bones or jaws. The accelerometer or detector will be placed on the bone of interest. It will receive the vibrations from the emitter. The effect of the vibrations on the muscle of interest will generate a pattern of frequency vibrations. Those vibrations will be digitally converted and analyzed against known dental states in the software of the computer. As the data is collected various linear samplings and comparisons will be made against the database. Software will make these comparisons as the data is received from the teeth.

FIG. 5 schematically shows a method or app 52 to perform collaborative VR/AR gaming. The app 52 includes code for:

(51) capture 360 degree view of the live event
(52) detect head position of the viewer
(53) adjust viewing angle on screen based on head position and user posture
(54) render view to simulate action based on user control rather than what the professional is doing
(55) augment view with a simulated object that is powered by viewer action as detected by sensors on viewer body
(56) compare professional result with simulated result and show result to a crowd of enthusiasts for social discussion.

Figure 4:
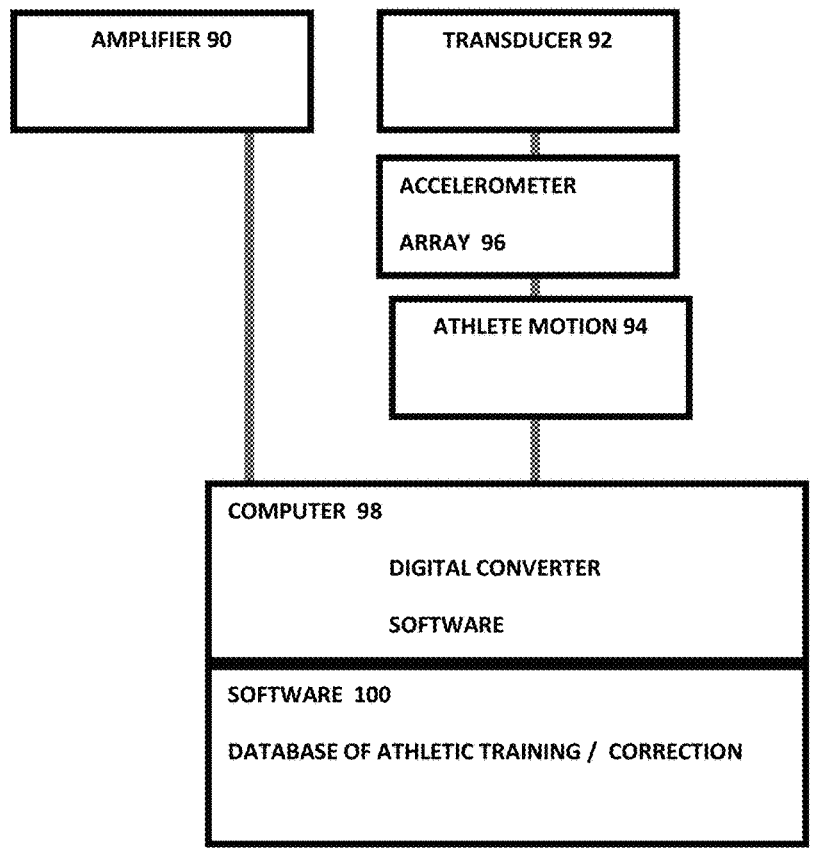
FIG. 4 shows an exemplary sports diagnosis and trainer system for augmented and/or virtual reality.
Figure 6:
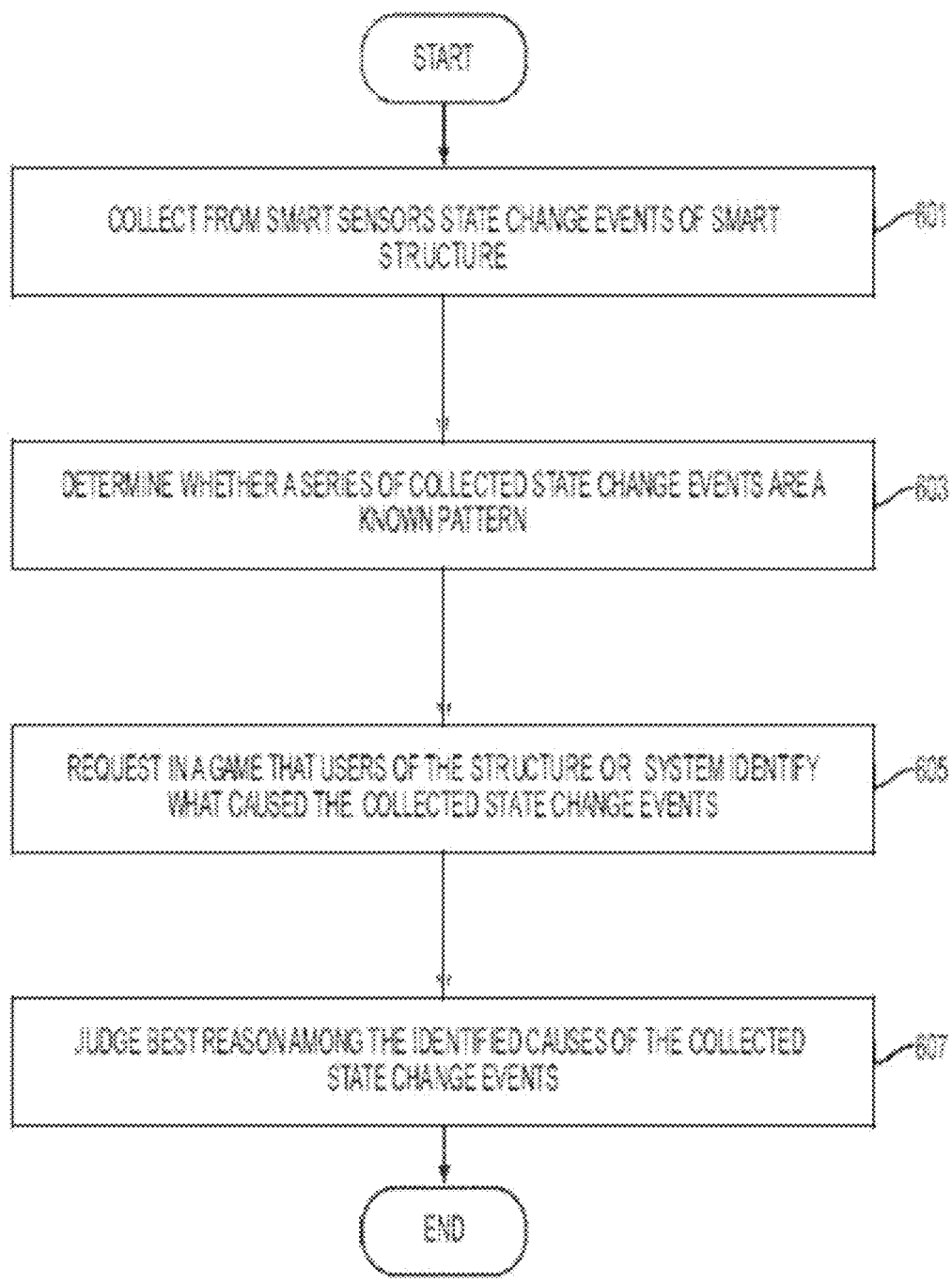
FIG. 6 shows an exemplary process to identify reasons for sensor data changes using a gaming process.

FIG. 6 is a flowchart of a method of an embodiment of the present disclosure. Referring to FIG. 6, a smart system may collect from smart devices state change events of a smart system in operation 601. That is, the smart system of FIG. 4 collects information on each of the group of devices, the smart devices, the smart appliances, the security devices, the lighting devices, the energy devices, and the like. The state change events indicate when there is a change in the state of the device or the surrounding environment. The state change events are stored by the smart system. In operation 603, the system may determine whether a series of the collected state change events are a known pattern. That is, the gateway determines whether there are events which have been correlated or identified in the past. If the collected state change events have been identified in the past, it may be necessary to determine that the smart systems trusts the identification the collected state change events. The trust factor of the identification of the collected state change events may be determined by the number of users who have identified the collected state change events or the number of time collected state change events have been repeated and identified. In operation 605, when the series of the collected state change events is an unknown pattern, request users of the smart system to identify what caused the collected state change events request. That is, the system transmits to a gamification application (hereinafter app) on the user's mobile device a request to identify the collected state change events. The gamification app displays the information and request the user enter information identifying the collected state change events. Each of the mobile devices transmits this information back to the system to the gamification module. In operation 605, the system transmits the each user's identified collected state change events to the other user's of the smart home system and they each vote on the best identification of the collected state change events. Thus, the identified collected change state events that have been repeatedly identified over a period of weeks increases, the trustworthiness of the identification increases. Likewise, if every user of the smart system makes the same identification of the collected change state events, the identified collected change state events may be considered trustworthy at point. Such a determination of a threshold for when the identified collected change state events are considered trustworthy and therefore need not be repeated, is made by a system administrator. However, it will be understood that such a trustworthiness of this type only gives higher confidence of this particular dataset at that point in time. As such further repetition is required, since the sensor data may have noise, the more datasets to be identified to the pattern, the more robust the trustworthiness will be. Until the robustness reaches a threshold, then the system can confirm this is a known trustworthy pattern.

The system can use gaming to help sport enthusiasts improve dental care or maintain teeth hygiene. This may involve use of virtual tools, corresponding to such tools used in normal dental hygiene: sport device, tooth picks, dental floss, gum massaging aids, etc. In this embodiment, the game may, for example, have the object of fighting tooth or gum decay, damage or infection which may be caused by carries or other infectious agents. The user is presented with a library of tools and has to select a tool to treat a certain developing virtual condition, e.g. carries or a gum infection. The game rules determine a certain continuous progress of infection which if not properly "treated" by the user will cause decay of one or more teeth, gum infection, potential bleeding, loss of teeth, etc. In step 13, the user may score points depending on his ability to choose the right tools to treat a particular condition or in avoiding a condition from developing. Next, it is determined whether the condition of the teeth is satisfactory. If yes, the process terminates. If no, then the user is prompted whether he wishes to select another tool. If no, the process terminates. If yes, the process restarts. Here again, the game, in addition to being amusing and providing an insight of the user into his own teeth, may be educational, particularly for children, on teeth oral hygiene methods and on the importance of maintaining oral hygiene.

In accordance with another embodiment of the invention the game may involve use of a variety of virtual imaginary tools such as virtual guns, wands, etc. in order to fight infectious agents of the teeth or gums.

Smart Sport Glove

FIG. 7 shows an exemplary glove which can be thin to provide touch sensitivity or thick to provide shock protection for boxers. A body 12 of the boxing glove 10 includes an impact measuring device 14 is embedded within the glove 12 in an area protected from direct impact. Such an area includes the cuff 15 of the glove 12 or that portion of the glove 12 adjacent a user's palm, or adjacent an inside surface of a user's fingers. Placement of the impact measuring device 14 into the lining of the glove in such an area allows for the force of a blow to be measured without presenting a hazard to the recipient of the blow. Under the embodiment, an impact measuring device 14 would be included in the right glove 12 for a right handed fighter, or the left glove 12 for a left handed fighter. For fighters that are equally effective with both hands, or to improve monitoring accuracy, an impact measuring device 14 would be included in both gloves 12. The impact measuring system 20. The impact measuring system 20 includes an impact measuring device 14 and impact display unit 16. The impact measuring device 14 is linked to the impact display 28 via a radio frequency (rf) link 32. Under the embodiment, the impact measuring device 14 includes at least one 3-axis accelerometer. A thin version of the glove can be worn to detect a golf stroke or a tennis stroke with legacy clubs or rackets that lacks IoT intelligence.

1. A glove comprising:
   a glove body;
   a processor in the glove body and coupled to a wireless transceiver;
   a camera coupled to the glove body;
   a sensor disposed in the glove body; and
   an accelerometer disposed within the glove body to detect acceleration of the glove.

2. The glove of claim 1, at least one sensor selected from a sensor set comprising: a pressure sensor configured to detect at least one pressure event at a glove body external surface location; a glove motion sensor configured to detect at least one motion event of the glove; a digit motion sensor configured to detect at least one motion event of at least one digit of the user; a temperature sensor configured to detect a temperature at a glove body external surface location; and a contact sensor configured to detect a contact event of the glove with a contact object.

3. The glove of claim 1, the sensor comprising at least one of the same as the second sensor or different than the second sensor, the hand exercise event at least one of the same as the second hand exercise event or different than the second hand exercise event.

4. The glove of claim 1, the hand exercise regimen selected from a hand exercise regimen set comprising at least one of: a physical therapy hand exercise regimen; a physical training hand exercise regimen; or a physical performance hand exercise regimen.

5. The glove of claim 1, the glove comprising a gesture identifying component configured to identify at least one hand gesture detected by at least one sensor; the memory configured to, upon receiving an indication of a hand gesture identified by the gesture identifying component, store data corresponding to the hand gesture in the memory; and the device interface configured to, upon connecting to the device, provide at least some of the stored data corresponding to the hand gesture to the device.

6. The glove of claim 1, the glove comprising a plurality of finger receptacles, each having a sensor.

7. The glove of claim 1, comprising a sensor worn by an opponent in wireless communication with the processor to communicate the force of an impact from the glove.

8. A system for measuring a force of impact of a boxing glove of a boxer comprising:
   an accelerometer disposed in the boxing glove of the boxer for measuring the force of impact of the boxing glove on an opponent;
   a radio frequency transmitter disposed in the boxing glove and coupled to the accelerometer for transmitting impact measurements;
   a radio frequency receiver for receiving the impact measurements; and
   a display coupled to the radio frequency receiver for displaying the measured impacts.

Smart Sport Band

FIG. 8 shows an exemplary stick on wearable monitoring device for sports and fitness applications. The wireless sensor electronics 14 is mounted on a band-aid in the example of FIG. 8. The band-aid can be removed upon completion of the sports event. The central patch can be recycled, and the adhesive portion can be disposed. While the embodiment is shown as a band-aid, the inventors contemplate that any suitable bands, straps, attachments can be used in lieu of the band-aid to attach the sensors to the body. For example, in Virtual Reality (VR) sports applications, sensors including gyroscopes and cameras can be positioned on various body portions to capture motion as well as eye tracking, mouth tracking, speech recognition, among others.

One embodiment uses Samsung's Bio-Processor which is an all-in-one health solution chip. By integrating not only Analog Front Ends (AFE), but also microcontroller unit (MCU), power management integrated circuit (PMIC), digital signal processor (DSP), and eFlash memory, it is able to process the bio-signals it measures without the need of external processing parts. Even with its integrated design, the Bio-Processor is particularly innovative thanks to its incredibly small size. When compared to the total area of the discrete parts, the Bio-Processor is only about one fourth of the total combined size, which is ideal for small wearable devices, offering a bounty of options when designing new devices. The Bio-Processor has five AFEs including bio-electrical impedance analysis (BIA), photoplethysmogram (PPG), electrocardiogram (ECG), skin temperature, and galvanic skin response (GSR) into a single chip solution that measures body fat, and skeletal muscle mass, heart rate, heart rhythm, skin temperature and stress level, respectively.

One embodiment provides a flexible and stretchable electronic patch that monitors impact or other events whereby a flexible substrate is geometrically patterned to allow the substrate to undergo substantial stretching and flexing while large regions of the substrate material experiences local strains much lower than the macroscopic applied strain. The geometric patterning of the substrate facilitates continuous low strain domains (LSDs) throughout the substrate—where low strain domains are defined as regions that experience strain levels (magnitude) lower than the macroscopic applied strain. Conventional electronic components can be mounted to the LSDs, and conventional metal traces can be routed through the LSDs, dramatically reducing the stresses transmitted to the components and traces by the substrate during stretching and flexing, and therefore reducing the potential for component debonding, trace cracking, and circuit failure. The geometrically patterned strain relief features (SRFs) are dispersed either regularly or irregularly throughout the substrate. The geometrically patterned SRF regions form "hinge-like" domains. During macroscopic deformation, the SRFs rotate, translate, open, close, or otherwise change shape, causing the "hinge-like" regions to deform, and the remaining larger LSD substrate regions to primarily rotate and translate. The SRFs are designed such that the "hinge-like" regions also exhibit relatively small strain compared to the macroscopic applied strain and thus enable conductive traces, such as copper or gold, to run through the hinges and maintain function during stretching, flexing and twisting of the patch. The substrate can be multilayered to enable running conductive traces, ground layers, vias, and/or components on/in multiple layers through the thickness of the overall substrate. The geometric patterning can be designed to enable different stretching, flexing and twisting, providing uniaxial, biaxial, and multi-axial stretchability or flexibility, and the ability to conform to a variety of surface curvatures. The geometrically patterned substrate offers a means of packaging complex multi-layered electronics designs for monitoring impact (and other) events onto a stretchable and flexible substrate enabling the device to dynamically stretch, bend, twist, and conform to arbitrary shapes. The stretchable, flexible geometrically structure electronics can be fabricated using the same technologies for conventional flexible circuit boards where the stretch-enabling patterning can be imparted at different stages in the fabrication process and can also be fabricated using emerging materials and fabrication methods. The Stretchable bandaid has the stretchable, flexible substrate described above with multiple LSDs for placement of electronic components (e.g., accelerometers, gyroscopes, pressure temperature, gas and fluid sensors, microprocessors, transceivers, GPS, clocks, actuators, vias, and batteries (or other energy source) and multiple patterned hinge-like regions bridging the LSDs which enable the routing of conducting interconnecting traces. The SEHIM patch can take the form factor of a bandaid or bandage or other such wearable form factor. The geometric patterning provides stretch, flex and twist to conform to a body and stretch, flex and twist to move or deform with a body. The bandaid detects impact accelerations, using a 3-axis accelerometer and processes the raw acceleration data in the microprocessor. The processed data is stored in the microprocessor and later (or potentially in real time) transmitted via the Bluetooth to a smart phone, tablet or computer. This embodiment encompasses wireless communication but wired communication may be desirable in some applications and can be accommodated by this invention. The bandaid can be stretched, bent and twisted with the traces and components at low strains to maintain electrical function. In all cases there was effectively no strain on the components and solder joints. The bandaid can also possess an adhesive backing for direct adhesion to the head, body or object. The band can also be coated to provide both added comfort and protection against moisture, water, and other environmental factors. The band can also contain other sensors including gyroscopes, temperature and pressure sensors, moisture sensors, clocks, chemical and/or biological sensors, etc. Features of the smart band can include:

1. A smart patch, comprising:
a band to be placed over a body portion;
a processor in the band and coupled to a wireless transceiver;
a camera coupled to the band;
a sensor disposed in the band; and
an accelerometer disposed within the band to detect acceleration of the band.

2. The patch of claim 1, comprising a plurality of smart patches forming a mesh network and communicating episodically to conserve power.

3. The patch of claim 1 where the electronic components, sensors, and interconnects of the patch monitor, record, process and/or transmit events of interest (such as accelerometers and gyroscopes for impact events, temperature sensors for temperature and/or temperature gradients, pressure sensors, moisture sensors, chemical sensors).

4. The patch of claim 1 comprised for sensing and/or monitoring impact events where the sensors are accelerometers, gyroscopes, and/or pressure sensors.

5. The patch of claim 1 comprised for sensing and/or monitoring and/or controlling ongoing events where the sensors monitor temperature, temperature gradients, motion, position, environmental or chemical levels, or other such information.

6. The patch of claim 1 comprised for sensing events or other information including mounting multiple distributed sensors for obtaining spatial and/or temporal distribution in the data and/or multiple sensors sensing different information and data.

7. The patch of claim 1 including wired or wireless communication, such as a Bluetooth module or a wi-fi module or other transmission module, transmitting and/or receiving information to/from another device.

8. The patch of claim 1 with power and energy sources including batteries, wired or wireless rechargeable batteries, photovoltaics, thermoelectrics, or energy harvesters.

9. The patch of claim 1 with an adhesive backing for directly adhering to a head, a body, or an object.

10. The patch of claim 1 contained in an adhesive or a sleeve for adhering or attaching to a head, a body, or an object.

11. The patch of claim 1 coated with a coating for protection against the elements (water, moisture, dirt, other) and/or for increased comfort to the wearer.

12. The patch of claim 1, comprising a geometrically patterned substrate that contains regions of low strain domains (LSDs) bridged by hingeable strain relief features (SRFs) which also contain low strain regions and enable the stretching, flexing and twisting of the patch while maintaining continuous low strain regions for mounting electronic components and routing traces.

13. The patch of claim 1 for attachment to or on or an object, or embedded in an object.

14. The patch of claim 1 in the form factor of a rectangular or a square or a triangular or other polygon or circular or elliptical or other geometric shape bandage.

15. The patch of claim 1 in the form factor that is or contains any combination of rectangles, triangles, circles, ellipses or other form factors.

16. The patch of claim 1 with different geometric patterning of different numbers and shapes and orientations of low strain domains, different numbers and orientation of geometrically structured hinge-like domains, and different geometries of hinge-like domains.

17. The patch of claim 1 as a programmable circuit board for arbitrary applications.

18. The patch of claim 1 fabricated using current flex circuit manufacturing methods and materials.

19. The patch of claim 1 comprising a cloud storage to receive sensor data.

20. The patch of claim 1 where the polymer layers are current flex manufacturing polymers such as Kapton, polyimides, polyamides, polyesters, or other as well as elastomers such as silicone rubbers (PDMS) or polyurethanes or other elastomers and the interconnects are metals that have high electrical conductivity, such as copper or gold, or where the interconnects are emerging stretchable electronic materials and stretchable conductive inks and materials.

Smart Clothing

FIG. 9 shows an exemplary shirt based embodiment where sensors can be positioned anywhere on the shirt and when worn, can capture position, video, and vital signs. One embodiment uses Samsung's Bio-Processor to process the bio-signals it measures without the need of external processing parts with five AFEs including bioelectrical impedance analysis (BIA), photoplethysmogram (PPG), electrocardiogram (ECG), skin temperature, and galvanic skin response (GSR) into a single chip solution that measures body fat, and skeletal muscle mass, heart rate, heart rhythm, skin temperature and stress level, respectively. Features of the smart clothe can include:

1. A smart clothing, comprising:
   a shirt, underwear, pant or sock;
   a band to be secured to the a shirt, underwear, pant or sock;
   a processor in the band and coupled to a wireless transceiver;
   an EKG amplifier coupled to the band;
   a sensor disposed in the band; and
   an accelerometer disposed within the band to detect acceleration of the band.

2. The clothing of claim 1, comprising a plurality of bands forming a mesh network and communicating episodically to conserve power.

3. The clothing of claim 1 where the electronic components, sensors, and interconnects of the patch monitor, record, process and/or transmit events of interest (such as accelerometers and gyroscopes for impact events, temperature sensors for temperature and/or temperature gradients, pressure sensors, moisture sensors, chemical sensors).

4. The clothing of claim 1 comprised for sensing and/or monitoring impact events where the sensors are accelerometers, gyroscopes, and/or pressure sensors.

5. The clothing of claim 1 comprised for sensing and/or monitoring and/or controlling ongoing events where the sensors monitor temperature, temperature gradients, motion, position, environmental or chemical levels, or other such information.

6. The clothing of claim 1 comprised for sensing events or other information including mounting multiple distributed sensors for obtaining spatial and/or temporal distribution in the data and/or multiple sensors sensing different information and data.

7. The clothing of claim 1 including wired or wireless communication, such as a Bluetooth module or a wi-fi module or other transmission module, transmitting and/or receiving information to/from another device.

8. The clothing of claim 1 with power and energy sources including batteries, wired or wireless rechargeable batteries, photovoltaics, thermoelectrics, or energy harvesters.

9. The clothing of claim 1 with an adhesive backing for directly adhering to a head, a body, or an object.

10. The clothing of claim 1 contained in an adhesive or a sleeve for adhering or attaching to a head, a body, or an object.

11. The clothing of claim 1 coated with a coating for protection against the elements (water, moisture, dirt, other) and/or for increased comfort to the wearer.

12. The clothing of claim 1, comprising a geometrically patterned substrate that contains regions of low strain domains (LSDs) bridged by hingeable strain relief features (SRFs) which also contain low strain regions and enable the stretching, flexing and twisting of the patch while maintaining continuous low strain regions for mounting electronic components and routing traces.

13. The clothing of claim 1 for attachment to or on or an object, or embedded in an object.

14. The clothing of claim 1 in the form factor of a rectangular or a square or a triangular or other polygon or circular or elliptical or other geometric shape bandage.

15. The clothing of claim 1 in the form factor that is or contains any combination of rectangles, triangles, circles, ellipses or other form factors.

16. The clothing of claim 1 with different geometric patterning of different numbers and shapes and orientations of low strain domains, different numbers and orientation of geometrically structured hinge-like domains, and different geometries of hinge-like domains.

17. The clothing of claim 1 as a programmable circuit board for arbitrary applications.

18. The clothing of claim 1 fabricated using current flex circuit manufacturing methods and materials.

19. The clothing of claim 1 comprising a cloud storage to receive sensor data.

20. The clothing of claim 1 where the polymer layers are current flex manufacturing polymers such as Kapton, polyimides, polyamides, polyesters, or other as well as elastomers such as silicone rubbers (PDMS) or polyurethanes or other elastomers and the interconnects are metals that have high electrical conductivity, such as copper or gold, or where the interconnects are emerging stretchable electronic materials and stretchable conductive inks and materials.

Smart Handle

Figure 11A:
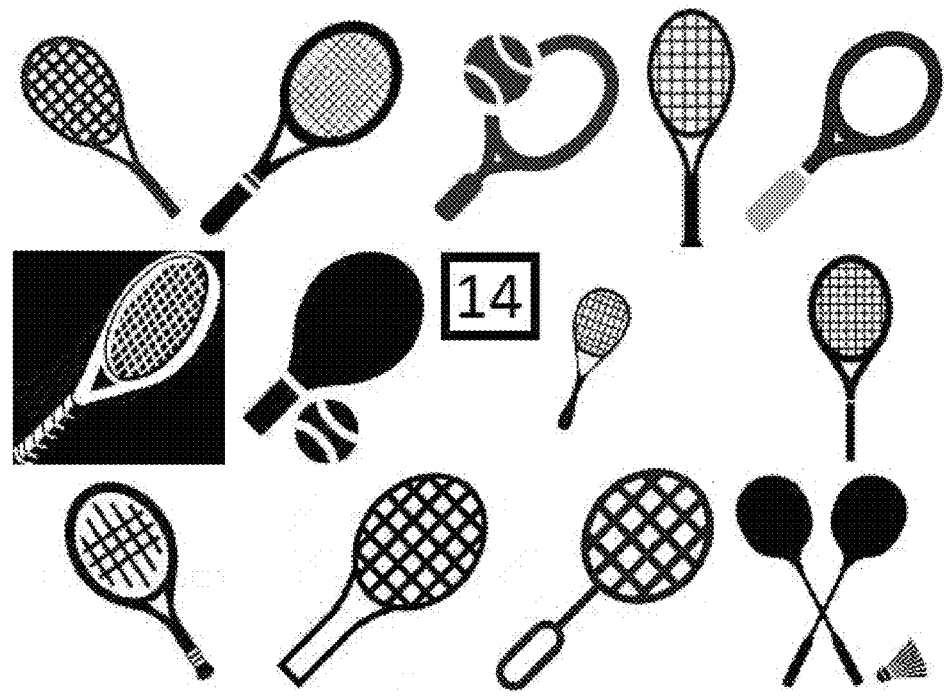
Figure 11B:
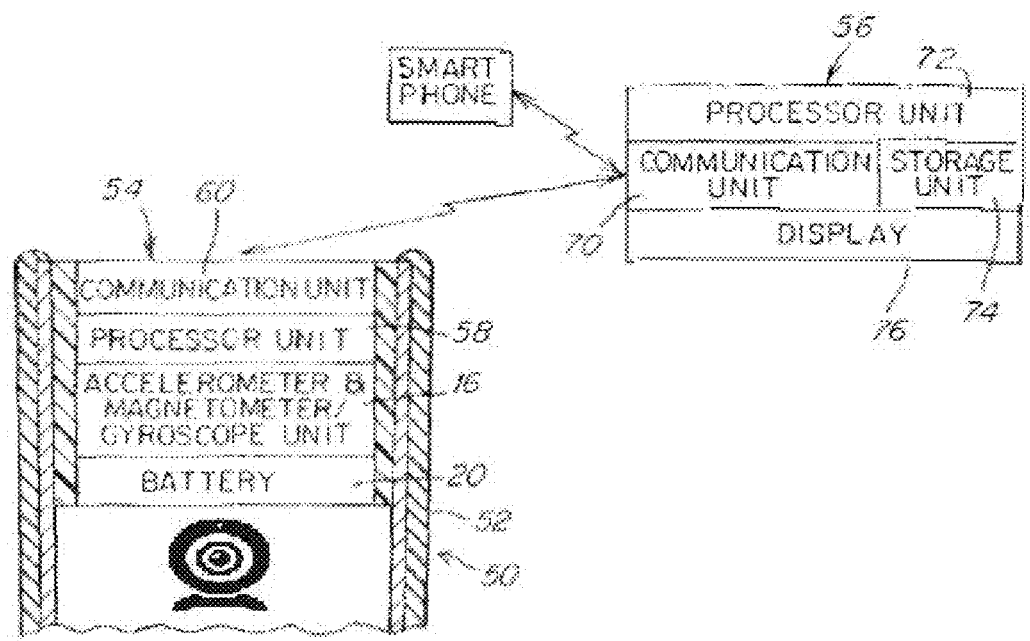
FIG. 11B shows electronics in the handle for golf clubs, rackets, or kung fu sticks.

FIGS. 11A-11B show an exemplary smart handle for sports such as tennis, badminton, table tennis, and golf, among others. The wireless sensor electronics 14 is mounted on a handle in the example of FIG. 11B. The handle can be embedded or can be removed upon completion of the sports event. The sports event does not have to be real, for example, in Virtual Reality (VR) sports applications, sensors including gyroscopes and cameras can be positioned on various body portions to capture motion as well as eye tracking, mouth tracking, speech recognition, among others.

The handle includes a swing analyzer measurement portion 54 in the grip end 52 of the handle of a golf club or a tennis/badminton racket, and a remote or handheld unit 56. The swing analyzer measurement portion 54 includes an accelerometer 16 of combination accelerometer and gyroscope or magnetometer unit, a processor unit 58 coupled to the accelerometer 16, and a battery 20 that is electrically coupled to and provides power to the accelerometer 16 and processor unit 58. A camera is included to capture videos of the swing and also the game in progress for future reference. A communications unit 60 is also housed in the grip end 52 of the golf club 50, receives power from the battery 20, and is coupled to the processor unit 58. Swing analyzer measurement portion 54, with or without the communications unit 60, may be assembled as an integral unit and inserted into a hollow portion of the handle of the golf club or tennis/racket handle 50 at the grip end 52 thereof. Processor unit 58 may be an integrated device that includes hardware and software components capable of processing acceleration measured by the accelerometer(s) 16 and converting the measured acceleration into data about the force on the shaft and position of the face of the club at impact at a set distance. If the measured force exceeds a threshold the measured force or a signal derived therefrom is transmitted via the communications unit 60 to the handheld unit 56. If not, acceleration and face position at impact of the golf club or tennis racket handle 50 is obtained again. The threshold is set so that only acceleration or force measurements arising from actual swings of the golf club 50 are transmitted to the handheld unit 56. Handheld or remote unit 56 includes an application or computer program embodied on a non-transitory computer-readable medium that performs the golf ball carrying distance estimation or prediction steps, as well as manages the training stage described above. Importantly, the handheld unit 56 receives acceleration measurement data from the golf clubs/tennis rackets equipped with a swing analyzer measurement portion 54 and the club face angle in relation to the swing plane, and manages the carrying distance estimation steps for all golf clubs equipped with the swing analyzer measurement portion 54 that are designed to communicate therewith. Handheld or remote unit 56 may be a standalone unit for use only with the golf clubs equipped with the swing analyzer measurement portion 54, and incorporating the application thereon, or may be a smartphone or similar device with the application embodied thereon or downloaded thereto and that can be used for other purposes. Handheld or remote unit 56 includes a communications unit 70 that communicates with the communications unit 60 on each golf club or tennis racket handle 50, i.e., with the communications units present on all of the golf clubs 50 equipped with swing analyzer measurement portions 54 and which have been designated to communicate therewith. Communications unit 70 may be an integral part of the handheld unit 56 as is the case when the handheld unit 56 is a smartphone. Communications unit 70 may also communicate with another device such as a Smartphone, to perform more data manipulations relating to the golf swing and/or swing results to provide more information to the user. The data and the calculation/manipulation results can be stored in the Smartphone and displayed when desired. Currently usable Smartphones are Apple iOS iPhones and Android operating system phones. Handheld or remote unit 56 also includes a processor unit 72, a storage unit 74 and a display 76. When the handheld unit 56 is a smartphone or similar device, all of the processor unit 72, storage unit 74 and display 76 may be integral components thereof. Processor unit 72 performs functions similar to those performed by the processor unit 18 described above, e.g., calculates an estimated carrying distance for the golf ball based on the acceleration measured by the accelerometer(s) 16 and transmitted via the communications units 60, 70, and the type of club provided to the application or computer program in the processor unit 72. Storage unit 74 receives and stores information about the carrying distance of each club as a function of clock or swing position, e.g., in the form of a virtual table associating the type of club, the swing or swing position and the estimated carrying distance.

Other sensors can be used as well. For example, the handle can contain conductive ink to capture biometric. One embodiment uses Samsung's Bio-Processor which is an all-in-one health solution chip to measure bioelectrical impedance analysis (BIA), photoplethysmogram (PPG), electrocardiogram (ECG), skin temperature, and galvanic skin response (GSR) into a single chip solution that measures body fat, and skeletal muscle mass, heart rate, heart rhythm, skin temperature and stress level, respectively. The handle can also contain other sensors including gyroscopes, temperature and pressure sensors, moisture sensors, clocks, chemical and/or biological sensors, etc. Features of the smart handle can include:

1. A smart handle, comprising:
a handle;
a processor in the band and coupled to a wireless transceiver;
a camera coupled to the handle;
a sensor disposed in the handle; and
an accelerometer disposed within the band to detect acceleration of the handle.

2. The handle of claim 1, comprising a plurality of smart handles forming a mesh network and communicating episodically to conserve power.

3. The handle of claim 1 where the electronic components, sensors, and interconnects of the handle monitor, record, process and/or transmit events of interest (such as accelerometers and gyroscopes for impact events, temperature sensors for temperature and/or temperature gradients, pressure sensors, moisture sensors, chemical sensors).

4. The handle of claim 1 comprised for sensing and/or monitoring impact events where the sensors are accelerometers, gyroscopes, and/or pressure sensors.

5. The handle of claim 1 comprised for sensing and/or monitoring and/or controlling ongoing events where the sensors monitor temperature, temperature gradients, motion, position, environmental or chemical levels, or other such information.

6. The handle of claim 1 comprised for sensing events or other information including mounting multiple distributed sensors for obtaining spatial and/or temporal distribution in the data and/or multiple sensors sensing different information and data.

7. The handle of claim 1 including wired or wireless communication, such as a Bluetooth module or a wi-fi module or other transmission module, transmitting and/or receiving information to/from another device.

8. The handle of claim 1 with power and energy sources including batteries, wired or wireless rechargeable batteries, photovoltaics, thermoelectrics, or energy harvesters.

9. The handle of claim 1 with an adhesive backing for directly adhering to a head, a body, or an object.

10. The handle of claim 1 contained in an adhesive or a sleeve for adhering or attaching to a head, a body, or an object.

11. The handle of claim 1 coated with a coating for protection against the elements (water, moisture, dirt, other) and/or for increased comfort to the wearer.

12. The handle of claim 1, comprising a geometrically patterned substrate that contains regions of low strain domains (LSDs) bridged by hingeable strain relief features (SRFs) which also contain low strain regions and enable the stretching, flexing and twisting of the handle while maintaining continuous low strain regions for mounting electronic components and routing traces.

13. The handle of claim 1 for attachment to or on or an object, or embedded in an object.

14. The handle of claim 1 in the form factor of a rectangular or a square or a triangular or other polygon or circular or elliptical or other geometric shape bandage.

15. The handle of claim 1 in the form factor that is or contains any combination of rectangles, triangles, circles, ellipses or other form factors.

16. The handle of claim 1 with different geometric patterning of different numbers and shapes and orientations of low strain domains, different numbers and orientation of geometrically structured hinge-like domains, and different geometries of hinge-like domains.

17. The handle of claim 1 as a programmable circuit board for arbitrary applications.

18. The handle of claim 1 fabricated using current flex circuit manufacturing methods and materials.

19. The handle of claim 1 comprising a cloud storage to receive sensor data.

20. The handle of claim 1 where the polymer layers are current flex manufacturing polymers such as Kapton, polyimides, polyamides, polyesters, or other as well as elastomers such as silicone rubbers (PDMS) or polyurethanes or other elastomers and the interconnects are metals that have high electrical conductivity, such as copper or gold, or where the interconnects are emerging stretchable electronic materials and stretchable conductive inks and materials.

Smart Protective Gear

Figure 12A:
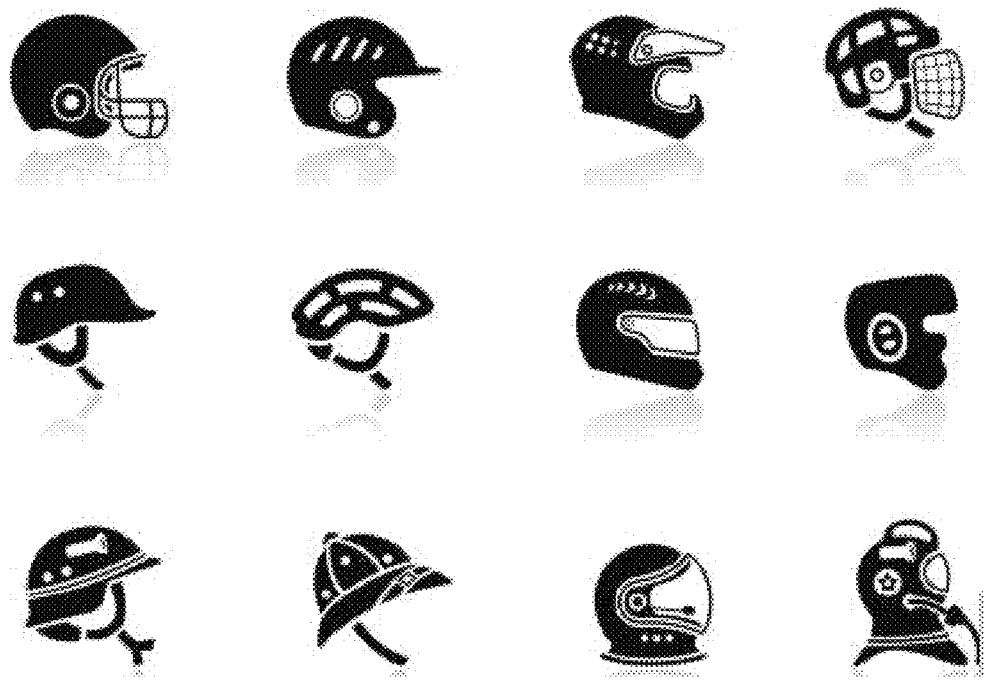
Figure 12C:
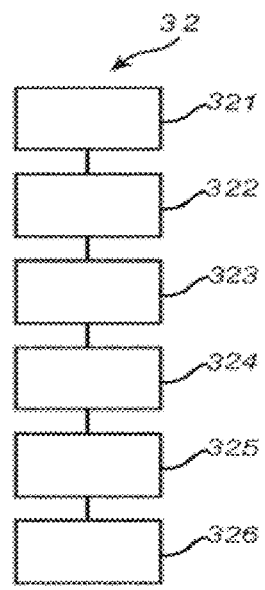
FIG. 12C shows an exemplary process to fabricate mass-customized protective gear.
Figure 12B:
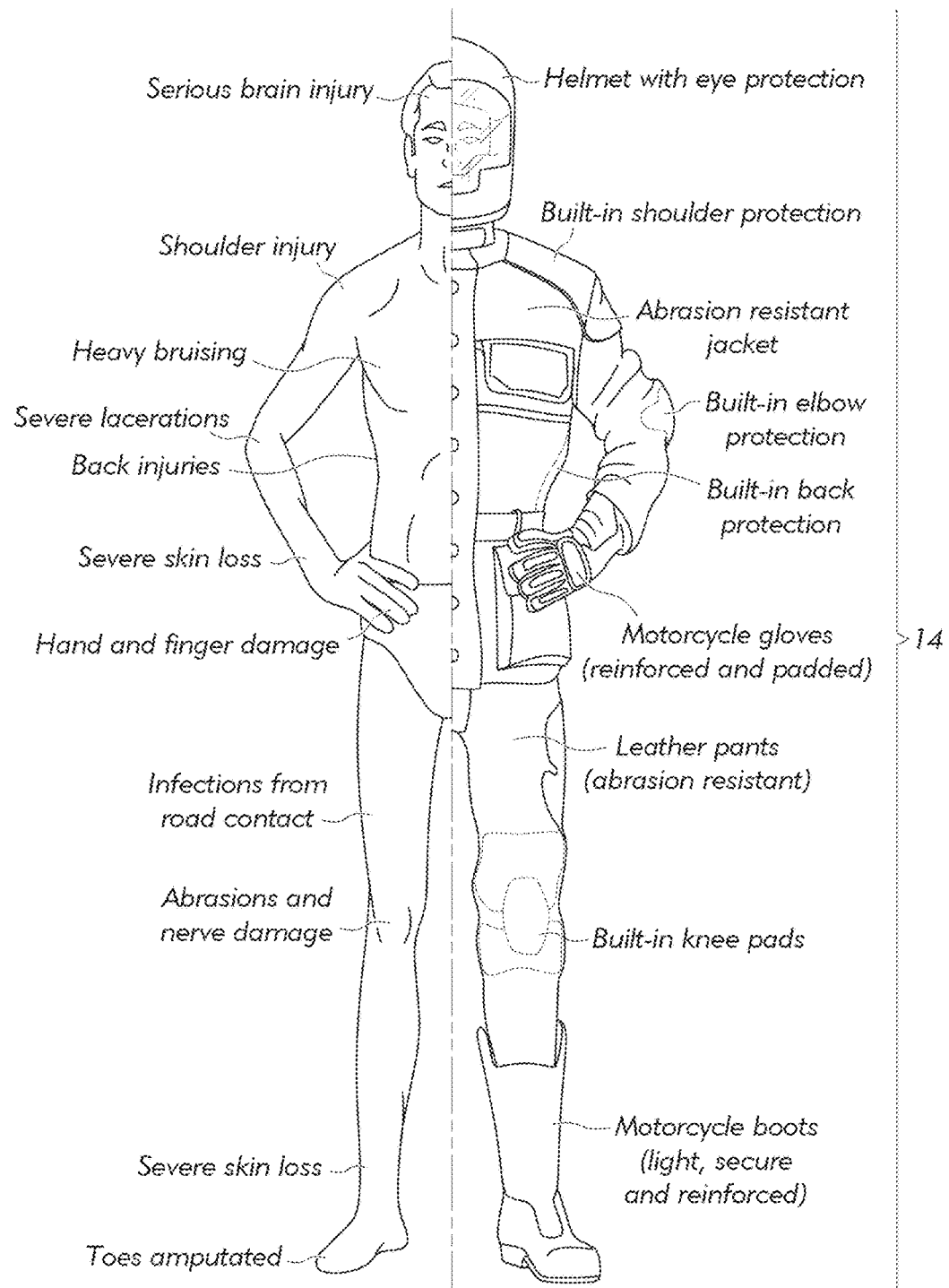

FIGS. 12A-12C illustrate smart protective gears embedded with the IoT sensors and instrumentations to report potential health issues. For soccer, the protection includes shin guards. For football, the protection includes Helmets, Chin Straps & Chin Shields, Cups & Athletic Supporters, Elbow Sleeves & Arm Pads, Back Plates & Rib Protection, Facemasks, Girdles, Helmet Visors, Shoulder Pads, Hip & Tail Pads, Mouthguards, Neck Rolls. For motorcycling, the protection includes helmet, should pads, jacket with back protection, padded gloves, leather pants, knee pads, and boots. For rock climbing, the protection includes shoes, carabiners, webbing, harnesses, among others.

The wireless sensor electronics 14 is mounted on the helmet or shoulder pad in the example of FIG. 12A or 12C. The electronics 14 can be embedded or can be removed upon completion of the sports event. The sports event does not have to be real, for example, in Virtual Reality (VR) sports applications, sensors including gyroscopes and cameras can be positioned on various body portions to capture motion as well as eye tracking, mouth tracking, speech recognition, among others.

The protection gear includes an impact sensor such as an accelerometer to indicate if concussion has occurred. Other sensors can be used as well. For example, the handle can contain conductive ink to capture biometric. One embodiment uses Samsung's Bio-Processor which is an all-in-one health solution chip to measure bioelectrical impedance analysis (BIA), photoplethysmogram (PPG), electrocardiogram (ECG), skin temperature, and galvanic skin response (GSR) into a single chip solution that measures body fat, and skeletal muscle mass, heart rate, heart rhythm, skin temperature and stress level, respectively. The handle can also contain other sensors including gyroscopes, temperature and pressure sensors, moisture sensors, clocks, chemical and/or biological sensors, etc.

Impact sensors, or accelerometers, measure in real time the force and even the number of impacts that players sustain. Data collected is sent wirelessly via Bluetooth to a dedicated monitor on the sidelines, while the impact prompts a visual light or audio alert to signal players, coaches, officials, and the training or medical staff of the team. One such sensor example is the ADXL377 from Analog Devices, a small, thin and low-power 3-axis accelerometer that measures acceleration from motion, shock, or vibration. It features a full-scale range of ±200 g, which would encompass the full range of impact acceleration in sports, which typically does not exceed 150 g's. Specifically designed for concussion and head-trauma detection, at 3 mm×3 mm×1.45 mm, the device is small enough to be designed into a helmet. Sensitivity, listed at 6.5 mV/g with −3 dB bandwidth at 1.6 kHz, is sufficiently high for the application. When a post-impact player is removed from a game and not allowed to return until cleared by a concussion-savvy healthcare professional, most will recover quickly. If the injury is undetected, however, and an athlete continues playing, concussion recovery often takes much longer. In addition, the industry is finding that long-term problems from delayed or unidentified injury can include: Early dementia, Depression, Rapid brain aging, and Death. The cumulative effects of repetitive head impacts (RHI) increases the risk of long-term neuro-degenerative diseases, such as Parkinson's disease, Alzheimer's, Mild Cognitive Impairment, and ALS or Lou Gehrig's disease. The sensors' most important role is to alert to dangerous concussions. Yet, the act of real-time monitoring brings these players to the attention of their coaches not only to monitor serious impacts but, based on the data provided by the sensors, also help to modify a player's technique so that they are not, for example, keeping their head low where they can sustain injury to the front and top of the skull. In the NFL there also has been an aggressive crackdown against hits to the head and neck—a response to the ongoing concussion crisis—resulting in immediate penalty to players using their helmets as a "weapon". Customized mouthguards also have sensors therein. A customized mouthguard has tested to be 99 percent accurate in predicting serious brain injury after near-concussive force, according to an Academy of General Dentistry study 2. Teeth absorb and scatter infrared light, which shows how much force is taking place at the moment of impact.

Features of the smart protective gear can include:

1. A smart protection gear, comprising:
   a wearable surface;
   a processor in the band and coupled to a wireless transceiver;
   a camera coupled to the surface;
   a sensor disposed in the surface; and
   an accelerometer disposed within the band to detect acceleration of the surface.

2. The protection gear of claim 1, comprising a plurality of smart protection gears forming a mesh network and communicating episodically to conserve power.

3. The protection gear of claim 1 where the electronic components, sensors, and interconnects of the protection gear monitor, record, process and/or transmit events of interest (such as accelerometers and gyroscopes for impact events, temperature sensors for temperature and/or temperature gradients, pressure sensors, moisture sensors, chemical sensors).

4. The protection gear of claim 1 comprised for sensing and/or monitoring impact events where the sensors are accelerometers, gyroscopes, and/or pressure sensors.

5. The protection gear of claim 1 comprised for sensing and/or monitoring and/or controlling ongoing events where the sensors monitor temperature, temperature gradients, motion, position, environmental or chemical levels, or other such information.

6. The protection gear of claim 1 comprised for sensing events or other information including mounting multiple distributed sensors for obtaining spatial and/or temporal distribution in the data and/or multiple sensors sensing different information and data.

7. The protection gear of claim 1 including wired or wireless communication, such as a Bluetooth module or a wi-fi module or other transmission module, transmitting and/or receiving information to/from another device.

8. The protection gear of claim 1 with power and energy sources including batteries, wired or wireless rechargeable batteries, photovoltaics, thermoelectrics, or energy harvesters.

9. The protection gear of claim 1 with an adhesive backing for directly adhering to a head, a body, or an object.

10. The protection gear of claim 1 contained in an adhesive or a sleeve for adhering or attaching to a head, a body, or an object.

11. The protection gear of claim 1 coated with a coating for protection against the elements (water, moisture, dirt, other) and/or for increased comfort to the wearer.

12. The protection gear of claim 1, comprising a geometrically patterned substrate that contains regions of low strain domains (LSDs) bridged by hingeable strain relief features (SRFs) which also contain low strain regions and enable the stretching, flexing and twisting of the protection gear while maintaining continuous low strain regions for mounting electronic components and routing traces.

13. The protection gear of claim 1 for attachment to or on or an object, or embedded in an object.

14. The protection gear of claim 1 in the form factor of a rectangular or a square or a triangular or other polygon or circular or elliptical or other geometric shape bandage.

15. The protection gear of claim 1 in the form factor that is or contains any combination of rectangles, triangles, circles, ellipses or other form factors.

16. The protection gear of claim 1 with different geometric patterning of different numbers and shapes and orientations of low strain domains, different numbers and orientation of geometrically structured hinge-like domains, and different geometries of hinge-like domains.

17. The protection gear of claim 1 as a programmable circuit board for arbitrary applications.

18. The protection gear of claim 1 fabricated using current flex circuit manufacturing methods and materials.

19. The protection gear of claim 1 comprising a cloud storage to receive sensor data.

20. The protection gear of claim 1 where the polymer layers are current flex manufacturing polymers such as Kapton, polyimides, polyamides, polyesters, or other as well as elastomers such as silicone rubbers (PDMS) or polyurethanes or other elastomers and the interconnects are metals that have high electrical conductivity, such as copper or gold, or where the interconnects are conductive inks.

Custom Gear

In one aspect, the protective gear is custom formed to the athlete's body. This is done in FIG. 12C as follows:

321) perform 3D scan of person and create 3D model
322) form positive mold from the 3D model
323) place mold into 2 phase 3D printer to form a negative
324) put composite material into mold and form composite protection gear
325) embed IoT electronics into one or more locations into the composite protection gear
326) link IoT electronics with mobile devices and cloud based storage and process impact data and warn user if impact is unsafe.

The protection gear or footwear can be custom produced at the request of a customer, who can specify the nature of the customization for one or more pairs of helmet, protective gear, or footwear. Each helmet of the footwear may have a different design, message or message portion designed into it and rendered using the bed of pins described below to make the custom helmet or shoe design messages or shapes, and then the bottom sole can be fabricated using the reformable bed described below. Once the negative is fixed in the reformable bed, suitable materials for the bottom sole can be deposited and cured and can include rubber, plastic, or foam. Further customization can be done by a Computerized Numerical Control (CNC) where component design can be integrated with computer-aided design (CAD) and computer-aided manufacturing (CAM) programs. The device can be programmed to use a number of different tools-drills, saws, and so on. Alternatively a number of different machines can be used with an external controller and human or robotic operators that move the component from machine to machine. Regardless, a series of steps needed to produce a part can produce a part that closely matches the original CAD design in a highly automated fashion. In accordance with aspects of the subject matter disclosed herein through the use of reformable bed and a suitably programmed CNC tools, customized footwear with custom cut sole designs, can cost effectively be created in small quantities and yet scalable for mass-customization.

1. A method of producing a component of customized wearable protection gear, the method comprising:
capturing the 3D model of a person and adjusting the 3D model to customize a shape to optimize protection or performance;
using a rapid prototyping machine such as 3D printer or a bed of pins to render a positive model of the shape; and
impressing the positive model into a reformable mold to form the component of the wearable protective gear.

2. The method of claim 1, wherein the component comprises a helmet, protective padding, shoulder padding, seat, shoe, or sole.

3. The method of claim 1, comprising fabricating a plurality of components in parallel.

4. The method of claim 1, wherein the component comprises shin guard, Helmet, Chin Strap, Chin Shields, Cup, Athletic Supporter, Elbow Sleeve, Arm Pad, Back Plate, Rib Protection, Facemask, Girdle, Helmet Visor, Shoulder Pad, Hip & Tail Pad, Mouthguard, Neck Roll, Knee Pad, Boot.

5. The method of claim 1, comprising joining the component with an upper to form a shoe.

6. The method of claim 5, wherein the shoe comprises a jogging shoe, basketball shoe, soccer shoe, running shoe, climbing shoe, flip flop, sandal, or boot.

7. The method of claim 1, wherein the reformable mold comprises sand having a liquid state and a solid state.

Shock Protection

In one embodiment, the sole is not completely filled with material, but is formed as a lattice structure. The system generates triangulated surfaces for export to additive manufacturing (AM) processes. Implementing a process that coverts a CAD object into an image, known as voxelisation, the company uses an image-based method which allows designers to generate implicitly defined periodic lattice structures suitable for additive manufacturing applications and finite element analysis (FEA). The system generates robust lattice structures can overcome the problems faced with hollowing out a part to reduce weight and optimize designs prior to 3D printing. Cellular lattice structures can be used to replace the volume of CAD and image-based parts, reducing weight whilst maintaining optimal performance. In this way, the shoes can be light weight yet strong and provide shock impact absorption during running for the wearer.

Topology optimization can be used to drive the material layout including the lattice regions. From this new topology optimization implementation, the system can identify void regions in the design space, where the material can be removed, regions where solid material is needed, and regions where lattice structure is required. This allows the system to generate the optimal hybrid or blended solid-lattice design based on desired functionality of the part.

Lattice structures can be considered as porous structures. In the case of topology optimization, the semi-dense elements are like the porous media. To refine the design, a second-phase involves a detailed sizing optimization where the end diameters of each lattice cell member are optimized. This allows for further weight reduction while meeting design requirements, such as buckling, stress, and displacement.

A piezo material can be actuated to generate a vibration that cancels incoming shock on the wearer. In one embodiment, the system tracks the shock such as the foot contact patterns and generates an anti-vibration signal to cancel the shock generated when the foot contacts the ground. In this embodiment, a processor receives foot ground contact using an accelerometer. The stride pattern is determined, and the next foot ground contact is detected, and the piezo material is actuated with a counter signal to cancel the expected shock. This is similar to the noise cancellation, except the vibration/shock is canceled.

In one hybrid embodiment, the shoes incorporate passive and active isolation elements. The passive component consists of springs which support the load weight and provide isolation over a broad spectrum. These springs provide a basic level of isolation in the lower frequencies and excellent isolation in the higher frequencies (above 200 Hz). They also support the load while allowing for travel of the actuators in the active component. The performance of the springs is augmented and corrected by an active isolation component. The active isolation component consists of vibration sensors, control electronics, and actuators. The vibration sensors are piezo accelerometers. A plurality of sensors in each isolation system are positioned in different orientations to sense in all six degrees of freedom. The piezo accelerometers convert kinetic vibration energy into electrical signals which are transmitted to the control electronics. The electronics reconcile and process the signals from the various sensors using a processor. The electronics then send a cancellation signal to the actuators. The actuators generate vibrations that are equal to the incoming vibrations but out of phase in relation to the incoming vibrations. This results in cancellation of the incoming vibrational noise, leaving the wearer undisturbed. This process occurs within 5-20 milliseconds of a vibration entering the system.

Multi-Phase Manufacturing (MPM)

While conventional additive manufacturing 3D printers can be used for mass-customization of the shoes, the material available is limited and the print speed is slow, leading to fragile and expensive shoes. FIGS. 13A-13D and 14A-14D show exemplary systems and techniques for manufacturing in volume with a wide range of materials are disclosed for fabricating custom protective gears, helmets, pads, or shoes at mass customization scale. The system can also be further cleaned up after manufacturing using CNC for smoothing the soles, stitching fabrics onto the sole, or any other required post-processing manipulation of the fabricated shoes.

In one aspect, systems and methods are disclosed for shaping a reformable material by holding a volume of particles inside a container having a first elastomeric membrane surface; infusing the volume with a liquid to mobilize the volume of particles; and pressing a master shape into the membrane with atmospheric pressure.

In another aspect, a method to form an object includes infusing a liquid into a container having a first elastomeric membrane surface; pressing a master shape into the membrane with atmospheric pressure; and shaping a reformable material into the object according to the master shape.

In yet another aspect, a method to form an object includes infusing a liquid into a container having a frame with first and second elastomeric membranes; a first port to deaerate the volume of particles; and a second port to infuse the volume with a liquid for mobilizing the volume of particles; pressing a master shape into the membrane with atmospheric pressure; and shaping a reformable material into the object according to the master shape.

Implementations of the above aspects may include one or more of the following. The volume of particles can be deaerated. The liquid can be extracted through one or more screen elements placed proximal to the volume of particles. The atmospheric pressure continues to hold the particles in place against the elastomeric membrane when the master shape is removed from the outer surface of the membrane. The method includes heating and driving liquid from the particle volume. A residue of a binding adhesive is left to lock the particles into a continuous force-resisting mass. A complementary shape is impressed to the master shape in the membrane. A rigid outside frame can be used with top and bottom elastomeric membranes facing the top and bottom surfaces of the container. The master shape can be pressed against the top elastomeric membrane of the container by atmospheric pressure. The pressing operation includes applying a flexible vacuum cap which is sealed over the shape and against the container's top surface membrane; evacuating air from a space between the top membrane and the vacuum cap; extracting liquid from the volume; and pressing the particles within the container by atmospheric force acting in opposed directions against the vacuum cap and the bottom surface membrane. Air can be introduced into the vacuum cap, and then the cap and the master shape can be removed from the formed surface of the elastomeric membrane. The container is formed against the master shape. The method includes placing the master shape on an air-impermeable surface; placing a membrane of the container over the shape; and placing a vacuum cap or a vacuum-bagging film over the container to effect forming of the elastomeric membrane against the master shape. An envelope with a vacuum seal on its perimeter can be used to contain a mass of particles and to extract air from between the master shape and the envelope. The master shape can be placed on the top elastomeric surface of a first rigid-framed container and a membrane surface of a second container can be placed over the master shape. The second container fits inside the frame of the first container and a vacuum cap is placed over and sealed outside the second container against the surface membrane of the first container. The method includes evacuating the volume under the vacuum cap and pressing the master shape between the elastomeric sides of the first and second containers. The liquid is extracted so that the two volumes of particles are pressed together and against the membranes surrounding the contained shape. The vacuum cap can be vented with air and removed; the top container can then be removed; and the shape can then be removed from the membrane of the bottom container. The top container can be placed over the bottom container; and forming a closed, shaped cavity complementary to the surface of the master shape used to form the cavity. Two identical containers of either the first or the second container can be pressed around a master shape with or without using the vacuum cap. The containers can be joined and sealed by either a seal mounted on one or both of the containers or by seals mounted on a seal ring which fits between the two containers. The liquid can be extracted prior to the master shape being removed from the shaped reformable material. The liquid can be withdrawn to leave a residue of liquid on the shaped reformable material; and solidifying the residue. The method can include preforming a surface material over the master shape as with thermoforming or additive processing. The container walls can be air and liquid impermeable. An inelastic formable surface can be used that conforms to the master shape surface. A surface can be formed over the master shape to conform to the master shape and the shaped material surface can be pressed against the volume of particles without deforming the shaped material surface. The method includes providing a release surface to the master shape; pressing the master shape against the volume of particles to form the object against the release surface; and removing the object from the master shape with the release surface. The release surface can be applied to the master shape with a surface element covering the reformable material surface not overlaid with the master shape surface.

In another aspect, an apparatus to form an object in accordance with a master shape includes a container to hold a volume of particles, said container having a first elastomeric membrane surface; a first port to deaerate the volume of particles; and a second port to infuse the volume with a liquid for mobilizing the volume of particles; and a press coupled to the container to move the master shape into the membrane to shape a reformable material into the object according to the master shape.

Implementations of the above aspect may include one or more of the following. One or more screen elements can be placed proximal to the volume of particles to extract the liquid. Atmospheric pressure can be used to hold the volume of particles in place against the elastomeric membrane when the master shape is removed from the membrane. A heater can be used to heat and drive liquid from the particle volume. The container can be a rigid outside frame and top and bottom elastomeric membranes facing the top and bottom surfaces of the container, and wherein the master shape is pressed against the top elastomeric membrane of the container by atmospheric pressure. The apparatus can include a flexible vacuum cap sealed over the shape and against the container's top surface membrane; a third port to evacuate air from a space between the top membrane and the vacuum cap; and pressing of the particles within the container by atmospheric force acting in opposed directions against the vacuum cap and the bottom surface membrane. Air can be introduced into the vacuum cap and then the cap and the master shape can be removed from a surface of the elastomeric membrane. The master shape can be placed between an air-impermeable surface and the membrane of the container and wherein a vacuum cap or a vacuum-bagging film is placed over the container to form the elastomeric membrane against the master shape. An envelope with a vacuum seal on its perimeter can be used to contain a mass of particles and to extract air from between the master shape and the envelope. The master shape can be placed on the top elastomeric surface of a first rigid-framed container and placing a membrane surface of a second container over the master shape. The second container fits inside the frame of the first container and a vacuum cap is placed over and sealed outside the second container against the surface membrane of the first container. A vacuum pump can evacuate the volume under the vacuum cap and press the master shape between the elastomeric sides of the first and second containers. A pump can extract the liquid so that the two volumes of particles are pressed together and against the membranes surrounding the contained shape. The vacuum cap can be vented with air and removed; the top container is removed; and the shape is removed from the membrane of the bottom container and the top container is placed adjacent the bottom container to form a closed, shaped cavity complementary to the surface of the master shape used to form the cavity. The first and second containers can be identical and can be pressed around a master shape without using the vacuum cap. The containers can be joined and sealed by either a seal mounted on one or both of the containers or by seals mounted on a seal ring which fits between the two containers. A seal ring can be used to channel vacuum or air pressure between the containers and to hold the master shape in a precise orientation and position between the two opposed containers. An expander can be used within the container to press the particulate material against cavity walls of the container. The apparatus can include a second container cooperating with the first container to form a complementary cavity from the master shape; and a third container placed in the complementary cavity to replicate the master shape. A rigid frame or a flexible-edge frame can be used. The frame can form a continuous surface complementary to a master shape's surface. A second elastomeric membrane can be used, and the elastomeric membranes can overlap or abut each other. Additional containers each having a membrane can be used with the container's membrane to form a continuous surface of membranes. Further, additional containers can be used to form a shape complementary to the interior of a master cavity.

In another aspect, an apparatus to form an object in accordance with a master shape includes a container to hold a volume of particles, said container having a frame with first and second elastomeric membranes; a first port to deaerate the volume of particles; and a second port to infuse the volume with a liquid for mobilizing the volume of particles; and a press coupled to the container to move the master shape into the membrane to shape a reformable material into the object according to the master shape.

Implementations of the above aspect may include one or more of the following. The second membrane is bonded to the frame. The first membrane is mounted to a seal. A clamp can secure at least one membrane to the frame. One or more ports can be provided on the frame. Liquid, evacuation, and vacuum-activated seal tubes can be mounted to the frame. A rim evacuation screen element can be positioned in the frame. The frame can be rigid or flexible. A vacuum activated seal can be provided on the frame. A tube can be used for evacuating and filling the container. Double layer screens having feed elements to distribute and extract liquid through the volume of particles can be used. One or more screens can be used to conform to the master shape. One or more internal screens can be mounted with the particles flowing on both sides of each internal screen. The frame can have one or more containers joined together around the master shape or alternatively can have one or more containers joined by vacuum seals. One or more feed tubes can connect to an interior element inside the membrane. A flexible spine element can be used within an interior cavity of the container. One or more reinforcement fibers can be used, and in certain implementations, the fibers can be distributed in bundles within the volume of particles. An air pump or source can be used to provide internal pressurization. A vacuum source can provide a vacuum between a cavity in the container and the container. An air source and a vacuum source can alternately pressurize and vent the container to distribute the volume of particles therein. A seal ring can be used. The seal rings can be mounted against seals or can be mounted with attached seals. The attached seals can be vacuum activated. A second container can be joined with the container and wherein a vacuum is formed in an interior of the joined containers. The master shape can be mounted on the seal ring. Flanges can be mounted to control a mating line between opposed membranes of containers. A second container can be positioned within a cavity formed by an outside container. A vacuum seal can be used with a vacuum cap. A vacuum tube can be used that penetrates through the membrane. A vacuum cap with mounted container can be used in place of the membrane. One or more screen elements can be placed proximal to the volume of particles to extract the liquid. Atmospheric pressure holds the volume of particles in place against the elastomeric membrane when the master shape is removed from the membrane. A heater can be used to heat and drive liquid from the particle volume. The container can have a rigid outside frame and top and bottom elastomeric membranes facing the top and bottom surfaces of the container, and wherein the master shape is pressed against the top elastomeric membrane of the container by atmospheric pressure. An envelope with a vacuum seal on its perimeter can contain the mass of particles and extract air from between the master shape and the envelope. The master shape can be placed on the top elastomeric surface of a first rigid-framed container and a membrane surface of a second container placed over the master shape. An expander within the container can be used to press the particulate material against master shapes and against cavity walls of other containers. The apparatus can have a second container cooperating with the first container to form a complementary cavity from the master shape; and a third container placed in the complementary cavity to replicate the master shape. A second elastomeric membrane can be used that either overlaps or abuts the adjacent membrane. Additional containers each having a membrane coupled to the container can be used to form a continuous surface of membranes. Additionally, one or more additional containers can form a shape complementary to the interior of a master cavity.

In yet another aspect, a base station is disclosed to form an object in accordance with a master shape. The base station includes a liquid receiver; a vacuum source to evacuate air from the liquid receiver; an air compressor, pump or source to generate pressurized air; and a controller coupled to the liquid receiver, the vacuum source and the air compressor to form the object.

Implementations of the base station can include one or more of the following. Tubes can be used to provide vacuum and to control the flow of liquids to and from the receiver. Valves, sensors, and other circuits can be interfaced with the controller. An electrical power source can be used to provide power to operate valves, sensors, the vacuum pump and the air compressor. The controller can be a menu-driven process controller. A heater can be used to vaporize and expel liquid from containers of reformable material. The reformable material creates contours of the master shape or alternatively can be molded against a complementary surface of an elastomeric membrane. The liquid contains a soluble binder, which can be left on a shaped volume of particles. The binder locks a shaped volume of particles in place after the liquid is removed. The heater can be a radiant heater, a convective air heater, microwave heater, radio-frequency heater, or inductive heater. The heater can include one or more heating elements within the container. The heater is controlled by the controller. A container can be used to hold a volume of particles, said container having a frame with first and second elastomeric membranes; a first port to deaerate the volume of particles; and a second port to infuse the volume with a liquid for mobilizing the volume of particles; and a press coupled to the container to move the master shape into the membrane to shape a reformable material into the object according to the master shape. Alternatively, the container can have a first elastomeric membrane surface; a first port to deaerate the volume of particles; and a second port to infuse the volume with a liquid for mobilizing the volume of particles; and a press coupled to the container to move the master shape into the membrane to shape a reformable material into the object according to the master shape. The container can include a rigid outside frame and top and bottom elastomeric membranes facing the top and bottom surfaces of the container, and wherein the master shape is pressed against the top elastomeric membrane of the container by atmospheric pressure. The base station can also include a flexible vacuum cap sealed over the shape and against the container's top surface membrane; a third port to evacuate air from a space between the top membrane and the vacuum cap; and pressing of the particles within the container by atmospheric force acting in opposed directions against the vacuum cap and the bottom surface membrane. The master shape can be placed between an air-impermeable surface and the membrane of the container and a vacuum cap or a vacuum-bagging film can be placed over the container to form the elastomeric membrane against the master shape. The vacuum pump can be a mechanical pump or an air driven pump such as a Venturi pump. A second vacuum pump can be used. Isolating valves can be used, and a regulator and one or more valves can be used to pressurize a liquid tank. A vent valve can also be used to cycle from a vacuum source to a pressure source. A three-way valve can route air and vacuum to the liquid tank. A filter can be used to prevent particulate carryover. An air-liquid separator and/or a level indicator can also be used. A vacuum, pressure, liquid and temperature sensor can provide data to the controller for process control. A heat exchanger can be used to condense vapor. A slurry transfer tank can be connected to the container. The container can be a single unit, or can have a plurality of containers adjacent to or inside the container to form a cavity. The containers can be mated with a seal ring.

In yet another aspect, a method to shape a reformable material includes holding a volume of particles inside a container having a first elastomeric membrane surface; and infusing the volume of particles with a liquid; agitating the liquid to provide one or more surges of liquid to mobilize the volume of particles; and pressing a master shape into the membrane with atmospheric pressure.

Implementations of the above method may include one or more of the following. The method may provide locally distributed surges or globally distributed surges. The surges can exert differential liquid forces on particles to displace them relative to one another and facilitate their movement into a closely-packed volume. A differential pressure can be applied between a master shape side and a liquid-particle side of the membrane. The pressure between a vacuum cap and the membrane can be decreased to move the membrane in a first direction or increased to move the membrane in a second direction. The membrane is free to move relative to the master shape. Excess liquid can be removed to leave particles against the membrane. Air can be evacuated from space between the membranes. The particles can be packed against the membranes and the master shape. The liquid with the vacuum cap and membrane pressed against the master shape can pack the particles against the membranes and the master shape. The agitating operation can include pulsing or vibrating the liquid. The vibration frequency can be adjusted to displace one particle relative to another to keep the particles moving freely in relation to one another. The amplitude of the liquid pulsation can be proximally equal to a diameter of the particles. A first surge of liquid can be directed towards a desired transport direction and a second surge smaller than the first surge can be directed in an opposite direction to the transport direction. The agitating of the liquid can be used to minimize blockage. The method includes maintaining the volume of the container constant and completely filled to force the particles against the master shape. The method includes extracting transitional liquid from the container; and adding new liquid equal in volume to the transition liquid.

In yet another aspect, a shape-reformable composition includes a carrier medium having a carrier density; and a plurality of solid bodies having a density substantially similar to the carrier density, said solid bodies being transitionable from a formable state to a three dimensional solid shape. The bodies can have a density substantially lighter or heavier than that of the carrier if they have a high ratio of surface area to volume. The bodies can be stiff, flexible or elastomeric. The bodies can be regular or irregular and can be of substantially different types intermixed.

Implementations of the composition can include one or more of the following. The carrier medium fills voids or interstices between the solid bodies such that the voids or interstices are free of air or gas bubbles. The solid bodies can have near-liquid or fluent mobility during the formable state. The solid bodies can transition to the solid shape through an introduction and an extraction of a predetermined amount of the carrier medium. The solid bodies can be positioned in a container having a first elastomeric membrane surface. Liquid can be introduced to mobilize the volume of particles. A master shape can be pressed into the membrane with atmospheric pressure. The resulting solid shape is a stable, force-resisting shape. The solid bodies and carrier medium form a reversible state-changeable mixture. The carrier medium can be a liquid or a gaseous froth. The shape can be a reformable mold or a reusable template to capture dimensions of impressed shapes for transfer to a mold.

In other aspects, a system is disclosed for holding a volume of particulate material inside an air and liquid-impermeable container with at least one elastomeric membrane surface; deaerating the volume; infusing the volume with a liquid to cause it to be mobile; pressing a master shape into the membrane via atmospheric pressure; and extracting the liquid through one or more screen elements which are placed in or adjacent to the particle volume. The extraction causes atmospheric pressure to press the particles against the contours of the shape and against each other. This pressure continues to hold the particles in place against the elastomeric membrane when the master shape is removed from the outer surface of the membrane. The system further has a means to heat and drive liquid from the particle volume and, in certain embodiments, to leave a residue of binding adhesive which locks the particles into a continuous force-resisting mass.

Operation of one embodiment is as follows with a particular embodiment of the container which has a rigid outside frame and a membrane face on the top and bottom surfaces. With the particle volume infused by liquid, a master shape is pressed against the top elastomeric membrane of the container by atmospheric pressure, thereby causing the shape to impress a complementary shape in the membrane. This pressing is accomplished through use of a flexible or elastomeric vacuum cap which is sealed over the shape and against the container's top surface membrane, following which air is evacuated from between the top membrane and the vacuum cap. Liquid is then extracted from the volume and the particles within the container are pressed together by atmospheric force which acts on all exterior surfaces of the tool-bed but in particular in opposed directions against the vacuum cap and the bottom surface membrane. Air is then introduced into the vacuum cap, the cap removed and the master shape removed from the formed surface of the elastomeric membrane.

In another embodiment, the container is formed against a master shape with the process of liquid infusion, a pressing action via atmospheric pressure and a liquid extraction process. This embodiment is essentially a flat envelope with a flexible outside rim and two opposed elastomeric membranes. To use this embodiment a master shape is placed on an air-impermeable surface, a membrane of the container is placed over the shape, and either a vacuum cap or a vacuum-bagging film is placed over the container to effect forming of the elastomeric membrane against the master shape. The envelope may also have a vacuum seal on its perimeter and so has the combined function of containing a mass of particles and of serving to extract air from between the master shape and the envelope.

In implementations, there can also be a combined use of the first and second containers described above. A master shape may be placed on the top elastomeric surface of the first rigid-framed container and then a membrane surface of the second container is placed over the shape. The second container fits inside the frame of the first container and a vacuum cap is placed over and sealed outside the second container against the surface membrane of the first container. When the volume under the vacuum cap is evacuated the master shape is pressed between the elastomeric sides or faces of the two containers. Liquid is then extracted so that the two volumes of particles are pressed together and against the membranes surrounding the contained shape; the vacuum cap is vented with air and removed; the top container is removed; and the shape is removed from the membrane of the bottom container. When the top container is again placed over the bottom container, a closed, shaped cavity is formed which is complementary to the entire surface of the master shape which was used to form the cavity.

In yet another embodiment, a combination of containers can be used in which two identical containers of either the first or the second type may be pressed together around a master shape without use of the vacuum cap. In this case the containers are joined and sealed by either a seal mounted on one or both of the containers or by seals mounted on a seal ring which fits between the two containers. The seal ring may be further employed to channel vacuum or air pressure between the two containers and to hold the master shape in a precise orientation and position between the two opposed containers. The seal ring may also furnish access to the formed cavity for the purpose of injecting a moldable material into the cavity.

In yet another embodiment of the container the container itself is formed into a replica of a master shape, or into a shape complimentary to a master cavity by another combination of the elements and processes described above. The exterior of this third type of container may be formed entirely from an elastomeric material or may be formed from a combination of elastomeric, flexible and rigid materials. Though the container might be shaped against a single surface, it can also be shaped over substantially its entire surface by confining it within a master cavity formed by two or more closely-fitting mold parts. Key to this forming process is an expansion means within the third container which presses the particulate material against the cavity walls.

In another embodiment, there is combined use of the containers which employ the three types of containers described above for a single purpose. The first or second types can be used to form a complementary cavity from a master shape. The third type of container can then be placed in the cavity, which is now used as a master cavity, and the third type formed complementary to the master cavity contours, thereby creating a replica of the original master shape.

It can be appreciated that there are numerous variations of containers and varied combinations of containers which can be employed either to form a surface which is complementary to the exterior surface of a master shape in part or in whole, or to form a surface or surfaces complementary to the interior contours of a hollow master shape or master cavity. For instance more than one container of the first type (rigid frame) or second type (flexible-edge) can be employed to form a continuous surface complementary to a master shape's surface, with the elastomeric membranes of the containers either overlapping or being abutted together. Containers of the second type may also have a membrane and particle configuration that allows two or more of the containers to be "tiled" together to form a continuous surface of particle-backed membranes. Likewise two or more containers of the third type can be employed together to form a shape complementary to the interior of a master cavity.

In yet other embodiments, a forming system also includes a base station which provides evacuation of air, liquid infusion into and liquid extraction from the particle filled containers. The base station also furnishes vacuum forces to enable the forming operations to be performed on the various containers either singly or in combination. The base station comprises a liquid receiver; onboard vacuum system or provision to connect to an external vacuum source; an air compressor or provision for external connection to pressurized air; valves, fittings and tubing or piping to provide vacuum and to control the flow of liquids to and from the containers; an electrical power supply to operate the valves, process sensors and any onboard mechanical vacuum pumps and air compressors; and a menu-driven process controller to operate the base station.

In another embodiment, a forming system includes a heater which may be used to vaporize and drive out liquid from the particle filled containers, and further to heat any materials which may be used to recreate the contours of the original master shape through molding against the complementary surface of the formed elastomeric membrane. The vaporizing or drying process is especially advantageous when the liquid contains a soluble binder which remains on the pressed-together particles and locks the shaped volume of particles in place when the liquid has been driven out of the container. The heater may take numerous forms to include a radiant heater, a convective air heater, heating elements within the particle-filled container, and various types of inductive (e.g., microwave or radio-frequency) heaters. The heater may be powered and controlled by the base station and its controller, or the heater may be powered and controlled separately.

Next a reformable shoe making embodiment is detailed. In this system, the 3D model of the shoe as customized by the user or a doctor for the user is sent 1003 is provided to a reformable shape object fabricator 1006, which is detailed next. The fabricator 1006 renders a physical model of the 3D model and then applies a state-changeable mixture that includes uniform, generally ordered, closely-spaced solid bodies and a liquid carrier medium, with the liquid filling any voids or interstices between the bodies and excluding air or gas bubbles from the mixture. Within the mixture, the solid bodies can be caused to transition from a near-liquid or fluent condition of mobility to a stable, force-resisting condition. To create mobility, a small excess quantity or transition liquid is introduced to create a fluent condition by providing a slight clearance between the bodies which permits the gently-forced introduction of at least two simultaneous slip planes between ordered bulk masses of the bodies at any point in the mixture. Transition to the stable condition is caused by extraction of the transition liquid, removing the clearance between bodies and causing them to make stable, consolidated contact. FIG. 4A shows a computer controlled system for fabricating parts that whose dimensions are specified in a data file and rendered by a CAD/CAM software such as Solidworks or Autocad or even Paint, and the object described in the data file needs to be fabricated. Conventional printers print a layer at a time and can take significant time in making a single product. To accelerate the production process, the system of FIG. 4A takes 3D data from a computer with 3D CAD design 1002 and provides the information to an actuated 3D shape generator 1004 that is placed inside of a reformable object copier 1006. The 3D shape generator 1004 forms the 3D object, and the object copier 1006 reproduces copies of the formed 3D object in minutes, thus greatly accelerating production of mass-customized products which otherwise takes hours on a 3D printer.

The 3D shape generator 1004 is a complete computer actuated system that is enclosed in the object fabricator 1006. CAD data is downloaded by wire or wireless connection to the shape generator 1004. Based on the desired dimensions, one embodiment of the 3D shape generator 1004 forms a 3D object by having an array of computer controlled moveable pins whose height is adjusted in accordance with the CAD design file, and the overall shape is smoothed by a Lycra sheet or felt sheet. The pins or rods lift the felt or Lycra sheet to form a 3D object based on the CAD design file. In this embodiment, an array of N×N micro hydraulic actuators can be used to form the shape. This embodiment is a dense hydraulic planar pin-rod matrix array. Another embodiment actuates an N×N pin-rod matrix driven by servomotors. In either case, each pin-rod is controlled individually, similar to pixels on a screen except that the pixel has height as well.

In one embodiment, the N×N matrix can be an array of electro-mechanical pins positioned in a frame. The frame is adapted to hold the plurality of pins in a parallel position to one another in a series of columns and rows, such that the distal ends of the plurality of pins together form a flat virtual plane. Each pin of the plurality of pins includes an elongated housing member defining a linear axis therethrough, and a pin member adapted to slide linearly in either direction along the axis. Each of the housing member includes an upper electromagnet, and a lower electromagnet separated from the upper electromagnet. Each of the electromagnet is adapted to move its respective pin member linearly in either direction. Each of the pin member includes a linear potentiometer, a, magnet and an electronic transmitter attached to an opposite end to the distal end, such that when each of the pin members are moved linearly each respective linear potentiometer sends a signal to its respective transmitter which in turn sends an electronic signal describing its movement within its respective housing member, a plurality of electronic wires respectively connected to each transmitter, such that electronic signals can be relayed to and from each respective pin; an analog-digital converter connected to the plurality of electronic wires and adapted to convert the analog electronic signals relayed by the transmitters into digital format to be transmitted, processed, stored, and then converted back into analog form for return transmittal to the set of pins. A processor is connected to the converter and adapted to retrieve the electronic signals from the converter, store them, and retransmit them back to the converter when desired, such that a user can displace the pin members from the virtual plane in any pattern, have electronic signals sent, processed, stored, and returned to the same set of pins, or another separate set of pins, at a later time to thereby displace the pins to the same positions as the original pattern chosen by the user.

In one embodiment, the pin array device has each of the housing member of each pin comprise an upper frame upper electromagnet, upper spring, lower electromagnet, lower spring and shield along the entire upper frame wall to separate magnetic field between each interactive pin. The lower frame consists of the outer fixed part of the potentiometer and electronic transmission from electronic transmitter to both electromagnets. The pin consists of a magnet, a mobile portion of the potentiometer, electronic transmitter that picks up all the wire and sends position signal and feeds the power to both electromagnets via the lower housing. The electronic signal may be a Pulse Width Modulation signal, and the displacement of each of the pin members is proportional to the strength of the Pulse Width Modulation signal received by the electromagnets.

Figure 14A:
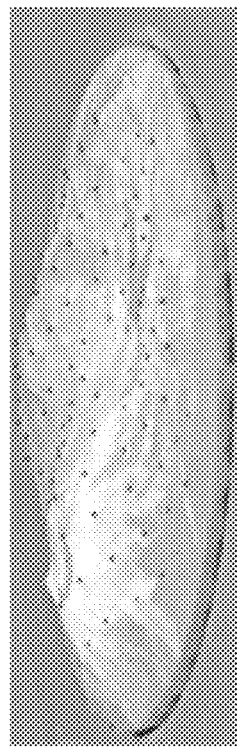
FIGS. 14A-14D show exemplary systems and techniques for manufacturing in volume with a wide range of materials are disclosed for fabricating custom protective gears, helmets, pads, or shoes at mass customization scale.
Figure 14C:
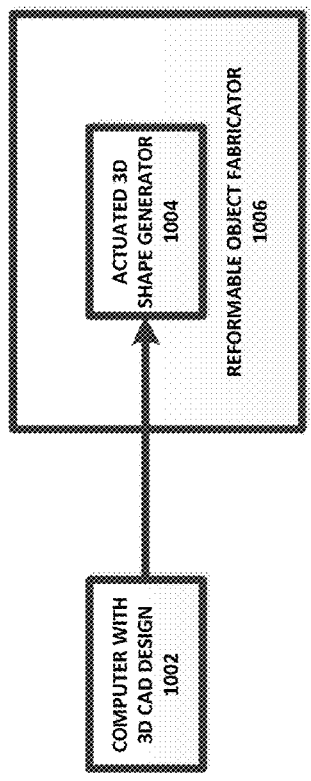
Figure 14B:
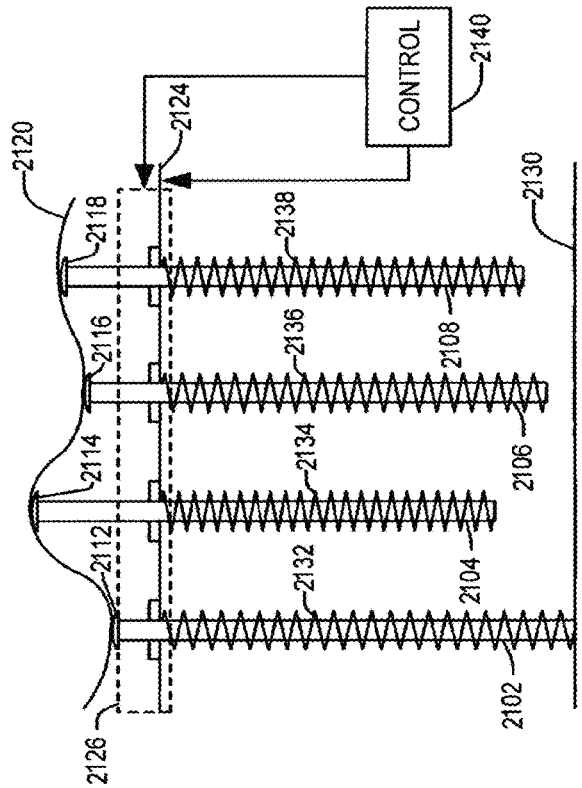

FIG. 14B shows the shape of the object when a felt cover or a Lycra cover is placed above the pins to form a 3D structure that can be digitally controlled using a CAD output to form a 3D object that can then be copied or fabricated using the reformable object fabricator 1006.

In yet another embodiment shown in FIGS. 2C-2D, the pins are moved by the action of a plate, common to all or a portion of the pins, that can extend and retract along a single axis of motion. A clutch mechanism cooperates with the moving plate to fix the pins at a desired position. In an exemplary embodiment, the shape generator 1004 can include a membrane covering the pins. A plurality of pins 1011-1018 arranged in an array such that respective head portions 1021-1028 associated with the pins collectively define a surface 1030. It will be appreciated that the area of array is not necessarily defined by two Cartesian dimensions. For example, the pins could be arranged along a spherical or hemispherical surface, with the array spanning the azimuthal and polar dimensions across the surface of the sphere. The position of a given pin (e.g., 1011) can be adjusted along an axis of motion.

In one embodiment, an optional motion plate 1032 can be provided to move the pins along the axis of motion as to adjust the position of the pins. The motion plate 1032 can be moved by reasonable mechanical or electromagnetic means. For example, the plate 1032 can be moved via an electrical motor, a hydraulic assembly, or one or more solenoid coils exerting a magnetic force.

A clutch mechanism 1034 is operative to arrest the motion of a given pin at a desired position. The respective positions of the pins can be selected to deform the display surface into a desired raised image. The clutch mechanism can comprise reasonable means for selectively arresting the motion of the pins. For example, the clutch mechanism 1034 can comprise components for mechanically or magnetically engaging the pins.

One embodiment provides an upper plate with a plurality of apertures through which corresponding pins forming the object's surface can pass. The pins can include head portions with areas larger than that of their respective apertures, to more fully tessellate the display surface and to help maintain the pins within the apertures. The upper plate can house part or all of a clutch mechanism that selectively engages one or more pins to maintain the pins at a desired position. The upper plate houses one or more banks of solenoids that shift the position of one or more portions of the clutch (not shown) that physically communicate with the pins. In an exemplary embodiment, the solenoids shift the position of one or more bars such that they contact or release circumferential grooves on the surface of the pins. This embodiment also provides a lower plate and a base plate disposed parallel to the upper plate along one or more support posts. A lifting plate can be suspended between the lower plate and the base plate on one or more guide posts. The lifting plate can be raised or lowered via a motor and belt system to adjust the position of the pins. For example, the pins can be reset to a fully raised position by raising the lifting plate to its maximum height. The movement of the guide pins and the action of the clutch mechanism can be regulated by a processor.

Figure 14D:
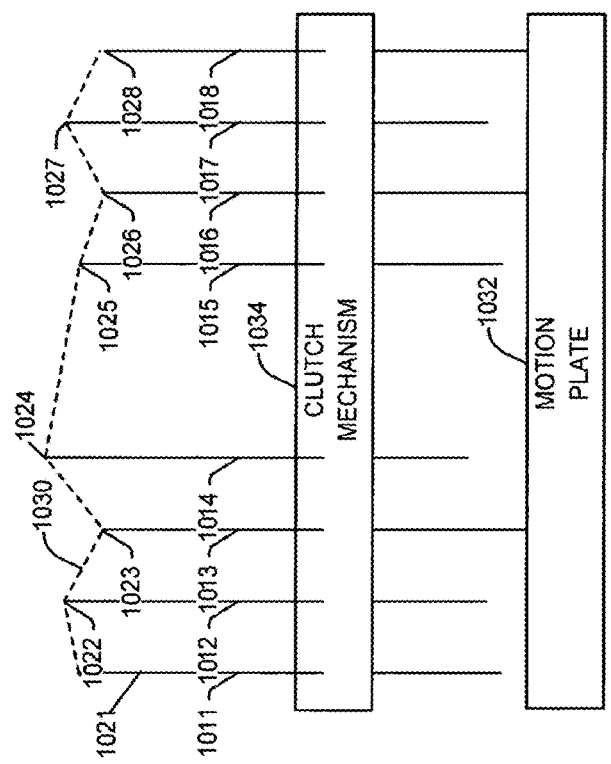

FIG. 14D illustrates a side view of an exemplary computer shaped object that can be reproduced or fabricated formed in accordance with an aspect of the present system. As shown in FIG. 2E, two facing and opposite bed of pins 2210-2212 can form a 3D shape for the sole or insert. The insert and/or the shoe can be produced in discrete sizes such as US sizes 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, and 18, for example. Thus, a plurality of sized beds can be used, or one large pair of beds covering size 20 can be used to produce all other smaller sizes. Turning back to FIG. 2D showing one of the beds 2210-2212, the selected view of the 3D object creator comprises one row of four pins 2102-2108. It will be appreciated that a functioning computer controlled 3D object creator can contain a large number of pins arranged across multiple rows in order to reproduce the shape of the 3D object with high fidelity.

In an exemplary embodiment, the rows containing the pins 2102-2108 are staggered as to form a honeycomb pattern. Accordingly, the pins 2102-2108 are arranged in a plurality of linear rows and one or more staggered columns. Alternatively, the pins can be arranged in a Cartesian grid, such that both the rows and the columns are linear. It will be appreciated that other methods of arranging the pins can be utilized, and that the placement of the pins will vary with the necessary size and spacing of the pins, as well as the desired shape (e.g., flat, spherical, recessed) of the array.

In the illustrated display, the pins 2102-2108 have respective cap portions 2112-2118 that define a raised surface. The cap portions 2112-2118 can be covered by an elastic membrane or felt layer 2120 to provide a relatively smooth surface for the object. The use of the pin caps 2112-2118 and the membrane 2120 will depend on the application. The pins 2102-2108 pass through respective apertures in a stationary, outer plate 2124. The outer plate 2124 houses a clutch mechanism 2126 that acts to maintain the pins in their desired positions. In an exemplary implementation, the clutch mechanism 2126 can comprise a series of row bars and column bars having two associated positions. In a first, open, position, a given bar allows the pins within its associated row or column to move freely. In a second, restraining, position, the bar is moved to physically contact the pins at one of a plurality of evenly spaced grooves on the pin, maintaining the pin at its position. The spacing of the grooves corresponds to a desired resolution of the display 2100. The position of the bars can be changed via one or more banks of solenoids. In an exemplary embodiment, the bars are biased, by a spring or similar mechanism, to remain in the restraining position, until a solenoid is actuated to move the bar into an open position.

During operation, the pins can be reset into a fully extended position by a reset plate 2130. The reset plate 2130 can then be incrementally withdrawn to allow the pins 2102-2108 to retract toward the interior of the display device. In an exemplary embodiment, the reset plate 2130 is moved by a motor and belt arrangement. The pins 2102-108 have associated springs 2132-2138, with each spring (e.g., 2132) attached at a first end to the underside of the outer plate 2124 and at a second end to the end of the pin (e.g., 2102) opposite the cap portion (e.g., 2112). When the pins 2102-2108 are fully extended, the springs 2132-2138 are compressed against the underside of the outer plate 2124. The springs 2132-2138 thus provide a tensive force on the pins 2102-2108 as to draw the pins toward the interior of the object being formed.

The movement of the reset plate 2130 and the operation of the clutch mechanism can be coordinated by a controller 2140 to adjust the position of the pins 2102-2108. The controller 2140 can provide information relating to the desired pin positions to the projector. The reset plate 130 can be incrementally withdrawn toward the interior of the object. In an exemplary embodiment, the reset plate 2130 withdraws in increments equal to the spacing between the grooves on the pins 2102-2108. After each retraction of the plate, the clutch mechanism 2126 can be selectively activated to release one or more of the pins, while leaving others secured. The tensive force provided by the springs 2132-2138 pulls the ends of the released pins flush against the reset plate 130, such that the released pins retract to a uniform level defined by the position of the reset plate. The secured pins remain at their previous level. The pins are then resecured by the clutch mechanism, and the plate is retracted by another increment. This process is repeated as the reset plate 2130 retracts to leave each pin at a desired level of extension.

In another embodiment, the pins pass through respective apertures in a stationary, outer plate housing a first portion of a clutch mechanism that acts to adjust the pins into desired positions. In an exemplary implementation, the first clutch portion can be piezoelectric restraints for the plurality of pins. In a default position, a given restraint loops around its associated pin, but allows the pin to move freely. Upon the application of an electrical current, the restraint contracts as to physically contact its associated pin at one of a plurality of evenly spaced grooves on the pin. This fixes the pin to the outer plate, maintaining the pin at a stationary position. The spacing of the grooves corresponds to a desired resolution of the 3D object being formed. The pins also pass through respective apertures in a moving plate which can be moved by a motor and belt arrangement. The moving plate houses a second portion of the clutch mechanism with piezoelectric restraints for the plurality of pins. The movement of the moving plate and the operation of the first/second clutch portions can be coordinated by a controller to adjust the position of the pins. The moving plate oscillates in a direction normal to the outer plate and a base plate between a first position, closest to the base plate and a second position, closest to the outer plate. In an exemplary embodiment, the first position and the second position are separated by a distance equal to the spacing between adjacent grooves. The pins begin in a default position, fixed to the outer plate by the first clutch portion. In an exemplary embodiment, the default position of the pins is a fully withdrawn position (e.g., the first clutch portion engages the uppermost groove of each pin). Since the default position of the pins is known, the controller can determine the distance between the default position and a desired position as a number of increments, as defined by the groove spacing of the pins. The controller can thus select one or more pins to extend by one or more increments. While the moving plate is in its first position, the selected pins are released by the first clutch portion. Simultaneously, the second clutch portion engages the selected pins, such that the pins are fixed to the moving plate. The moving plate can then be moved to its second position. Once the plate reaches the second position, the second clutch portion releases the selected pins, while the first clutch portion reengages the pins. It will be appreciated that the motion of the moving plate can be controlled by the controller such that the first clutch portion can engage the pins at a groove one increment below the default position. Accordingly, the selected pins are extended by one increment. This can be repeated a number of times, to allow one or more pins to be moved to a desired position up to a maximum extension. The final position of each pin will be determined by the number of times the first and second clutch portions are activated for the pin. This can be controlled by the controller according to the desired position of the pin. Once the pins have been positioned, the controller can direct the object fabricator 1006 to copy the 3D object formed by the pin grid 3D shape generator.

In another exemplary clutch mechanism, a pin can be encased in a solid restraining material having a low melting point. For example, the restraining material can be an alloy of lead and one or more other metals. The restraining material is contained in a container having a relatively high melting point. The clutch mechanism disengages by applying heat from a heat source to the restraining material in order to bring it to a liquid state. The heat source can be applied by a laser apparatus (not shown) directed on the restraining material or by a heating element associated with the container. In an exemplary implementation, the container is the heat source, producing resistive heat upon the application of an electrical current. While the restraining material is in a liquid state, the pin can move freely through the aperture. Once the heat source is deactivated, the restraining material cools and returns to a solid state, restraining the pin.

In yet another exemplary clutch mechanism, a wire has shape memory properties is looped around a pin. The material with shape memory properties has the ability to return to an imprinted shape when heated. A desired shape can be imprinted into the material by molding the material at a high temperature and maintaining the desired shape as it cools. Below a threshold temperature, the material is relatively flexible and can be deformed away from the imprinted shape with relative ease. Once the material is heated above the threshold temperature, however, it reverts back to the imprinted shape with some force. In an exemplary implementation, the wire is a formed from nitinol, an alloy of nickel and titanium. The wire is shaped such that the loop is opened around the pin and the pin can move freely through the loop. A current can be applied to the wire to heat the wire via resistive heating to a temperature greater than its threshold temperature. This causes the wire to return to its imprinted shape, engaging the pin as the loop closes. The wire returns to its imprinted shape somewhat forcefully, such that the tensive force on the ends of the wire is insufficient to restrain it. In an exemplary embodiment, the wire is looped around a groove in the surface of the pin to facilitate engagement of the pin. When the current is no longer applied, the wire 352 cools and returns to its more malleable state. Once the wire cools below threshold, the tensive force applied can once again deform the wire into an open shape, releasing the pin.

Form and Operation of Particle-Filled Containers

FIGS. 13A-D show a first container embodiment, a master shape and a vacuum cap, and further show a sequence of operations to create a shaped impression, complementary to the master shape, in the surface of one elastomeric membrane face of the container. Turning now to FIG. 3A, a container 5 is shown with a rigid container frame 10 and elastomeric top and bottom membranes 20 and 25, resting on a base 13 which separates the bottom membrane 25 from contact with any surface that the base 13 and the container 5 rest on. The top membrane 20 is bonded to a perimeter frame 17 so as to have an air-tight interface between the container frame 10 and the membrane 20. The container frame 10 is affixed to a continuous vacuum-activated seal 30 which is bonded to the container frame 10. The seal 30 is resilient and acts much like a suction cup to hold the perimeter frame 17 to the container frame 10. The bottom membrane 25 is bonded directly to rigid container frame 10 since the membrane 25 is not a working surface wearer to damage, in contrast to the working surface of membrane 20 which is subject to damage. In one embodiment, the bottom membrane 25 can be affixed by a perimeter frame and vacuum seal as described above. In yet another embodiment with more complexity, mechanical clamps and a pressure seal can be employed to affix either top or bottom membranes. Tubes 40, 50 and 60 penetrate a toolbed or a container frame 10. The tube 40 communicates with a seal 30 through an opening 45, and the seal 30 affixes the membrane 20 to the container 5 by a vacuum (indicated by arrow 43) acting through the tube 40. The vacuum seal 30 can be inactivated by introducing air through the tube 40, allowing the membrane 20 and the frame 10 to be removed in order to insert or remove a volume of particles from the container 5, or to replace a damaged membrane 20 or internal screen element. The tube 50 communicates with a main particle screen 55 which is overlaid with a volume of particles 80. Arrow 53 indicates the flow of liquid into the particle volume through screens 55. The particle screens 55 serve to hold all particles in the container 5 while allowing liquid to flow in and out of the particle mass. There is a double layer construction of both screens 55 with the tubes 50 and 60 communicating between the layers. The particles cannot penetrate the outer layers of the screens and so do not move into the tubes as air is evacuated or liquid extracted. Detail 57 of FIG. 7B-1 shows extensions of tubing 50 penetrating into the center of the double-layered screens. The extensions have perforations that enable distributed liquid flow along the length of the tube inside the screen. The tube 60 communicates with a rim evacuation screen element 65 which follows the entire inside upper perimeter of frame 10 and is likewise perforated along its length within element 65. Arrow 63 points outward to indicate deaerating vacuum force acting on the container volume via the evacuation element.

Figure 13A:
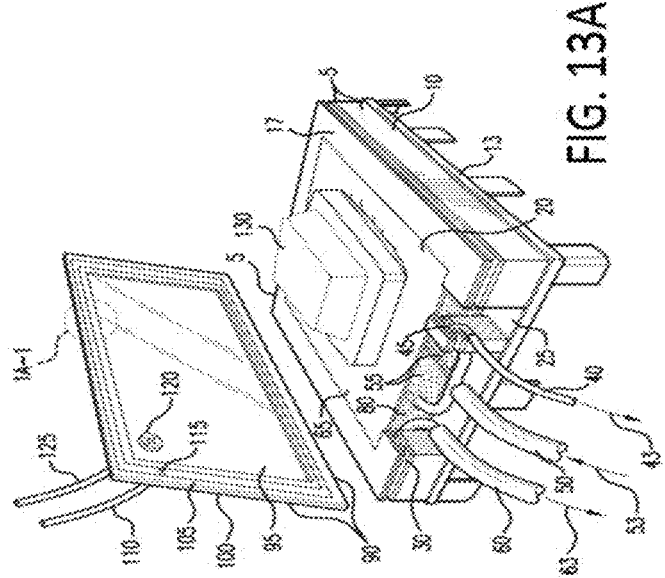
FIGS. 13A-13D show exemplary 3D fabricator of gears.
Figure 13B:
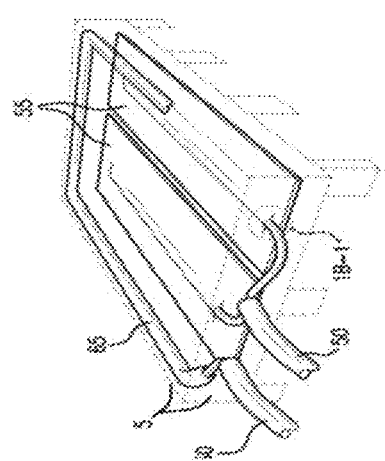

Turning now to the top of FIG. 13A, a vacuum cap 90 is shown with a continuous flexible or elastomeric membrane 95 bonded to another perimeter frame 100, the frame also having a continuous vacuum-activated seal 105 bonded to the frame 100. The seal 105 is identical in design and function to the seal 30. The vacuum cap 90 has a tube 110, which communicates with the vacuum seal through an opening 115, and a tube 125 which in turn communicates with the underside of membrane 95 through a port 120.

A master shape 130 is shown resting on membrane 20. The master shape will used to form a shaped impression in the membrane as described next. To prepare for the forming process, a membrane 20 is sealed to the container; air is removed from the volume of particles as shown by arrow 63; and liquid is introduced into the particle volume as shown by arrow 53. Liquid flow is cut off when there is sufficient liquid to allow particles to move in relation to adjacent particles as displacing force is exerted on either the top or bottom membrane of the container.

Figure 13C:
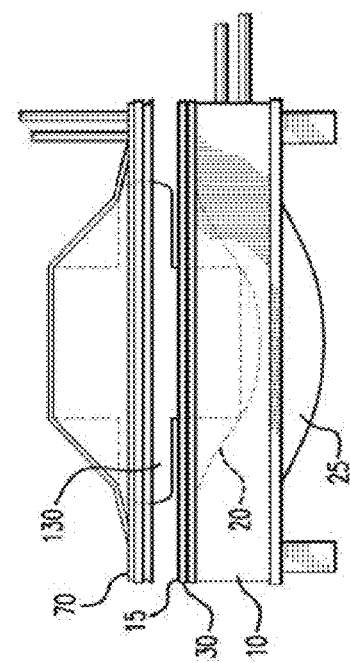

FIG. 13C shows a side view of the container frame 10 with a vacuum cap 70 resting over the master shape 130 prior to being sealed against the membrane perimeter frame 15 to which the membrane 20 is bonded, with the membrane affixed using the seal 30 to the container frame 10. The master 130 is resting on the unformed surface of membrane 20 with the movable particles between membranes 20 and 25.

Figure 13D:
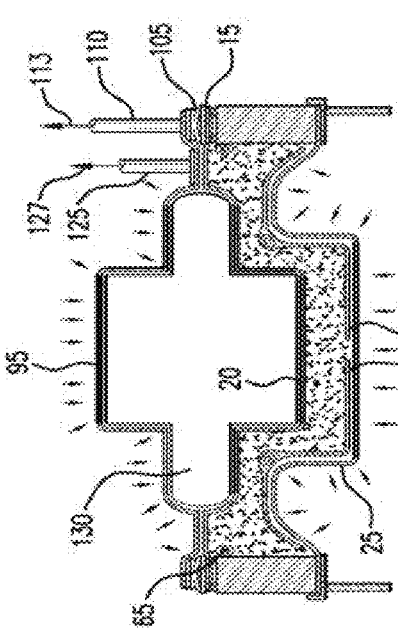

FIG. 13D shows a cutaway view with the vacuum cap 90 affixed by the seal 105 against the perimeter frame 15 by vacuum through the tube 110 as shown by an arrow 113. In addition the space between the vacuum cap membrane 95 and the top membrane 20 has been evacuated through the tube 125 as shown by an arrow 127. The vacuum cap membrane 95 is pressed down against the master shape 130 and against the surface membrane 20 by atmospheric pressure which also acts opposedly against container bottom membrane 25. Liquid is then extracted by a pump or vacuum from the particle volume through a tube (not shown) through the particle screen 55, causing atmospheric forces acting on bottom membrane 25 to pack the particles against top membrane 20 which is forced against the master shape since air has been evacuated from between the vacuum cap membrane and top membrane 20. Any leakage of air into the container, which would add atmospheric pressure back to the container and so reduce the packing force on the particles, can be removed by continuing vacuum extraction of liquid through particle screens 55 or by vacuum extraction through the perimeter evacuation screen element 65.

When the master shape 130 is removed from the surface of the membrane 20, an impressed shape 135 remains which is complementary to the shape 130. The differential pressure on the container by vacuum extraction is continued, thereby maintaining opposed atmospheric forces that act to keep membranes 20 and 25 pressed against the particles and so immobilizing them to keep the impressed shape stabilized. In form the seal is a continuous channel with the legs angled outward. The channel has a single opening and a vacuum and vent tube connected to it as described with reference to FIG. 3A. The material of the seal is resilient since the legs will be pressed against a surface and must conform to and seal against the surface. The legs are separated by a sufficient distance that they will be pressed into contact with the surface by atmospheric pressure with a greater force per unit area than atmospheric pressure. In function, when the legs of the channel are pressed against a smooth surface and the vacuum introduced inside the channel, the seal legs deform against the surface and the deformed area is substantially less than the area inside the channel. In experiments a ratio of deformed area to inside area of 1 to 2 has been shown to be very effective in sealing against a smooth surface if the durometer of the seal's elastomeric material is around 40. In operation the seal is simply placed against or gently pressed against a smooth air-impermeable surface. A vacuum is introduced through the tube, extracting air from within the seal and so enabling atmospheric pressure to force the seal against the surface. Any leakage from atmosphere outside the seal is scavenged by the vacuum and so does not enter the volume inside the perimeter of the seal even if a full vacuum is imposed on that volume. To release the seal air is introduced via the tube or a small blade can be slipped between the seal and surface to break the internal vacuum.

The particles can be a reversible state-changeable mixture having a plurality of solid bodies and a carrier medium, with the carrier medium filling any voids or interstices between the bodies. Within the mixture, the solid bodies can be caused to transition from a formable state, preferably a near-liquid or fluent condition of mobility, to a stable, force-resisting condition through introduction and then extraction of a slight excess quantity of the carrier medium beyond that required to fill the interstices of the bodies when closely packed. In most embodiments, the carrier medium is a liquid preferably excluding any air or other gases from the mixture, and most of the discussion will revolve around such embodiments. However, some embodiments use a carrier medium that is a liquid-gas froth.

The mixture can be rapidly shifted from a formable (preferably near-liquid or fluent) state to a stable force-resisting state and back again to the formable state, through slightly altering the carrier-solid proportions of the mixture, and the system further provides methods and apparatus for using the mixture. Embodiments are characterized by one or more of the following advantages: the ability to pressurize a mixture and drive it against a complex surface as if it were a liquid; the ability to create a "near-net" or extremely accurate representation of a shape due to the negligible volumetric change that accompanies a state change; the ability to effect the state-change with a very small volume of single-constituent transfer and with consequently small actuation devices without the need for a vacuum pump, without chemical reactions, and with no need for thermal or electrical energy to be applied to the mixture; the ability to greatly alter the volume of any elastic or otherwise dimensionally changeable container, envelope or chamber through the free-flowing transfer of the mixture from one container to another; and the ability to tailor the mixture to satisfy a wide variety of physical specifications in either the flowable or the stable state.

The mixture can be used in reformable molds or other shaping tools, and in reusable templates that capture the dimensions of impressed shapes for transfer to a mold. The mixture can also be used in any product or shape that benefits from the incorporation of arbitrary reformability or precise reconfigurability. The mixtures further provide useful properties for use in a wide range of shock-absorbing, leveling, protective and supportive elements or apparatus.

The mixture in its formable state may be loosely compared to quicksand, while the mixture in its stable state may resemble hard-packed sand or even cement, with the transition being caused by the transfer of a relatively small amount of liquid. Hence the mixture, while in the formable state, includes enough liquid to fill the interstices between the nested solid bodies, and an excess amount of liquid that is referred to as the transition liquid. In the stable state the transition liquid is absent and the bodies are completely packed or nested.

In preferred embodiments the solid bodies are uniform, generally ordered, and closely spaced, with the predominate mass of the bodies close-packed and touching. To create mobility, the transition liquid is introduced in just-sufficient quantity to create a fluent condition by providing a clearance between some of the bodies, which clearance permits the introduction of at least two simultaneous slip planes between ordered masses of the bodies at any point in the mixture. The bodies themselves separate freely from one another under movement of the liquid and without turbulent mixing, and shift relative to one another generally in ordered bulk masses. The bodies should be of a density that is close enough to that of the liquid to permit flow of the bodies along with the liquid, or should have a size or structure that facilitates movement of the bodies along with the liquid.

In an embodiment, the surface of the mixture while in the formable state is first made to conform to a desired shape. The bodies in the mixture are then caused to transition from the fluent condition to the stable condition through extraction of the transition liquid. This extraction removes the clearances required to provide slip-planes between ordered masses of the solid bodies, thereby causing the bodies to make nested, packed, interlocking or otherwise stable consolidated contact. The mixture, now in the stable state, has a surface that conforms to the desired shape.

The mixture can be used in molds, templates or other products through holding the mixture in, or transferring quantities of the mixture while in the fluent condition into and out of variable-contour or variable-volume containers or chambers. The mixture can be stabilized by removal of the transition liquid, which may cause an elastic membrane to be pushed against the consolidated bodies by ambient pressure, or by transition liquid removal that causes the solid bodies to pack together under liquid tensile forces, thereby creating an ordered, deformation-resisting structure through surface friction or through surface adhesion of one body to another.

In certain embodiments, the mixture can be held inside a container or transported into a container with a flexible, elastically deformable and stretchable wall. The process then extracts the transition liquid from the mixture so as to cause body-to-body contact and force-resisting stability through pressure external to the container acting on the confined, ordered, abutting bodies. Transfer of fluent mixture into and out of the containers, or displacement of mixture within the containers can be accomplished by pressure forces within the mixture, with these forces being distributed uniformly throughout the mixture by the liquid carrier medium.

This distribution of uniform pressure against the surface of each body, coupled with the clearance volume furnished by the transition liquid, assures that the bodies are not forced against one another while the mixture is in the fluent condition. This elimination of body-to-body compression forces in turn prevents the bodies from sticking together and resisting displacement while the mixture is in the fluent condition. Pressure forces in the liquid can be exerted through pressing a shape against an elastic, stretchable membrane that constitutes at least one surface of a chamber substantially filled with the fluent mixture, or such forces within the liquid medium of the fluent mixture may be induced by a two-way pump or other transfer system.

The bodies themselves may have various geometries and may be provided within a state-change mixture in one uniform type, or there may be two or more types or sizes of bodies dispersed or layered within a mixture. For example spherical bodies of one size might have smaller bodies filling the interstices between the larger bodies, or a layer of short fiber bodies might float above a layer of spherical bodies. Flake-like bodies can be also be used, in which case the flat faces of the bodies can be pressed against one another to create a force-resisting body mass. The flat faces provide many times the contact area of abutting spheres, with accordingly higher friction or adhesion potential when consolidated against one another. If the flakes are in the form of a laminate that has one side heavier than the carrier medium and one side lighter, and if the flakes are closely spaced and in a medium which suppresses turbulence and solid body tumbling, the bodies will tend to be supported in, and to be consolidated in, an ordered parallel configuration. In this case, as with the spherical bodies, the transition liquid quantity will be just sufficient to create shear motion of body masses under low displacement forces.

Mixtures with more than one type or size of body can be used with the bodies either intermingled or layered separately, as by differing densities or the inability of bodies of one layer to pass through bodies in the adjacent layer. Bodies of different sizes or types may also be separated from one another by flexible or extensible porous materials or fabrications that allow passage of liquids but not of the confined bodies.

The degree of accuracy or irregularity on the surface of a stabilized mass of the mixture is dependent upon the relationship between the fineness of the bodies and the dimensions to be captured, a covering membrane's thickness and conformability, and the size and degree of regular packing order of a state-change mixture's solid bodies. If the bodies are very small compared to the contours of a shape that is to be replicated, or if the interstices between larger bodies in the mixture are filled by such smaller bodies, the mobile solid bodies of the mixture will consolidate and assume a near-net shape relative to any impressed shape when the transition liquid is extracted from the mixture.

In additional embodiments, the mixtures are stored external to one or more molds, tools or fixtures, and are selectively introduced, stabilized and made fluent again in the tools. Formulas of the mixtures or solid bodies and liquids of the mixtures may be stored separately, and may be mixed or separated as required for effective operation of separate elements of a forming or tooling system.

In yet other embodiments, flexible elements containing state-change mixtures are used to capture exterior or interior contours of a shape and to transfer the contours to other state-change elements. Through such "templating" operations a negative of a shape or surface may be produced and then a shape or surface identical to the first may be produced by forming the surface of a mixture against the transfer template. Individual elements might also be used to transfer portions of one shape to another shape and so create variations that combine the contours of two or more shapes into a single shape.

In still other embodiments, several elastic, extensible elements filled with state-change mixtures slide freely upon one another and relative to the contained mixtures in order to conform to highly contoured shapes. These embodiments would be used when the elastic stretch of a single membrane element is not sufficient to capture details of a shape.

Further embodiments include methods of displacing fluent mixtures within variable-volume flat elastic envelopes by pressing the envelopes against shapes with exterior air or liquid pressures, or pressing with physical elements such as bundles of rods or fingers that slide relative to one another. The pressing force pressurizes the liquid carrier medium and causes the envelopes to extend and conform to the shapes as the contained fluent mixtures flow within the envelopes under the uniformly distributed pressure forces within the liquid. Embodiments also contemplate the creation of hollow voids within a mixture-containing envelope, with the impressed shape causing the collapse of the voids so that the mixture need not be pumped into and out of a chamber to permit capture of a shape.

Yet other embodiments include methods for creating a sculptable condition in specific state-change mixtures through placing the mixtures in a quasi-stable state. The solid bodies are held in contact by extraction of a portion of the transition liquid, yet have sufficient lubricity or low contact friction to be displaced relative to one another by externally imposed forces. The bodies can be displaced into voids created within a mass of the quasi-consolidated mixture, or can be progressively displaced along the surface of the mixture from one region of the mass to another. In some embodiments, properties of flow of the mixture and the resistance to deformation of the abutted bodies are predetermined so as to be a function of the imposed external forces, and so to be subject to variable control that allows intermediate quasi-stable, sculptable or displaceable conditions within or on the surface of the bulk mixture.

State-change mixtures may also use solid bodies along with a state-changeable liquid carrier medium. The method for changing the mixture from fluent to stable and back again is, as described above, through transfer of a small amount of excess liquid; however, the mixture can be further solidified by changing the state of the carrier medium from liquid to solid.

In yet another embodiment, a state-change mixture is consolidated within a mold chamber and the liquid carrier or a second liquid component is circulated while held to a pressure below ambient. Through heating and cooling of the circulating liquid, the mold itself can be heated or cooled.

Still another embodiment of the state-change mixture has solid bodies that are hollow and very light, and a carrier medium comprising a liquid-gas froth of similar density. The froth is destroyed when extracted since the gas within it expands and separates from the liquid component; then the froth is reconstituted from the liquid and gas and reintroduced into the body mass to recreate a fluent mixture. The liquid component of the froth may be a solvatable (solvent-releasable) adhesive that can be dried to hold the consolidated bodies together and then re-dissolved by the frothed carrier medium. Very light bodies can also surrounded by a denser liquid, with the mixture likewise becoming fluent and then stabilized with transfer of a small quantity of transition liquid; however, the tendency of the bodies to adhere together under contact pressure is preferably countered, or liquid-like transfer of the mixture, especially through small lines or passages, becomes difficult if not impossible.

In additional flat envelope embodiments internal and external elements improve their functioning as lightweight tooling and templates. Included are methods to support these mixture-containing envelope structures, both internally with flexible reinforcements and externally with tubular 'foot' structures that also contain state-change mixtures. The flat envelopes may also be backed or supported by liquids or dry media with the ability to capture precise impressions of a shape with the ability to be switched from a liquid-like state to a firm state, or even to a fully hardened state that resembles concrete yet can be returned to a formable condition.

The state change from liquid-like to solid-like properties within the mixtures is effected by the transfer of a small amount of excess carrier medium, the transition liquid, into and out of the mixtures. When the transition liquid is present, preferably in just-sufficient quantity to create the degree of support and clearance that provides for at least two slip-planes, the solid bodies have a degree of mobility similar to that of the liquid medium of the mixture. The slip-plane condition of mobility can be generated through very small liquid pressure differentials or through externally imposed forces that displace the carrier liquid and the supported bodies along with the liquid. Ordered bulk masses of the bodies can shift relative to other ordered masses at any point within a continuous volume of the mixture, and the location of the slip-planes can fluidly shift under any slight differential force transferred from one body to another. It is preferred to prevent frictional contact between bodies during such force transfer by having the liquid medium of the mixture furnish a viscous or 'streaming' resistance to contact, and also for the medium to furnish a degree of body-surface lubrication so that light body contacts do not create friction between bodies.

Lubricity under high contact forces, as is required for many lubricating media, is not necessary within the mixtures since the bodies are in effect free-floating during flow, with any imposed liquid pressure forces being uniformly distributed against the surface of each body. For example a nearly ideal aqueous liquid medium can be formed by dissolving a small quantity of a soluble long-chain polymer such as polyethylene oxide into water. The medium carries solid bodies of a similar density without turbulence and friction-producing contact, allows the bodies to make non-lubricated surface contact when the medium is extracted, and causes the bodies to readily separate when the transition liquid is reintroduced.

When the transition liquid is extracted so that the solid bodies are in a stable configuration with ordered, packed and consolidated contact, the degree of resistance to externally imposed forces depends on such tailorable, engineered physical properties as body shape, body elasticity and compressibility, body surface properties of roughness, smoothness or natural molecular adhesion, residual adhesiveness or lubricity of the liquid medium on the contacting surfaces, surface tension of the medium, and variations of liquid medium or body properties with changes of temperature or pressure; alteration of the resistance properties through replacement of the first liquid with a second liquid medium, rinsing of the bodies and the first medium with a second or sequential liquid media, vapors or gaseous fluids; and any other engineered variations in the bodies and first liquid medium, and in other sequential introductions of various fluids into the mixtures or through the consolidated bodies. Any adhesive or clinging contact between the bodies is preferably relieved through polar molecular action of the first liquid medium, or through an intermediary treatment with other liquids or fluids prior to reintroduction of the first liquid medium.

The container works with quickly reversible state-change mixtures which can be rapidly shifted from a near-liquid or fluent state to a stable force-resisting state through slightly altering the liquid-solid proportions, and the system further provides methods and apparatus for utilizing the mixtures. Embodiments are characterized by one or more of the following advantages: the ability to pressurize a mixture and drive it against a complex surface as if it were a liquid; the ability to create a "near-net" or extremely accurate representation of a shape due to the negligible volumetric change which accompanies a state change; the ability to effect the state-change with a very small volume of single-constituent transfer and with consequently small actuation devices, with a low-energy mechanical actuation, and without requiring a vacuum pump, thermal, chemical or electrical energy to be applied to the mixture; the ability to greatly alter the volume of any elastic or otherwise dimensionally changeable container, envelope or chamber through the free-flowing transfer of the nearly solid mixtures from one container to another; and the ability to tailor the mixtures to satisfy a wide variety of physical specifications in either the flowable or the stable state.

The mixtures can be employed in reformable molds or other shaping tools, and in reusable templates which capture the dimensions of impressed shapes for transfer to a mold. The mixtures can also be used in any product or shape which benefits from the incorporation of arbitrarily reformability or precise reconfigurability. The mixtures further provide useful properties for but are not limited to application in a wide range of shock-absorbing, leveling, protective and supportive apparatus.

It can be appreciated that there are numerous variations of containers and varied combinations of containers which can be employed either to form a surface which is complementary to the exterior surface of a master shape in part or in whole, or to form a surface or surfaces complementary to the interior contours of a hollow master shape or master cavity. For instance more than one container of the first type (rigid frame) or second type (flexible-edge) can be employed to form a continuous surface complementary to a master shape's surface, with the elastomeric membranes of the containers either overlapping or being abutted together. Containers of the second type may also have a membrane and particle configuration that allows two or more of the containers to be "tiled" together to form a continuous surface of particle-backed membranes. Likewise two or more containers of the third type can be employed together to form a shape complementary to the interior of a master cavity. More details on the reformable manufacturing are disclosed in commonly owned patents to Jacobson et al including U.S. Pat. No. 6,398,992 and Pub. No. 20050035477 and 20070187855, the contents of which are incorporated by reference.

In the context of shoe manufacturing, a computing device may be used to determine operations of various shoe-manufacturing tools. For example, a computing device may be used to control a part-pickup tool or a conveyor that transfers shoe parts from one location to another. In addition, a computing device may be used to control a part-attachment device that attaches (e.g., welds, adheres, stitches, etc.) one shoe part to another shoe part.

1. A method to shape a reformable material, comprising:
  generating a 3D model of an object;
  adjusting the 3D model to optimize a parameter or treat a sport enthusiast;
  forming a reformable master shape from the adjusted 3D model;
  holding a volume of particles inside a container having a first elastomeric membrane surface;
  infusing the volume with a liquid to mobilize the volume of particles; and pressing the reformable master shape into the membrane with atmospheric pressure.

2. The method of claim 1, comprising extracting the liquid through one or more screen elements placed proximal to the volume of particles.

3. The method of claim 1, wherein the atmospheric pressure holds the particles against the elastomeric membrane when the master shape is removed from the membrane.

4. The method of claim 1, comprising heating and driving liquid from the particle volume.

5. The method of claim 1, comprising providing a binding adhesive to lock the particles into a force-resisting mass.

6. The method of claim 1, comprising pressing a complementary shape into the master shape in the membrane.

7. The method of claim 1, wherein the container comprises a rigid outside frame with top and bottom elastomeric membranes, comprising pressing the master shape against the elastomeric membrane.

8. The method of claim 7, wherein the pressing comprises applying a flexible vacuum cap sealed over the shape and against the elastomeric membrane surface;
evacuating air from a space formed between the membrane and the vacuum cap;
extracting liquid from the volume; and
pressing the particles within the container with atmospheric force acting in opposed directions against the vacuum cap and the bottom surface membrane.

9. The method of claim 7, comprising introducing air into the vacuum cap, and removing the cap and the master shape from the surface of the elastomeric membrane.

10. The method of claim 1, wherein the container is formed against the master shape.

11. The method of claim 10, comprising performing a liquid infusion, a pressing action under atmospheric pressure, and a liquid extraction.

12. The method of claim 10, comprising
placing the master shape on an air-impermeable surface;
placing a membrane of the container over the shape; and
placing a vacuum cap or a vacuum-bagging film over the container to form the elastomeric membrane against the master shape.

13. The method of claim 1, comprising applying an envelope containing a mass of particles and with a vacuum seal on its perimeter to extract air from a space between the master shape and the envelope.

14. The method of claim 1, comprising placing the master shape on the elastomeric surface of a first rigid-framed container and placing a membrane surface of a second container over the master shape.

15. The method of claim 14, wherein the second container fits inside the frame of the first container and a vacuum cap is placed over and sealed outside the second container against the surface membrane of the first container.

16. The method of claim 14, comprising evacuating the volume under the vacuum cap and pressing the master shape between the elastomeric sides of the first and second containers.

17. The method of claim 16, comprising extracting the liquid to press the two volumes of particles together and against the membranes surrounding the contained shape.

18. The method of claim 14, comprising venting the vacuum cap with air and removing the vacuum cap and the first container; and removing the shape from the membrane of the second container, placing the first container adjacent with the second container; and forming a closed, shaped cavity complementary to the surface of the master shape used to form the cavity.

19. The method of claim 14, comprising pressing two identical containers of either the first or the second container around a master shape without using the vacuum cap.

20. The method of claim 19, wherein the containers are joined and sealed by either a seal mounted on one or both of the containers or by seals mounted on a seal ring fitted between the two containers.

21. The method of claim 1, comprising deaerating the volume of particles.

22. A method to form an object, comprising:
generating a 3D model of an object;
adjusting the 3D model to optimize a parameter or treat a sport enthusiast;
forming a reformable master shape from the adjusted 3D model;
infusing a liquid into a container having a first elastomeric membrane surface;
pressing the master shape into the membrane with atmospheric pressure; and shaping a reformable material into the object according to the master shape.

23. The method of claim 22, comprising extracting the liquid.

24. The method of claim 22, comprising deaerating the volume of particles;

25. The method of claim 22, comprising extracting the liquid through one or more screen elements placed proximal to the volume of particles.

26. The method of claim 22, comprising heating and driving liquid from the particle volume.

27. The method of claim 22, comprising providing a residue of a binding adhesive to lock the particles into a continuous force-resisting mass.

28. The method of claim 22, comprising impressing a complementary shape to the master shape in the membrane.

29. The method of claim 22, wherein the container comprises a rigid outside frame and top and bottom elastomeric membranes facing the top and bottom surfaces of the container, comprising pressing the master shape against the top elastomeric membrane of the container with atmospheric pressure.

30. The method of claim 29, wherein the pressing comprises
applying a flexible vacuum cap sealed over the shape and against the container top surface membrane;
evacuating air from a space between the top surface membrane and the vacuum cap;
extracting liquid from the volume; and
pressing the particles within the container with atmospheric force acting in opposed directions against the vacuum cap and the bottom surface membrane.

31. The method of claim 29, comprising introducing air into the vacuum cap, and removing the cap and the master shape from the formed surface of the elastomeric membrane.

32. The method of claim 22, comprising forming the container against the master shape.

34. The method of claim 32, comprising:
placing the master shape on an air-impermeable surface;
placing a membrane of the container over the shape; and
placing a vacuum cap or a vacuum-bagging film over the container to effect forming of the elastomeric membrane against the master shape.

35. The method of claim 22, comprising applying an envelope containing a mass of particles and with a vacuum seal on the envelope perimeter to extract air from the master shape and the envelope.

36. The method of claim 22, comprising placing the master shape on the top elastomeric surface of a first rigid-framed container and placing a membrane surface of a second container over the master shape.

37. The method of claim 36, wherein the second container fits inside the frame of the first container and a vacuum cap is placed over and sealed outside the second container against the surface membrane of the first container.

38. The method of claim 36, comprising evacuating the volume under the vacuum cap and pressing the master shape between the elastomeric sides of the first and second containers.

39. The method of claim 38, comprising extracting the liquid to press the two volumes of particles together and against the membranes.

40. The method of claim 36, wherein the vacuum cap is vented with air and removed; the top container is removed; and the shape is removed from the membrane of the bottom container, comprising placing the top container over the bottom container; and forming a closed, shaped cavity complementary to the surface of the master shape used to form the cavity.

41. The method of claim 36, wherein the first and second containers are identical, comprising pressing the containers around a master shape without using the vacuum cap.

42. The method of claim 41, wherein the containers are joined and sealed by one of: a seal mounted on one or both containers, a seal mounted on a seal ring fitted between the two containers.

1. A method to form an object, comprising:
infusing a liquid into a container having a frame with first and second elastomeric membranes; a first port to deaerate the volume of particles; and a second port to infuse the volume with a liquid for mobilizing the volume of particles;
generating a 3D model of an object;
adjusting the 3D model to optimize a parameter or treat a sport enthusiast;
forming a reformable master shape from the adjusted 3D model;
pressing the master shape into the membrane with atmospheric pressure; and
shaping a reformable material into the object according to the master shape.

2. The method of claim 1, comprising extracting the liquid.

3. The method of claim 1, comprising deaerating the volume of particles;

4. The method of claim 1, comprising extracting the liquid through one or more screen elements placed proximal to the volume of particles.

5. The method of claim 1, comprising heating and driving liquid from the particle volume.

6. The method of claim 1, comprising providing a binding adhesive to lock the particles into a force-resisting mass.

7. The method of claim 1, comprising pressing a shape complementary to the master shape in the membrane.

8. The method of claim 1, wherein the container comprises a rigid outside frame and top and bottom elastomeric membranes facing the top and bottom surfaces of the container, comprising pressing the master shape against the top elastomeric membrane of the container with atmospheric pressure.

9. The method of claim 8, wherein the pressing comprises
applying a flexible vacuum cap sealed over the shape and against the container's top surface membrane;
evacuating air from a space between the top membrane and the vacuum cap;
extracting liquid from the volume; and
pressing the particles within the container with atmospheric force acting in opposed directions against the vacuum cap and the bottom surface membrane.

10. The method of claim 8, comprising introducing air into the vacuum cap, and removing the cap and the master shape from the formed surface of the elastomeric membrane.

11. The method of claim 1, wherein the container is formed against the master shape.

12. The method of claim 11, comprising:
placing the master shape on an air-impermeable surface;
placing a membrane of the container over the shape; and
placing a vacuum cap or a vacuum-bagging film over the container to effect forming of the elastomeric membrane against the master shape.

13. The method of claim 1, comprising applying an envelope containing a mass of particles and with a vacuum seal on a perimeter to extract air from between the master shape and the envelope.

14. The method of claim 1, comprising placing the master shape on the top elastomeric surface of a first rigid-framed container and placing a membrane surface of a second container over the master shape.

15. The method of claim 14, wherein the second container fits inside the frame of the first container and a vacuum cap is positioned and sealed outside the second container against the surface membrane of the first container.

16. The method of claim 14, comprising evacuating the volume under the vacuum cap and pressing the master shape between the elastomeric sides of the first and second containers.

17. The method of claim 16, comprising extracting the liquid to press the two volumes of particles together and against the membranes surrounding the shape.

18. The method of claim 14, comprising venting the vacuum cap with air and removing the first container; removing the shape from the membrane of the second container, placing the first container adjacent to the second container; and forming a closed, shaped cavity complementary to the surface of the master shape.

19. The method of claim 14, comprising pressing two identical containers of either the first or the second container around a master shape without using the vacuum cap.

20. The method of claim 19, wherein the containers are joined and sealed by either a seal mounted on one or both of the containers or by seals mounted on a seal ring fitted between the two containers.

21. The method of claim 1, comprising extracting the liquid prior to removing the master shape from the shaped reformable material.

22. The method of claim 1, comprising solidifying the liquid within the shaped reformable material.

23. The method of claim 1, comprising withdrawing the liquid to leave a residue of liquid on the shaped reformable material; and solidifying the residue.

24. The method of claim 1, comprising preforming a material surface over the master shape.

25. The method of claim 24, wherein the preforming comprises one of: thermoforming, additive processing.

26. The method of claim 1, wherein the container walls comprise air and liquid impermeable walls.

27. The method of claim 26, comprising providing an inelastic formable surface conforming to the master shape surface.

28. The method of claim 1, comprising forming a surface over the master shape.

29. The method of claim 1, comprising pressing the shaped material surface against the volume of particles without deforming the shaped material surface.

30. The method of claim 1, comprising:
providing a release surface to the master shape;
pressing the master shape against the volume of particles to form the object with the release surface; and
removing the object using the release surface.

31. The method of claim 30, wherein providing the release surface comprises providing an area around the master shape with a surface element covering the reformable material surface not overlaid with the master shape surface;

1. An apparatus to form an object in accordance with a master shape, comprising:
a computer actuated 3D shape generator to render the master shape;
a container to hold a volume of particles, said container having a first elastomeric membrane surface; a first port to deaerate the volume of particles; and a second port to infuse the volume with a liquid for mobilizing the volume of particles; and
a press coupled to the container to move the master shape into the membrane to shape a reformable material into the object according to the shape generator's master shape.

2. The apparatus of claim 1, comprising one or more screen elements placed proximal to the volume of particles to extract the liquid.

3. The apparatus of claim 1, wherein atmospheric pressure holds the volume of particles in place against the elastomeric membrane when the master shape is removed from the membrane.

4. The apparatus of claim 1, comprising a heater to heat and drive liquid from the particle volume.

6. The apparatus of claim 1, wherein the container comprises a rigid outside frame and top and bottom elastomeric membranes facing the top and bottom surfaces of the container, and wherein the master shape is pressed against the top elastomeric membrane of the container by atmospheric pressure.

7. The apparatus of claim 6, comprising:
a flexible vacuum cap sealed over the shape and against the container's top surface membrane;
a third port to evacuate air from a space between the top membrane and the vacuum cap; and
wherein the particles within the container are pressed with atmospheric force acting in opposed directions against the vacuum cap and the bottom surface membrane.

8. The apparatus of claim 6, wherein air is introduced into the vacuum cap, and wherein the cap and the master shape are removed from a surface of the elastomeric membrane.

9. The apparatus of claim 8, wherein the master shape is placed between an air-impermeable surface and the membrane of the container and wherein a vacuum cap or a vacuum-bagging film is placed over the container to form the elastomeric membrane against the master shape.

10. The apparatus of claim 1, comprising an envelope containing a mass of particles and with a vacuum seal on its perimeter to extract air between the master shape and the envelope.

11. The apparatus of claim 1, comprising placing the master shape on the top elastomeric surface of a first rigid-framed container and placing a membrane surface of a second container over the master shape.

12. The apparatus of claim 11, wherein the second container fits inside the frame of the first container and a vacuum cap is placed over and sealed outside the second container against the surface membrane of the first container.

13. The apparatus of claim 11, comprising a vacuum pump to evacuate the volume under the vacuum cap and press the master shape between the elastomeric sides of the first and second containers.

14. The apparatus of claim 11, comprising a pump to extract the liquid to press the two volumes of particles together and against the membranes surrounding the contained shape.

15. The apparatus of claim 14, wherein the vacuum cap is vented with air and removed; the first container is removed; and the shape is removed from the membrane of the second container and wherein the first container is placed adjacent the second container to form a closed, shaped cavity complementary to the surface of the master shape used to form the cavity.

16. The apparatus of claim 14, wherein the first and second containers are identical and wherein the containers are pressed around a master shape without using the vacuum cap.

17. The apparatus of claim 14, wherein the containers are joined and sealed by either a seal mounted on one or both of the containers or by seals mounted on a seal ring fitted between the containers.

18. The apparatus of claim 14, comprising a seal ring to channel vacuum or air pressure between the containers and to hold the master shape in a predetermined orientation and position between the opposed containers.

19. The apparatus of claim 1, comprising an expander within the container to press the particulate material against cavity walls of the container.

20. The apparatus of claim 1, comprising
a second container cooperating with the first container to form a complementary cavity from the master shape; and
a third container placed in the complementary cavity to replicate the master shape.

21. The apparatus of claim 1, wherein the container comprises a frame.

22. The apparatus of claim 21, wherein the frame comprises one of: a rigid frame, a flexible-edge frame.

23. The apparatus of claim 21, wherein the frame comprises a continuous surface complementary to a master shape's surface.

24. The apparatus of claim 1, comprising a second elastomeric membrane, wherein the elastomeric membranes overlap each other.

25. The apparatus of claim 1, comprising a second elastomeric membrane, wherein the elastomeric membranes abut each other.

26. The apparatus of claim 1, comprising one or more additional containers each having a membrane coupled to the container to form a continuous surface of membranes.

27. The apparatus of claim 1, comprising one or more additional containers to form a shape complementary to the interior of a master cavity.

1. An apparatus to form an object in accordance with a master shape, comprising:
a computer actuated 3D shape generator to render the master shape;
a container to hold a volume of particles, said container having a frame with first and second elastomeric membranes; a first port to deaerate the volume of particles; and a second port to infuse the volume with a liquid for mobilizing the volume of particles; and a press coupled to the container to move the master shape into the membrane to shape a reformable material into the object according to the master shape.

2. The apparatus of claim 1, wherein the second membrane is bonded to the frame.

3. The apparatus of claim 1, wherein the first membrane is coupled to a seal.

4. The apparatus of claim 1, comprising a clamp to secure at least one membrane to the frame.

5. The apparatus of claim 1, comprising one or more ports on the frame.

6 The apparatus of claim 1, comprising liquid, evacuation, and vacuum-activated seal tubes coupled to the frame.

7. The apparatus of claim 1, comprising a rim evacuation screen element positioned in the frame.

8. The apparatus of claim 1, wherein the frame is one of: a rigid frame, a flexible frame.

9. The apparatus of claim 1, comprising a vacuum activated seal on the frame.

10. The apparatus of claim 1, comprising a tube to evacuate and fill the container.

11. The apparatus of claim 1, comprising double layer screens having feed elements to distribute and extract liquid through the volume of particles.

12. The apparatus of claim 1, comprising one or more screens conformally coupled to the master shape.

13. The apparatus of claim 1, comprising one or more internal screens mounted with the particles flowing on both sides of each internal screen.

14. The apparatus of claim 1, wherein the frame is flexible, comprising one or more containers joined together around the master shape.

15. The apparatus of claim 1, wherein the frame is flexible, comprising one or more containers joined by vacuum seals.

16. The apparatus of claim 1, comprising one or more feed tubes coupled to an interior element inside the membrane.

17. The apparatus of claim 1, comprising a flexible spine element within an interior cavity of the container.

18. The apparatus of claim 1, comprising one or more reinforcement fibers.

19. The apparatus of claim 18, wherein the fibers are distributed in bundles within the volume of particles.

20. The apparatus of claim 1, comprising an air pump to provide internal pressurization.

21. The apparatus of claim 1, comprising a vacuum source to provide a vacuum between a cavity in the container and the container.

22. The apparatus of claim 1, comprising an air pump and a vacuum source to alternately pressurize and vent the container to distribute the volume of particles therein.

23. The apparatus of claim 1, comprising a seal ring.

24. The apparatus of claim 23, wherein the seal rings are mounted.

25. The apparatus of claim 23, wherein the seal comprises a vacuum activated seal.

26. The apparatus of claim 23, comprising a second container joined with the container and wherein a vacuum is formed in an interior of the joined containers.

27. The apparatus of claim 26, wherein the master shape is mounted on the seal ring.

28. The apparatus of claim 26, comprising one or more flanges mounted to control a mating line between opposed membranes of containers.

29. The apparatus of claim 1, comprising a second container positioned within a cavity formed by an outside container.

30. The apparatus of claim 1, comprising a vacuum cap.

31. The apparatus of claim 30, comprising a vacuum seal coupled to the vacuum cap.

32. The apparatus of claim 30, comprising a vacuum tube penetrating through the membrane.

33. The apparatus of claim 1, comprising a vacuum cap with mounted container 245 in place of the membrane 34. The apparatus of claim 1, comprising one or more screen elements placed proximal to the volume of particles to extract the liquid.

35. The apparatus of claim 1, wherein atmospheric pressure holds the volume of particles in place against the elastomeric membrane when the master shape is removed from the membrane.

36. The apparatus of claim 1, comprising a heater to heat and drive liquid from the particle volume.

37. The apparatus of claim 1, wherein the container comprises a rigid outside frame and top and bottom elastomeric membranes facing the top and bottom surfaces of the container, and wherein the master shape is pressed against the top elastomeric membrane of the container with atmospheric pressure.

38. The apparatus of claim 1, comprising an envelope containing a mass of particles and with a vacuum seal on its perimeter to extract air from between the master shape and the envelope.

39. The apparatus of claim 1, comprising placing the master shape on the top elastomeric surface of a first rigid-framed container and placing a membrane surface of a second container over the master shape.

40. The apparatus of claim 1, comprising an expander within the container to press the particulate material against cavity walls of the container.

41. The apparatus of claim 1, comprising
a second container cooperating with the first container to form a complementary cavity from the master shape; and
a third container placed in the complementary cavity to replicate the master shape.

42. The apparatus of claim 1, comprising a second elastomeric membrane, wherein the elastomeric membranes overlap or abut each other.

43. The apparatus of claim 1, comprising one or more additional containers each having a membrane coupled to the container to form a continuous surface of membranes.

44. The apparatus of claim 1, comprising one or more additional containers to form a shape complementary to the interior of a master cavity.

1. A base station to form an object in accordance with a master shape, comprising:
a computer actuated 3D shape generator to render the master shape;
a liquid receiver;
a vacuum source to evacuate air from the liquid receiver;
an air compressor to generate pressurized air; and
a controller coupled to the liquid receiver, the vacuum source and the air compressor to form the object.

2. The base station of claim 1, comprising one or more tubes to provide vacuum and to control the flow of liquids to and from the receiver.

3. The base station of claim 1, comprising one or more valves coupled to the controller.

4. The base station of claim 1, comprising one or more sensors coupled to the controller.

5. The base station of claim 1, comprising an electrical power supply to operate valves, sensors, the vacuum pump and the air compressor.

6. The base station of claim 1, wherein the controller comprises a menu-driven process controller to operate the base station.

7. The base station of claim 1, comprising a heater to vaporize and expel liquid from the receiver and to heat a reformable material.

8. The base station of claim 7, wherein the reformable material creates contours of the master shape.

9. The base station of claim 7, wherein the reformable material is molded against a complementary surface of an elastomeric membrane.

10. The base station of claim 7, wherein the liquid contains a soluble binder.

11. The base station of claim 10, wherein the binder remains on a shaped volume of particles.

12. The base station of claim 10, wherein the binder locks a shaped volume of particles in place after the liquid is removed.

13. The base station of claim 7, comprising wherein the heater comprises one of: a radiant heater, a convective air heater, a microwave heater, a radio-frequency heater, an inductive heater.

14. The base station of claim 7, comprising the heater comprises one or more heating elements within the container.

15. The base station of claim 7, comprising the heater is controlled by the controller.

16. The base station of claim 1, comprising:
a container to hold a volume of particles, said container having a frame with first and second elastomeric membranes; a first port to deaerate the volume of particles; and a second port to infuse the volume with a liquid for mobilizing the volume of particles; and
a press coupled to the container to move the master shape into the membrane to shape a reformable material into the object according to the master shape.

17. The base station of claim 1, comprising
a container to hold a volume of particles, said container having a first elastomeric membrane surface; a first port to deaerate the volume of particles; and a second port to infuse the volume with a liquid for mobilizing the volume of particles; and
a press coupled to the container to move the master shape into the membrane to shape a reformable material into the object according to the master shape.

18. The base station of claim 17, wherein the container comprises a rigid outside frame and top and bottom elastomeric membranes facing the top and bottom surfaces of the container, and wherein the master shape is pressed against the top elastomeric membrane of the container by atmospheric pressure.

19. The base station of claim 18, comprising:
a flexible vacuum cap sealed over the shape and against the container's top membrane;
a third port to evacuate air from a space between the top membrane and the vacuum cap; and
a fourth port to extract liquid from the volume;
wherein the particles within the container are pressed by atmospheric force acting in opposed directions against the vacuum cap and a bottom membrane.

20. The base station of claim 18, wherein the master shape is placed between an air-impermeable surface and the membrane of the container and wherein a vacuum cap or a vacuum-bagging film is placed over the container to form the elastomeric membrane against the master shape.

21. The base station of claim 1, wherein the vacuum pump comprises one of: a mechanical pump, an air driven pump.

22. The base station of claim 1, wherein the vacuum comprises a Venturi pump.

23. The base station of claim 1, comprising a second vacuum pump.

24. The base station of claim 23, comprising isolating valves coupled to the vacuum pumps.

25. The base station of claim 1, comprising a regulator and one or more valves coupled to the vacuum pump to pressurize a liquid tank.

26. The base station of claim 25, comprising a vent valve coupled to the liquid tank to cycle from a vacuum source to a pressure source.

27. The base station of claim 25, comprising a three-way valve to route air and vacuum to the liquid tank.

28. The base station of claim 25, comprising a filter coupled to the liquid tank to prevent particulate carryover.

29. The base station of claim 1, comprising an air-liquid separator.

30. The base station of claim 1, comprising a level indicator.

31. The base station of claim 1, comprising a vacuum sensor coupled to the controller for process control.

32. The base station of claim 1, comprising a heat exchanger coupled to the container to condense vapor.

33. The base station of claim 1, comprising one or more outside containers in combination forming a cavity and an inside container in the formed cavity.

34. The base station of claim 1, comprising a slurry transfer tank coupled to the container.

35. The base station of claim 1, comprising one or more containers coupled to the container.

36. The base station of claim 35, wherein the containers are mated with a seal ring.

1. A method to shape a reformable material, comprising:
generating a 3D model of an object;
adjusting the 3D model to optimize a parameter or treat a wearer;
forming a reformable master shape from the adjusted 3D model;
holding a volume of particles inside a container having a first elastomeric membrane surface; and infusing the volume of particles with a liquid;
agitating the liquid to provide one or more surges of liquid to mobilize the volume of particles; and pressing the master shape into the membrane with atmospheric pressure.

2. The method of claim 1, comprising providing locally distributed surges.

3. The method of claim 1, comprising providing globally distributed surges.

4. The method of claim 1, wherein the one or more surges exert differential liquid forces on particles to displace them relative to one another and facilitate their movement into a closely-packed volume.

5. The method of claim 1, comprising providing a differential pressure between a master shape side and a liquid-particle side of the membrane.

6. The method of claim 1, comprising decreasing the pressure between a vacuum cap and the membrane to move the membrane in a first direction.

7. The method of claim 1, comprising increasing the pressure between a vacuum cap and the membrane to move the membrane in a second direction.

8. The method of claim 6, wherein membrane is free to move relative to master shape.

9. The method of claim 1, wherein the liquid moves through particles toward membrane, and wherein the particles move toward the membrane.

10. The method of claim 1, comprising removing excess liquid and leaving particles against the membrane.

11. The method of claim 1, comprising evacuating air from space between the membranes.

12. The method of claim 1, comprising packing the particles against the membranes and the master shape.

13. The method of claim 1, comprising extracting the liquid with the vacuum cap and membrane pressed against the master shape to pack the particles against the membranes and the master shape.

14. The method of claim 1, wherein the agitating comprises pulsing the liquid.

15. The method of claim 1, wherein the agitating comprises vibrating the liquid.

16. The method of claim 15, comprising adjusting a vibration frequency to displace one particle relative to another to keep the particles moving freely in relation to one another.

17. The method of claim 1, wherein amplitude of liquid pulsation is proximally equal to a diameter of the particles.

18. The method of claim 1, comprising generating a first surge of liquid towards a desired transport direction.

19. The method of claim 18, comprising generating a second surge smaller than the first surge in an opposite direction to the transport direction.

20. The method of claim 1, comprising agitating the liquid to minimize blockage.

21. The method of claim 1, comprising maintaining the volume of the container constant and completely filled to force the particles against the master shape.

22. The method of claim 21, comprising:
extracting transitional liquid from the container; and
adding new liquid equal in volume of the transition liquid.

1. A shape-reformable composition, comprising:
a carrier medium having a carrier density; and
a plurality of solid bodies having a density substantially similar to the carrier density, said solid bodies being transitionable from a formable state to a three dimensional solid shape.

2. The composition of claim 1, wherein the carrier medium fills voids or interstices between the solid bodies.

3. The composition of claim 1, wherein the voids or interstices are free of air or gas bubbles.

4. The composition of claim 1, wherein the solid bodies comprise a near-liquid or fluent mobility during the formable state.

5. The composition of claim 1, wherein the solid bodies transition to the solid shape through an introduction and an extraction of a predetermined amount of the carrier medium.

6. The composition of claim 1, wherein solid bodies are positioned in a container having a first elastomeric membrane surface.

7. The composition of claim 6, wherein liquid is introduced to mobilize the volume of particles.

8. The composition of claim 6, wherein a master shape is pressed into the membrane with atmospheric pressure.

9. The composition of claim 1, wherein the solid shape comprises a stable, force-resisting shape.

10. The composition of claim 1, wherein the solid bodies and carrier medium form a reversible state-changeable mixture 11. The composition of claim 1, wherein the carrier medium comprises a liquid.

12. The composition of claim 1, wherein the carrier medium comprises a gaseous froth.

13. The composition of claim 1, wherein the shape comprises a reformable mold.

14. The composition of claim 1, comprising a reusable template to capture dimensions of impressed shapes for transfer to a mold.

15. The composition of claim 1, comprising a binder to bind the solid bodies.

16. The composition of claim 15, wherein the binder comprises one of: a TEOS binder, an ethanol based material, a eutectic metal, and a fiber.

17. The composition of claim 15, wherein the binder comprises a thermally conductive particle.

18. The composition of claim 15, wherein the binder comprises one or more electrically heated particles.

19. The composition of claim 18, wherein the particle comprise a resistive coating for resistive heating.

20. The composition of claim 15, wherein the binder comprises an elastomeric binder.

21. The composition of claim 15, wherein the binder is hardened with introduced liquid or gas after forming.

22. The composition of claim 15, wherein the binder is hardened with hot air through the particles.

23. The composition of claim 22, wherein the binder is formed at a pressure above atmospheric pressure.

24. The composition of claim 15, wherein a pH value for the binder is increased or decreased.

25. The composition of claim 1, comprising a surface coating on shaped solid bodies to add smoothness, toughness, and better release properties for the composition.

1. A vacuum activated seal for a container, comprising:
a channel having one or more legs angled outwardly and spaced apart, said legs having contact areas adapted to be pressed against a surface with a greater force per unit area than atmospheric pressure; said channel having an opening therein; and
a tube penetrating from the outside of the channel to the inside of the channel through the opening.

2. The seal of claim 1, wherein the channel is mounted as a continuous ring.

3. The seal of claim 2, wherein the ring is positioned on the container perimeter.

4. The seal of claim 1, wherein the ring is positioned on a flange.

5. The seal of claim 1, wherein the legs are forced against the surface by atmospheric pressure when the channel is evacuated.

6. The seal of claim 1, wherein a total unit area on the back of the channel exceeds the total unit area of the leg area in contact with the surface.

7. The seal of claim 1, wherein the seal is used to enclose a volume between two air-impermeable elements.

8. The seal of claim 7, wherein the seal prevents leakage from the outside to the inside of the volume as a contact pressure exceeds atmospheric pressure.

8A. The seal of claim 8, wherein the contact pressure comprises applying a vacuum on the volume.

9. The seal of claim 1, wherein the seal scavenges air from the outside if a leak occurs through imperfections in the seal or the surface.

10. The seal of claim 1, wherein the surface of the seal is placed against or pressed down against a smooth air-impermeable surface.

10. The seal of claim 1, wherein the surface comprises one of: a flange-mounted membrane, a seal ring, a second seal.

11. The seal of claim 1, wherein a vacuum is introduced through the tube to extract air from the inside of the seal.

12. The seal of claim 1, wherein atmospheric pressure acting on the back of the channel presses the legs of the channel against the surface.

13. The seal of claim 1, wherein the channel comprises a resilient material.

14. The seal of claim 1, wherein the channel comprises an elastomeric material.

15. The seal of claim 1, wherein the channel comprises rubber.

16. The seal of claim 1, comprising a container to hold a volume of particles, said container having a first elastomeric membrane surface; a first port to deaerate the volume of particles; and a second port to infuse the volume with a liquid for mobilizing the volume of particles.

17. The seal of claim 16, comprising a press coupled to the container to move the master shape into the membrane to shape a reformable material into the object according to the master shape.

18. The seal of claim 16, comprising one or more screen elements placed proximal to the volume of particles to extract the liquid.

19. The seal of claim 16, wherein atmospheric pressure holds the volume of particles in place against the elastomeric membrane when the master shape is removed from the membrane.

20. An apparatus to form an object in accordance with a master shape, comprising:

a container to hold a volume of particles, said container having a first elastomeric membrane surface; a first port to deaerate the volume of particles; and a second port to infuse the volume with a liquid for mobilizing the volume of particles; and a vacuum activated seal for the container, including: a channel having one or more legs angled outwardly and spaced apart, said legs having contact areas adapted to be pressed against a surface with a greater force per unit area than atmospheric pressure; said channel having an opening therein; and a tube penetrating from the outside of the channel to the inside of the channel through the opening; and a press coupled to the container to move the master shape into the membrane to shape a reformable material into the object according to the master shape.

Augmented Reality/Virtual Reality Sports Gaming

FIG. 15 shows an exemplary 360 degree camera on a helmet, for example, for augmenting reality of sport games. Using augmented reality, various ways may exist for a user to "participate" in a live event. Generally, augmented reality refers to a presentation of a real world environment augmented with computer-generated data (such as sound, video, graphics or other data). In some embodiments, augmented reality, implemented in conjunction with a live event, may allow a user to control a virtual object that appears to compete or otherwise interact with the participants of the live event. For example, an end user device, such as a mobile phone, tablet computer, laptop computer, or gaming console may be used to present a live video feed of an event to a user. This live video feed may be video of an event that is occurring in real-time, meaning the live event is substantially concurrently with the presentation to the user (for example, buffering, processing, and transmission of the video feed may result in a delay anywhere from less than a second to several minutes). The presentation of the live event may be augmented to contain one or more virtual objects that can be at least partially controlled by the user. For instance, if the live event is a stock car race, the user may be able to drive a virtual car displayed on the end user device to simulate driving in the live event among the actual racers. As such, the user may be able to virtually "compete" against the other drivers in the race. The virtual object, in this example a car, may be of a similar size and shape to the real cars of the video feed. The user may be able to control the virtual car to race against the real cars present in the video feed. The real cars appearing in the video feed may affect the virtual object. For example, the virtual object may not be allowed to virtually move through a real car on the augmented display, rather the user may need to drive the virtual object around the real cars. Besides racing, similar principles may be applied to other forms of live events; for example, track and field events (e.g., discus, running events, the hammer toss, pole vaulting), triathlons, motorbike events, monster truck racing, or any other form of event that a user could virtually participate in against the actual participants in the live event. In some embodiments, a user may be able to virtually replay and participate in past portions of a live event. A user that is observing a live event may desire to attempt to retry an occurrence that happened during the live event. While viewing the live event, the user may be presented with or permitted to select an occurrence that happened in the course of the live event and replay it such that the user's input affects the outcome of at least that portion of the virtualized live event. Using a baseball game as an example, with runners on first and third, two outs, and the count being two balls and two strikes, the pitcher may throw a splitter, successfully striking out the batter with a pitch in the dirt. The inning may end and the game may continue. The user may desire to replay this unsuccessful at-bat with himself controlling the batter during the commercial break. As such, via an end user device, the user may be able to indicate the portion of the game he wishes to replay (e.g., the last at-bat). Game facts from the live event may be used to virtually recreate this at-bat for the user. For instance, the virtual game loaded by the user may use game facts leading up to the at-bat the user has selected. For instance, the opposing team, the stadium, the score, the time of day, the batter, the pitcher, and the sequence of pitches thrown by the pitcher may be used to provide the user with a virtual replay of at least that portion of the baseball game that the user can affect via input (e.g., swinging and aiming the virtual bat). In replaying the selected portion of the live event, the entire event may be virtualized. As such, referring to the baseball example, the pitcher, stadium, field, fielders, batter, and ball may all be replaced by virtual objects, with one (or more) of the virtual objects, such as the batter, being controlled by the user. As such, this may resemble a video game instantiated with data from the live event. In some embodiments, a portion of the live event may involve a playback of a video feed of the live event with a virtual object that is controlled by the user being augmented. Referring again to the example of the baseball game, the pitcher, stadium, fielders, and field may be replayed from the video feed; the batter and/or ball may be virtualized. As such, the user may control the batter and swing at a virtual ball that has taken the place of the real ball present in the video feed. Besides baseball, such reenactment of a portion of a live event may be applied to various forms of sporting events, such as football, soccer, tennis, golf, hockey, basketball, cricket, racing, skiing, gymnastics, and track and field events. Other forms of live events, besides sports, may also be reenacted using such techniques.

Figure 15A:
FIG. 15A shows an exemplary virtual reality camera mounted on a gear.

FIG. 15A shows a multi-headed camera array 423 that may be at least part of a modular camera system, with each camera forming a module of the modular camera system. The camera array has a flexible structure so that it is easy to remove a particular camera module from the camera array and to add new camera modules to the camera array. The camera modules in the camera array may be configured in different geometries. For example, the camera array includes multiple camera modules arranged in a line, a cylinder, a sphere, or another geometry. Each camera module may be configured to point to a different direction so that the camera array may capture an object or a scene from multiple directions at the same time.

The camera system described herein may additionally include a set of algorithms for processing the video data captured by the camera array. The set of algorithms are stored on a non-transitory memory for converting the input across multiple camera modules into a single stream of 3D video (e.g., a single compressed stream of 3D video data). The set of algorithms may be implemented in one or more "modules". For example, the set of algorithms includes color correction algorithms for smoothing and correcting colors in the video data. In another example, the set of algorithms may be implemented in software that stitches the video data from multiple cameras into two large-format, panoramic video streams for left and right eye viewing, and encodes and compresses the video using a standard MPEG format or other suitable encoding/compression format.

The camera array 423 may be constructed using various configurations. For example, the camera modules may be configured in different geometries (e.g., a sphere, a line, a cylinder, a cone, a cube, etc.) with the corresponding lenses 113 facing in different directions. For example, the camera modules are positioned within the camera array 423 in a honeycomb pattern where each of the compartments form an aperture where a camera module may be inserted. In another example, the camera array 423 includes multiple lenses along a horizontal axis and a smaller number of lenses on a vertical axis.

In some embodiments, the camera modules in the camera array 423 are oriented around a sphere in different directions with sufficient diameter and field-of-view to capture enough view disparity to render stereoscopic images.

The camera array 423 has a flexible structure so that a particular camera module may be removed from the camera array 423 easily. In some embodiments, the camera modules are rotationally symmetrical such that a camera module may be inserted into the housing, removed, rotated 90 degrees, and reinserted into the housing. In this example, the sides of the housing may be equidistant, such as a camera module with four equidistant sides. This allows for a landscape orientation or a portrait orientation of the image frames without changing the base. In some embodiments, the lenses and the camera modules are interchangeable. New camera modules may also be added to the camera array 423. In some embodiments, the camera modules in the camera array 423 are positioned to have a sufficient field-of-view overlap so that all objects can be seen by more than one view point. In some embodiments, having the camera array 423 configured so that an object may be viewed by more than one camera may be beneficial for correcting exposure or color deficiencies in the images captured by the camera array 423. Other benefits include disparity/depth calculations, stereoscopic reconstruction, and the potential to perform multi-camera high-dynamic range (HDR) imaging using an alternating mosaic pattern of under- and over-exposure across the camera array.

In some embodiments, the camera array 423 may also include a microphone array for capturing sound from all directions. For example, the microphone array may include a Core Sound Tetramic soundfield tetrahedral microphone array following the principles of ambisonics, enabling reconstruction of sound from any arbitrary direction. In another example, the microphone array includes the Eigenmike, which advantageously includes a greater number of microphones and, as a result, can perform higher-order (i.e. more spatially accurate) ambisonics. The microphone may be mounted to the top of the camera array 423, be positioned between camera modules, or be positioned within the body of the camera array 423. The result can then be rendered as an immersive video and a user can view the video with computer annotations thereon for augmented reality purposes. In one implementation, the event may be a live event, for example, but is not limited to, a football match, a cricket match, a basketball match, a theatre, a concert, and the like. In one embodiment, the augmented reality content may include, but is not restricted to, live content associated with an event, recorded content associated with an event, a curated content, an advertising content, or a combination thereof. In another embodiment, the augmented reality content may include, but is not restricted to, information related to a service available at an event, a venue of an event, a status of a service, or a combination thereof. The system 100 may also provide the augmented reality content associated with, but is not restricted to, a venue of an event, duration of an event, a location of an event, or a combination thereof, in another implementation.

One embodiment allows combined augmented reality and virtual reality on the display. The method may include selectively allowing a transmission of light from a local environment of the user based on a visualization mode of the display object. The visualization mode may be one of an augmented reality mode, a virtual reality mode, and a combination of augmented and virtual reality modes.

In another embodiment, sensors may be placed to track eye movement as well as hand gestures and verbal commands. The method may further comprise capturing a field-of-view image of each of the user's eyes. The captured field of view image may be used to estimate a head pose of the user. The captured field-of-view image may be used to convert at least one physical object to a physically rendered virtual object, and to display the physically rendered virtual object to the user. In another embodiment, sensors may be placed to track eye movement as well as hand gestures and verbal commands. Then, a method comprises tracking a movement of a user's eyes, estimating a depth of focus of the user's eyes based on the tracked eye movement, modifying a light beam associated with a display object based on the estimated depth of focus such that the display object appears in focus, and projecting the modified light beam into the user's eyes. The diameter of the projected light beam projected to the user's eyes may be less than 0.7 mm.

For the athlete/participant who wish to enhance their gaming via augmented or virtual reality, features may include the following:

1. A method for using augmented reality, the method comprising: receiving, by a computerized device, a data stream with a 360 degree view of a live event on each participant, wherein the data stream comprises live video augmented with positions of team mates and opposing players and recommends a play routine based on live field condition and positions of other players, wherein the user can select a point of view from a selected participant.

2. The method for using augmented reality of claim 1, wherein the user plays in a virtual reality version of the live event.

3. The method for using augmented reality of claim 1, wherein the live event is a sporting event.

4. The method of claim 7, wherein the live event comprises: soccer, football, basketball, tennis, boxing, car racing, golf, ice hockey, badminton, volleyball, cycling, swimming, snooker, martial arts, rugby, motorbike, hockey, table tennis, horse racing, gymnastics, handball, figure skating, wrestling, skiing, diving, skating, archery, sailing, wrestling, fencing, equestrian, rowing, surfing, Beach Volleyball, Pool/Billiards, Lacrosse, Windsurfing, Polo, Tenpin Bowling, Racquetball, Competitive Climbing, Mountain Biking.

Figure 15B:
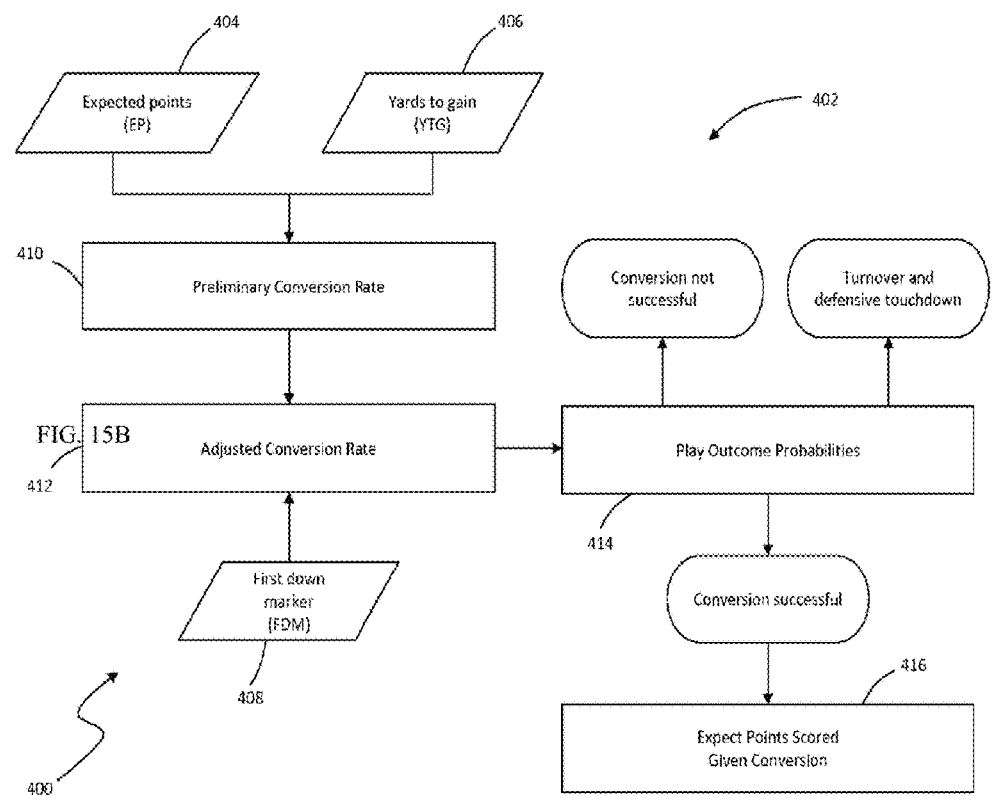
FIG. 15B shows exemplary augmented reality real-time coaching of a player such as a quarterback during fourth down.

FIG. 15 shows an exemplary recommender to aid an athlete in improving the game. For example, the process can recommend a strategy in light of the opponent's historical performance. In tennis, a player's historical weakness can be ascertained and a recommendation can be made to optimize success. In a football example, a fourth down module 400 may include a Football recommender, a Field Goal algorithm, and a Punt algorithm. The Football recommender determines the probability of each potential play outcome associated with the Go For It coaching decision. The Field Goal algorithm determines the probability of each potential play outcome associated with the Field Goal coaching decision. The Punt algorithm 1102 determines the probability of each potential play outcome associated with the Punt coaching decision. As shown in FIG. 15B, the Football recommender 402 determines the probability of each potential play outcome associated with the Go For It coaching decision on a fourth down play. The Football recommender 402 receives an expected points (EP) input from the expected points module 300 at block 404, a yards to gain (YTG) for first down input at block 406, and a first down marker (FDM) yard line input at block 408. Preliminary Conversion Rate: At block 410, the Football recommender 402 uses the team's EP value from block 404 and the YTG distance from block 406 to determine a preliminary first down conversion rate based on historical conversion data. Historical first down conversion data is shown in the form of a chart in FIG. 5, where YTG distances are presented on the x-axis and average first down conversion rates are presented on the y-axis. This historical data shows that the likelihood of a first down conversion decreases as the YTG distance increases. Individual lines or equations may be presented to account for various EP values. For simplicity, FIG. 5 shows three lines to account for scenarios in which the offense and defense are an equal match with the same EP values (NEU), the offense has the advantage (OFF AD), and the defense has the advantage (DEF AD). The historical data presented in FIG. 5 shows that stronger offenses will convert first downs versus weaker defenses (OFF AD) more often than weaker offenses will convert first downs versus stronger defenses (DEF AD). Similar lines may be provided for specific EP values (e.g., 7-66 points). By determining the first down conversion rate at each YTG distance for each offensive match-up, the Football recommender 402 is able to predict the likelihood of a first down conversion with great precision.

Inside an opponent's 20-yard line (i.e., in the Red Zone), it becomes more difficult to convert for a first down as the space on the field from which to work becomes more limited. As the FDM gets closer to the end zone and the YTG distance increases, the challenge of converting a first down gets progressively more difficult versus similar scenarios outside of the Red Zone. To account for the challenge of converting a first down in the Red Zone, the Football recommender 402 may multiply the preliminary conversion rate by a field position multiplier at block 412 based on the YTG distance from block 406 and the FDM yard line from block 408 (where 100 represents the opponent's goal line. As an example, take a team that normally has a 50% fourth down conversion rate with 2 YTG. If the team faces a fourth down play with 2 YTG outside of the Red Zone, the conversion rate may remain at 50%. However, if the team faces a fourth down play with 2 YTG in the Red Zone, such as from the opponent's 2-yard line when the FDM is on the opponent's goal line (FDM=100), the normal 50% conversion rate may be multiplied by the corresponding field position multiplier of 85.5% to arrive at a lower adjusted conversion rate of 42.7%. The process may adjust team's first down conversion rate at block 412 based on particular strengths of his team. In one embodiment, the Football recommender 402 multiplies the conversion rate by one or more additional multipliers, such as a YTG multiplier, which may be specified by the coach. As an example, a team that thrives on running the football might find that it converts short-yardage situations particularly well, because its offense is designed to consistently grind out short gains. However, the same team may have particular difficulty in converting longer-yardage situations because the offense isn't conducive to big plays. In this example, the YTG multiplier may be greater than 100% below 5 YTG to increase the conversion rate in short-yardage situations and less than 100% above 5 YTG to decrease the conversion rate in long-yardage situations. Conversely, a team with an explosive offense may be particularly effective in converting long yardages but may not have the personnel to get short yardage. In this example, the YTG multiplier may be less than 100% below 5 YTG to decrease the conversion rate in short-yardage situations and greater than 100% above 5 YTG to increase the conversion rate in long-yardage situations. The Indianapolis Colts were a great example of this during much of the Peyton Manning era. They were very dangerous in long-yardage situations due to the quality of their passing game, but due to a poor running game, they often failed to convert in short-yardage scenarios. The Football recommender 402 may calculate the probability of a turnover and defensive touchdown as a function of the EP value from block 404 and the FDM yard line from block 408. This probability may be as low as about 0.1% and as high as about 0.5%. At block 414, the Football recommender 402 assigns probabilities to each potential conversion outcome. The Football recommender 402 may determine not only the likelihood of a first down conversion at block 412, but also how likely the team is to score points if the conversion is successful at block 416. After a successful conversion, the team could get just enough yards to get the first down and still not score any points on the drive, or it could score a touchdown on the very same play or a subsequent play of the same drive. Therefore, the Football recommender 402 may take into account the potential upside of the drive should the fourth down play be successful at any field position. At block 416, the Football recommender 402 uses the team's EP value from block 404 and the FDM yard line from block 408 to determine the points scored given conversion based on historical scoring data. Historical scoring data is shown in the form of a chart in FIG. 6, where FDM yard lines are presented on the x-axis (with 0 representing the team's own goal line and 100 representing the opponent's goal line) and average points scored given conversion are presented on the y-axis. This historical data shows that the likelihood of scoring points increases as the FDM approaches the opponent's goal line. Individual lines or equations may be presented to account for various EP values. For simplicity, FIG. 6 shows three lines to account for scenarios in which the offense and defense are an equal match with the same EP values (NEU), the offense has the advantage (OFF AD), and the defense has the advantage (DEF AD). The historical data presented in FIG. 6 shows that stronger offenses will score more points versus weaker defenses (OFF AD) than weaker offenses will score versus stronger defenses (DEF AD). Similar lines may be provided for specific EP values (e.g., 7-66 points). In this manner, the augmented reality system can enhance the game.

For viewers who wish to participate via augmented or virtual reality, features may include the following:

1. A method for using augmented reality, the method comprising: receiving, by a computerized device, a data stream with a 360 degree view of a live event on each participant, wherein the data stream comprises live video, wherein: the live video comprises a live object; receiving, by the computerized device, input from a user, wherein the input from the user affects behavior of a virtual object; and presenting, by the computerized device, the live event augmented by the virtual object, wherein a behavior of the live object of the live event affects the behavior of the virtual object and each participant, wherein the user can select a point of view from a selected participant.

2. The method for using augmented reality of claim 1, wherein: the virtual object is presented such that the virtual object appears to compete with the live object.

3. The method for using augmented reality of claim 1, wherein the live event is a sporting event.

4. The method for using augmented reality of claim 1, further comprising: receiving, by the computerized device, data corresponding to a second virtual object from a remote computerized device; and displaying, by the computerized device, the live event augmented by the virtual object further augmented with the second virtual object.

5. The method for using augmented reality of claim 4, wherein the behavior of the second virtual object is affected by a second user.

6. The method for using augmented reality of claim 4, further comprising: modifying, by the computerized device, behavior of the virtual object in response to the second virtual object.

7. A method for using augmented reality, the method comprising: receiving, by a computerized device, data corresponding to a live event; presenting, by the computerized device, the live event up to a point in time; presenting, by the computerized device, a virtual event at least partially based on an event that occurred during the live event earlier than the point in time; receiving, by the computerized device, input linked with the virtual event, wherein the input is received from a user; and presenting, by the computerized device, an outcome of the virtual event, wherein the outcome is at least partially based on the input received from the user.

8. The method for using augmented reality of claim 7, wherein: the virtual event is presented at least starting when the live event is stopped.

9. The method of claim 7, wherein the live event is a sporting event.

10. The method of claim 7, wherein the live event comprises: soccer, football, basketball, tennis, boxing, car racing, golf, ice hockey, badminton, volleyball, cycling, swimming, snooker, martial arts, rugby, motorbike, hockey, table tennis, horse racing, gymnastics, handball, figure skating, wrestling, skiing, diving, skating, archery, sailing, wrestling, fencing, equestrian, rowing, surfing, Beach Volleyball, Pool/Billiards, Lacrosse, Windsurfing, Polo, Tenpin Bowling, Racquetball, Competitive Climbing, Mountain Biking.

11. A method for using virtual reality, the method comprising: receiving, by a computerized device, a data stream with a 360 degree view of a computer generated event on each participant, wherein the data stream comprises live video, wherein: the live video comprises a live object; receiving, by the computerized device, input from a user, wherein the input from the user affects behavior of a virtual object; and presenting, by the computerized device, the live event augmented by the virtual object, wherein a behavior of the live object of the live event affects the behavior of the virtual object and each participant.

12. A method for using augmented reality and virtual reality, the method comprising: receiving, by a computerized device, a data stream with a 360 degree view of a live event on each participant, wherein the data stream comprises live video, wherein: the live video comprises a live object; receiving, by the computerized device, input from a user, wherein the input from the user affects behavior of a virtual object; and presenting, by the computerized device, the live event augmented by the virtual object, wherein a behavior of the live object of the live event affects the behavior of the virtual object and each participant, and wherein the virtual reality is rendered by switching the display from an augmented view to a virtual reality view by fading out the augmented view on the display to show only the virtual reality view and switching back when augmented reality view is desired.

Moreover, the viewers can collaboratively read the situation and recommend a strategy in real-time to improve viewer participation. In this manner, 1. A method for participating in a game, the method comprising: collecting from viewers of a game one or more state change events during a game; determining whether a series of the collected state change events are a known pattern; requesting, when the series of the collected state change events is an unknown pattern, viewers of the game to identify what caused the collected state change events; and judging, by the viewers, a best reason among the identified causes of the collected state change events.

2. The method of claim 1, comprising running a lottery to decide which recommendation is used for the next play in the game.

3. The method of claim 1, further comprising: compensating at least one viewer who is judged to have the best reason among the identified causes of the collected state change events.

4. The method of claim 1, further comprising: storing as the known pattern, the best reason among the identified causes of the collected state change events when one of the pattern is repeated greater than a threshold number of repeats, and the number of the viewers who agree with the corresponding best reason is greater than a threshold number of users.

5. The method of claim 4, further comprising: associating with the stored best reason a corrective action to be taken in response to a future corresponding the collected state change events.

6. The method of claim 4, further comprising: displaying to the other viewers and players, when the stored best reason is known, the occurrence of the stored best reason.

7. The method of claim 5, further comprising: transmitting the stored best reason to other viewers.

8. The method of claim 1, wherein the series of the collected state change events are at least two state change events that occur within a threshold period of time from each other.

Recognition of Exercise Pattern and Tracking of Calorie Consumption

Figure 16A:
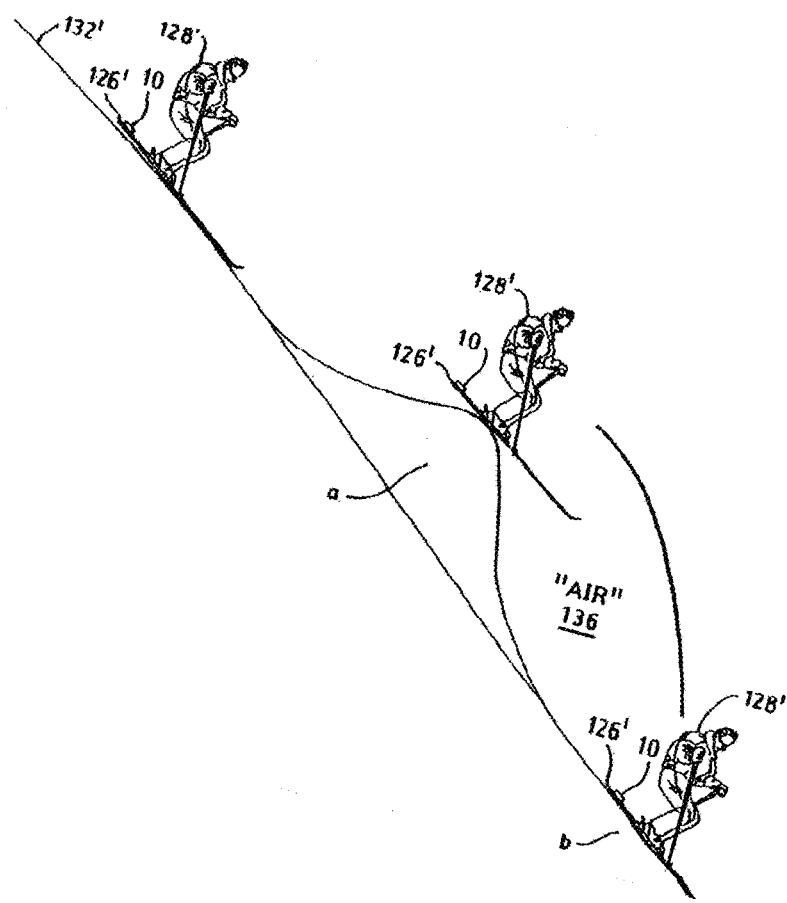

FIG. 16A illustrates the positions of a ski 126' and skier 128' during a lofting maneuver on the slope 132'. The ski 126' and skier 128' speed down the slope 132' and launch into the air 136 at position "a," and later land at position "b" in accord with the well-known Newtonian laws of physics. With an airtime sensor, described above, the unit 10 calculates and stores the total airtime that the ski 126' (and hence the skier 128') experiences between the positions "a" and "b" so that the skier 128' can access and assess the "air" time information. Airtime sensors such as the sensor 14 may be constructed with known components. Preferably, the sensor 14 incorporates either an accelerometer or a microphone. Alternatively, the sensor 14 may be constructed as a mechanical switch that detects the presence and absence of weight onto the switch. Other airtime sensors 14 will become apparent in the description which follows. The accelerometer senses vibration—particularly the vibration of a vehicle such as a ski or mountain bike—moving along a surface, e.g., a ski slope or mountain bike trail. This voltage output provides an acceleration spectrum over time; and information about airtime can be ascertained by performing calculations on that spectrum. Based on the information, the system can reconstruct the movement path, the height, the speed, among others and such movement data is used to identify the exercise pattern. For example, the skier may be interested in practicing mogul runs, and the system can identify foot movement and speed and height information and present the information post exercises as feedback. Alternatively, the system can make live recommendations to improve performance to the athlete.

Figure 16B:
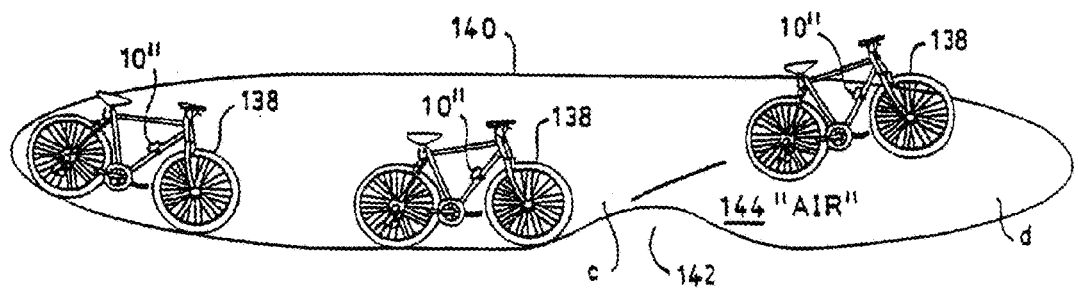
Figure 16C:
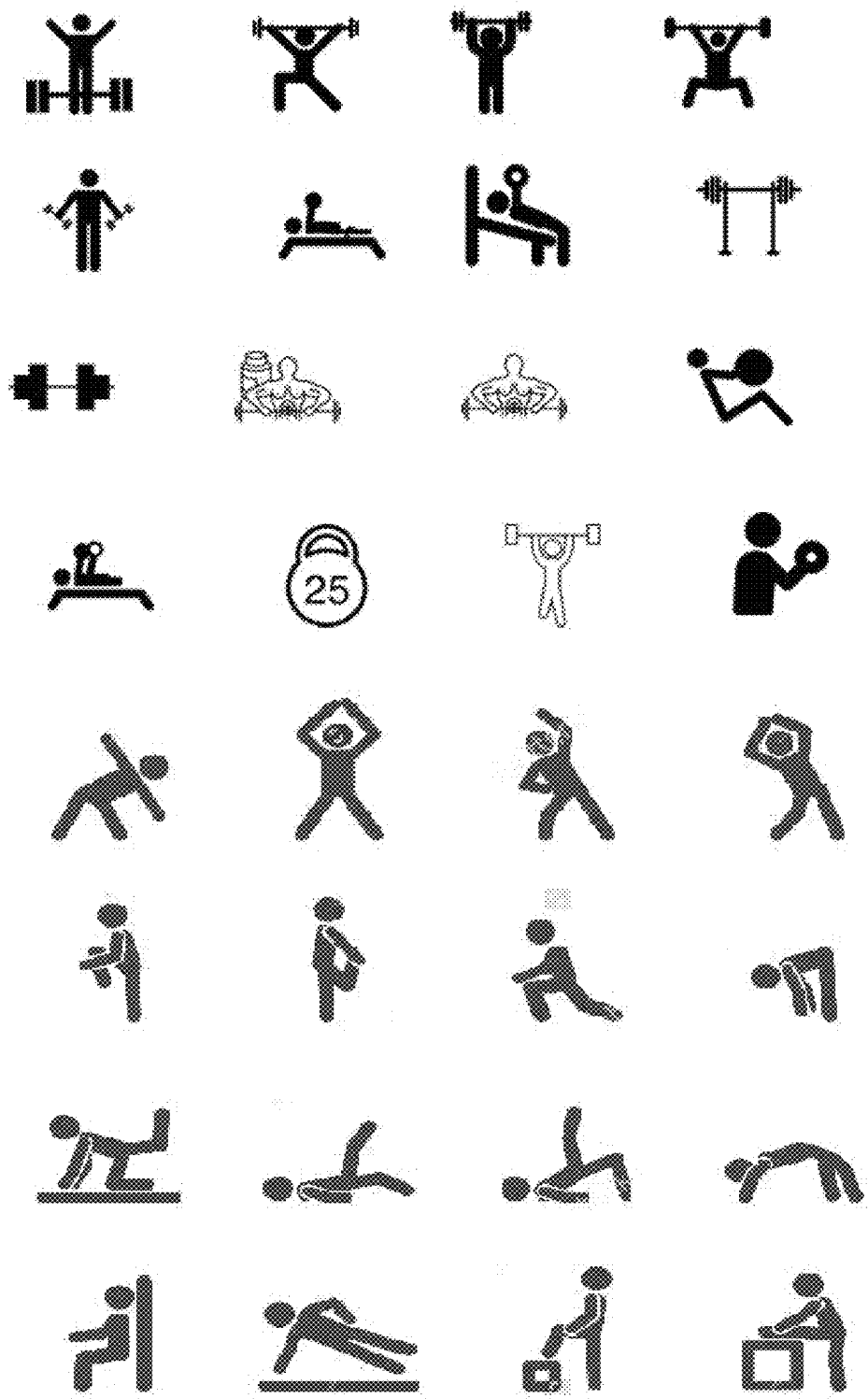

FIG. 16B illustrates a sensing unit 10" mounted onto a mountain bike 138. FIG. 16B also shows the mountain bike 138 in various positions during movement along a mountain bike race course 140 (for illustrative purposes, the bike 138 is shown without a rider). At one location "c" on the race course 140, the bike 138 hits a dirt mound 142 and catapults into the air 144. The bike 138 thereafter lands at location "d". As above, with speed and airtime sensors, the unit 10 provides information to a rider of the bike 138 about the speed attained during the ride around the race course 140; as well as information about the airtime between location "c" and "d". In this case, the system can recommend a cadence to be reached by the rider, strengthen of abdominals, back and arms, for example.

For golf exercise, It is beneficial to require the golfer to swing the golf club a plurality of times at each swing position to account for variations in each swing. The swing position at which the golf club is swung can be determined by analysis of the measured acceleration provided by the accelerometer, e.g., the time at which the acceleration changes. Data obtained during the training stage may be entered into a virtual table of swing positions and estimated carrying distances for a plurality of different swing positions and a plurality of different swings. A sample format for such a table is as follows, and includes the averaged carrying distance for each of four different swing positions. The swing analyzer provides a golfer with an excellent estimation of the carrying distance of a golf ball for a golf club swing at a specific swing position because it has been trained on actual swings by the golfer of the same club and conversion of information about these swings into estimated carrying distances. The golfer can improve their golf game since they can better select a club to use to hit a golf club for different situations during a round of golf. Also, the swing pattern is used to identify each club path responsible for the curve of any shot and this information is used to improve the golfer. The direction of the club path relative to the target, out-to-in (fade pattern) or in-to-out (draw pattern), is what I refer to as a players swing pattern. Players that swing from in-to-out will tend to hit draws and players that swing from out-to-in will tend to hit fades. Where the ball is struck on the face of the driver (strike point) can drastically alter the effect of a players swing pattern on ball flight. Thus, the camera detects where the ball is struck, and a computer physics model of ball behavior is presented to the golfer to improve the score. Shots struck off the heel will tend to fade more or draw less and shots struck off the toe will tend to draw more or fade less. Thus, camera images of the shots struck of heel or toe can also be used to provide pattern recognition/prediction and for training purposes.

For tennis, examples of motions determined for improvement are detailed next. The system can detect if the continental grip is achieved. Throwing Action pattern is also detected, as the tennis serve is an upwards throwing action that would deliver the ball into the air if it were a baseball pitch. Ball Toss improvements can be determined when the player lines the straight arm up with the net post and release the ball when your hand reaches eye level. The system checks the forward direction so the player can drive weight (and built up momentum) forward into the ball and into the direction of the serve.

The sensors can work with a soccer training module with kinematics of ball control, dribbling, passing, crossing, shooting, heading, volleying, taking throw-ins, penalties, corner kicks and free kicks, tackling, marking, juggling, receiving, shielding, clearing, and goalkeeping. The sensors can work with a basketball training module with kinematics of crossover dribble, behind back, pull back dribble, low dribble, basic dribble, between legs dribble, Overhead Pass, Chest Pass, Push Pass, Baseball Pass, Off-the-Dribble Pass, Bounce Pass, Jump Shot, Dunk, Free throw, Layup, Three-Point Shot, Hook Shot. The sensors can work with a baseball training module with kinematics of Hitting, Bunting, Base Running and Stealing, Sliding, Throwing, Fielding Ground Balls, Fielding Fly Balls, Double Plays and Relays, Pitching and Catching, Changing Speeds, Holding Runners, Pitching and Pitcher Fielding Plays, Catching and Catcher Fielding Plays.

Figure 16D:
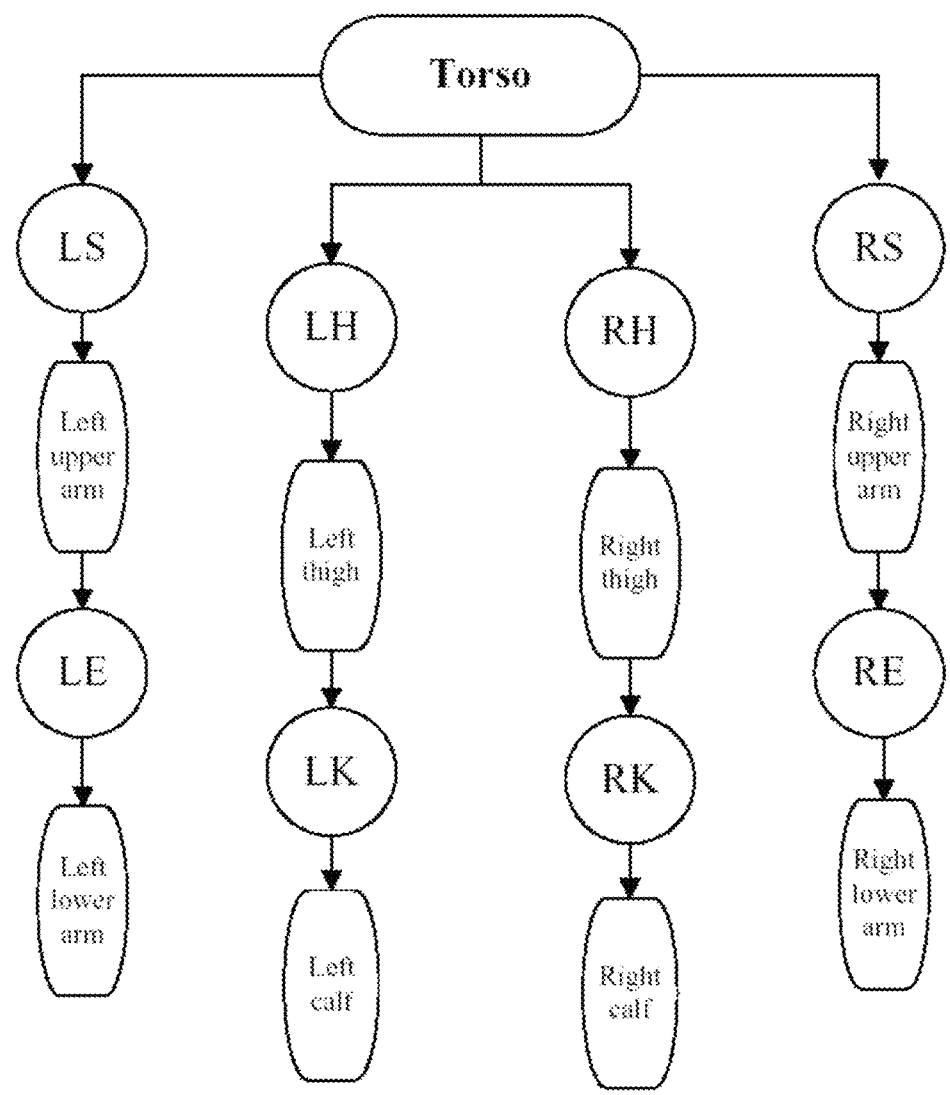
FIG. 16D shows a kinematic modeling for detecting exercise motion which in turn allows precision coaching suggestions.

For weight training, the sensor can be in gloves as detailed above, or can be embedded inside the weight itself, or can be in a smart watch, for example. The user would enter an app indicating that the user is doing weight exercises and the weight is identified as a dumbbell, a curl bar, and a bar bell. Based on the arm or leg motion, the system automatically detects the type of weight exercise being done. In one embodiment shown in FIG. 15C, with motion patterns captured by glove and sock sensors, the system can automatically detect the following exemplary exercise:

Upper Body:
  Chest: Barbell Bench Presses, Barbell Incline Presses, Dumbbell Bench Presses, Dumbbell Incline Presses, Dumbbell Flies, Cable Crossovers
  Back: Pull-Ups, Wide-Grip Lat Pulldowns, One-Arm Dumbbell Rows, Seated Cable Rows, Back Extensions, Straight Arm Pulldowns
  Shoulders: Seated Dumbbell Presses, Front Raises, Lateral Raises, Reverse Flies, Upright Cable Rows, Upright Barbell Rows Biceps: Alternate Dumbbell Curls, Barbell Curls, Preacher Curls, Concentration Curls, Cable Curls, Hammer Curls Triceps: Seated Triceps Presses, Lying Triceps Presses, Triceps Kickbacks, Triceps Pushdowns, Cable Extensions, Bench Dips Lower Body Quadriceps: Barbell Squats, Leg Presses, Leg Extensions Hamstrings: Dumbbell Lunges, Straight-Leg Deadlifts, Lying Leg Curls Calves: Seated Calf Raises, Standing Heel Raises Abs: Floor Crunches, Oblique Floor Crunches, Decline Crunches, Decline Oblique, Hanging Knee Raises, Reverse Crunches, Cable Crunches, Cable Oblique Crunches In one implementation in FIG. 16D, an HMM is used to track weightlifting motor skills or sport enthusiast movement patterns. Human movement involves a periodic motion of the legs. Regular walking involves the coordination of motion at the hip, knee and ankle, which consist of complex joints. The muscular groups attached at various locations along the skeletal structure often have multiple functions. The majority of energy expended during walking is for vertical motion of the body. When a body is in contact with the ground, the downward force due to gravity is reflected back to the body as a reaction to the force. When a person stands still, this ground reaction force is equal to the person's weight multiplied by gravitational acceleration. Forces can act in other directions. For example, when we walk, we also produce friction forces on the ground. When the foot hits the ground at a heel strike, the friction between the heel and the ground causes a friction force in the horizontal plane to act backwards against the foot. This force therefore causes a breaking action on the body and slows it down. Not only do people accelerate and brake while walking, they also climb and dive. Since reaction force is mass times acceleration, any such acceleration of the body will be reflected in a reaction when at least one foot is on the ground. An upwards acceleration will be reflected in an increase in the vertical load recorded, while a downwards acceleration will be reduce the effective body weight. Zigbee wireless sensors with tri-axial accelerometers are mounted to the sport enthusiast on different body locations for recording, for example the tree structure as shown in FIG. 16D. As shown therein, sensors can be placed on the four branches of the links connect to the root node (torso) with the connected joint, left shoulder (LS), right shoulder (RS), left hip (LH), and right hip (RH). Furthermore, the left elbow (LE), right elbow (RE), left knee (LK), and right knee (RK) connect the upper and the lower extremities. The wireless monitoring devices can also be placed on upper back body near the neck, mid back near the waist, and at the front of the right leg near the ankle, among others.

The sequence of human motions can be classified into several groups of similar postures and represented by mathematical models called model-states. A model-state contains the extracted features of body signatures and other associated characteristics of body signatures. Moreover, a posture graph is used to depict the inter-relationships among all the model-states, defined as PG(ND,LK), where ND is a finite set of nodes and LK is a set of directional connections between every two nodes. The directional connection links are called posture links. Each node represents one model-state, and each link indicates a transition between two model-states. In the posture graph, each node may have posture links pointing to itself or the other nodes.

In the pre-processing phase, the system obtains the human body profile and the body signatures to produce feature vectors. In the model construction phase, the system generate a posture graph, examine features from body signatures to construct the model parameters of HMM, and analyze human body contours to generate the model parameters of ASMs. In the motion analysis phase, the system uses features extracted from the body signature sequence and then applies the pre-trained HMM to find the posture transition path, which can be used to recognize the motion type. Then, a motion characteristic curve generation procedure computes the motion parameters and produces the motion characteristic curves. These motion parameters and curves are stored over time, and if differences for the motion parameters and curves over time is detected, the system then runs the sport enthusiast through additional tests to confirm the detected motion.

In one exemplary process for determining exercise in the left or right half of the body, the process compares historical left shoulder (LS) strength against current LS strength (3200). The process also compares historical right shoulder (RS) strength against current RS strength (3202). The process can compare historical left hip (LH) strength against current LH strength (3204). The process can also compare historical right hip (RH) strength against current RH strength (3206). If the variance between historical and current strength exceeds threshold, the process generates warnings (3208). Furthermore, similar comparisons can be made for sensors attached to the left elbow (LE), right elbow (RE), left knee (LK), and right knee (RK) connect the upper and the lower extremities, among others.

The system can ask the sport enthusiast to squeeze a strength gauge, piezoelectric sensor, or force sensor to determine force applied during squeeze. The user holds the sensor or otherwise engages the sensor. The user then applies and holds a force (e.g., compression, torque, etc.) to the sensor, which starts a timer clock and triggers a sampling start indicator to notify the user to continue to apply (maximum) force to the sensor. Strength measurements are then sampled periodically during the sampling period until the expiration of time. From the sampled strength data, certain strength measurement values are selected, such as the maximum value, average value(s), or values obtained during the sampling period. The user can test both hands at the same time, or alternatively he may test one hand at a time. A similar approach is used to sense leg strength, except that the user is asked to pushed down on a scale to determine the foot force generated by the user.

In one embodiment, exercise motion data acquired by the accelerometer or multi-axis force sensor is analyzed, as will be discussed below, in order to determine the motion of each exercise stroke during the exercise session (i.e., horizontal vertical or circular). In another embodiment for detecting exercise motion using accelerometer, the first minimum discovered during the scanning is noted as the first xmin and considered to be the start of the first brushstroke. The first maximum x value following the first minimum x value is located and construed to be the middle of the first exercise stroke (where exercise motion changes from one direction to the other). The next xmin value indicates the end of the first brushstroke and the beginning of the next brushstroke. The computer records the data for each brushstroke and continues on through the data to find the next brushstroke, recording each successive motion in memory. For the first brushstroke, the maximum and minimum values of the x coordinate (xmax and xmin) are determined. The Y-direction lengths, Ly1 and Ly2, between the data points just before and just after each of xmax and xmin (xmax+1, xmax−1, and Xmin+1, xmin−1) are then determined. The length Lx along the x axis, between xmax and xmin, is also determined. Next, if Lx is less than 2 and either Ly1 or Ly2 is greater than one, then the motion is construed to be vertical. If Ly1 and Ly2 are both less than one, then the motion is construed to be horizontal. Otherwise, the motion is construed to be circular.

Data obtained from the gyroscope, if one is used, typically does not require a complex analysis. To determine which side of the mouth is being brushed at a particular time, the gyroscope data is scanned to determine when the rotational orientation is greater than 180 degrees, indicating the left side, and when it is less than 180 degrees, indicating the right side. As explained above, top and bottom and gum brushing information can also be obtained, without any calculations, simply by examining the data. The time sequence of data that is acquired during exercise and analyzed as discussed above can be used in a wide variety of ways.

In one embodiment, the accelerometers distinguish between lying down and each upright position of sitting and standing based on the continuous output of the 3D accelerometer. The system can detect (a) extended time in a single position; (b) extended time sitting in a slouching posture (kyphosis) as opposed to sitting in an erect posture (lordosis); and (c) repetitive stressful movements, such as may be found on some manufacturing lines, while typing for an extended period of time without proper wrist support, or while working all day at a weight lifting exercise, among others. In one alternative embodiment, angular position sensors, one on each side of the hip joint, can be used to distinguish lying down, sitting, and standing positions. In another embodiment, the system repeatedly records position and/or posture data over time. In one embodiment, magnetometers can be attached to a thigh and the torso to provide absolute rotational position about an axis coincident with Earth's gravity vector (compass heading, or yaw). In another embodiment, the rotational position can be determined through the in-door positioning system as discussed above.

To improve a golf swing, the complex motion of the body first starts with the stance. The system checks that the golfer has a low center of gravity to remain balanced throughout the swing path. The swing starts with the arms moving back in a straight line. When the club head reaches the level of the hip, two things happen: there is a stern wrist cock that acts as a hinge along with the left knee (for a right handed swing), building up its torque by moving into the same line as the belly button before the start of the upswing. As the swing continues to the top of the backswing (again for right handed golf swing), the golfer's left arm should be perfectly straight and his right arm should be hinged at the elbow. The downswing begins with the hips and the lower body rather than the arms and upper body, with emphasis on the wrist cock. As the golfer's hips turn into the shot, the right elbow will drop straight down, hugging the right side of the golfer's torso. As the right elbow drops, the wrists begin to snap through from the wrist cock in the backswing. A solid extension of the arms and good transfer of body should put the golfer leaning up on his right toe, balanced, with the golf club resting on the back of the golfers neck. Importantly, all of the movements occur with precise timing, while the head remains completely still with eyes focused on the ball throughout the entire swing.

The system can identify illnesses and prevent overexertion leading to illnesses such as a stroke. Depending on the severity of the stroke, sport enthusiasts can experience a loss of consciousness, cognitive deficits, speech dysfunction, limb weakness, hemiplegia, vertigo, diplopia, lower cranial nerve dysfunction, gaze deviation, ataxia, hemianopia, and aphasia, among others. Four classic syndromes that are characteristically caused by lacunar-type stroke are: pure motor hemiparesis, pure sensory syndrome, ataxic hemiparesis syndrome, and clumsy-hand dysarthria syndrome. Sport enthusiasts with pure motor hemiparesis present with face, arm, and leg weakness. This condition usually affects the extremities equally, but in some cases it affects one extremity more than the other. The most common stroke location in affected sport enthusiasts is the posterior limb of the internal capsule, which carries the descending corticospinal and corticobulbar fibers. Other stroke locations include the pons, midbrain, and medulla. Pure sensory syndrome is characterized by hemibody sensory symptoms that involve the face, arm, leg, and trunk. It is usually the result of an infarct in the thalamus. Ataxic hemiparesis syndrome features a combination of cerebellar and motor symptoms on the same side of the body. The leg is typically more affected than the arm. This syndrome can occur as a result of a stroke in the pons, the internal capsule, or the midbrain, or in the anterior cerebral artery distribution. Sport enthusiasts with clumsy-hand dysarthria syndrome experience unilateral hand weakness and dysarthria. The dysarthria is often severe, whereas the hand involvement is more subtle, and sport enthusiasts may describe their hand movements as "awkward." This syndrome is usually caused by an infarct in the pons. Different patterns of signs can provide clues as to both the location and the mechanism of a particular stroke. The system can detect symptoms suggestive of a brainstem stroke include vertigo, diplopia, bilateral abnormalities, lower cranial nerve dysfunction, gaze deviation (toward the side of weakness), and ataxia. Indications of higher cortical dysfunction-such as neglect, hemianopsia, aphasia, and gaze preference (opposite the side of weakness)—suggest hemispheric dysfunction with involvement of a superficial territory from an atherothrombotic or embolic occlusion of a mainstem vessel or peripheral branch.

To detect muscle weakness or numbness, in one embodiment, the system applies a pattern recognizer such as a neural network or a Hidden Markov Model (HMM) to analyze accelerometer output. In another embodiment, electromyography (EMG) is used to detect muscle weakness. In another embodiment, EMG and a pattern analyzer is used to detect muscle weakness. In yet another embodiment, a pattern analyzer analyzes both accelerometer and EMG data to determine muscle weakness. In a further embodiment, historical ambulatory information (time and place) is used to further detect changes in muscle strength. In yet other embodiments, accelerometer data is used to confirm that the sport enthusiast is at rest so that EMG data can be accurately captured or to compensate for motion artifacts in the EMG data in accordance with a linear or non-linear compensation table. In yet another embodiment, the EMG data is used to detect muscle fatigue and to generate a warning to the sport enthusiast to get to a resting place or a notification to a nurse or caregiver to render timely assistance. The amplitude of the EMG signal is stochastic (random) in nature and can be reasonably represented by a Gaussian distribution function. The amplitude of the signal can range from 0 to 10 mV (peak-to-peak) or 0 to 1.5 mV (rms). The usable energy of the signal is limited to the 0 to 500 Hz frequency range, with the dominant energy being in the 50-150 Hz range. Usable signals are those with energy above the electrical noise level. The dominant concern for the ambient noise arises from the 60 Hz (or 50 Hz) radiation from power sources. The ambient noise signal may have an amplitude that is one to three orders of magnitude greater than the EMG signal. There are two main sources of motion artifact: one from the interface between the detection surface of the electrode and the skin, the other from movement of the cable connecting the electrode to the amplifier. The electrical signals of both noise sources have most of their energy in the frequency range from 0 to 20 Hz and can be reduced.

In one embodiment, the camera captures facial expression and a code such as the Microsoft Emotion API takes a facial expression in an image as an input, and returns the confidence across a set of emotions for each face in the image, as well as bounding box for the face, using the Face API. The emotions detected are anger, contempt, disgust, fear, happiness, neutral, sadness, and surprise. These emotions are understood to be cross-culturally and universally communicated with particular facial expressions. Alternatively, a marker for emotional arousal is galvanic skin response (GSR), also referred to as skin conductance (SC) or electrodermal activity (EDA). EDA modulates the amount of sweat secretion from sweat glands. The amount of sweat glands varies across the human body, being highest in hand and foot regions (200-600 sweat glands per cm2). While sweat secretion plays a major role for thermoregulation and sensory discrimination, changes in skin conductance in hand and foot regions are also triggered quite impressively by emotional stimulation: the higher the arousal, the higher the skin conductance. It is noteworthy to mention that both positive ("happy" or "joyful") and negative ("threatening" or "saddening") stimuli can result in an increase in arousal—and in an increase in skin conductance. Skin conductance is not under conscious control. Instead, it is modulated autonomously by sympathetic activity which drives human behavior, cognitive and emotional states on a subconscious level. Skin conductance therefore offers direct insights into autonomous emotional regulation. It can be used as alternative to self-reflective test procedures, or—even better—as additional source of insight to validate verbal self-reports or interviews of a respondent. Based on the detected emotion, the exercise can be increased, decreased, or stopped altogether.

Features of the auto-detection of exercise include the following:

1. An exercise system, comprising:
   a processor running the motion analyzer and coupled to a wireless transceiver;
   an accelerometer coupled to the processor; and
   a kinematic motion analysis module executed by the processor to detect exercise type.
2. The system of claim 1, comprising a plurality of smart modules mounted on an exerciser forming a mesh network.
3. The system of claim 1 where the electronic components, sensors, and interconnects of the system monitor, record, process and/or transmit events of interest (such as accelerometers and gyroscopes for impact events, temperature sensors for temperature and/or temperature gradients, pressure sensors, moisture sensors, chemical sensors).
4. The system of claim 1 comprised for sensing and/or monitoring impact events where the sensors are accelerometers, gyroscopes, and/or pressure sensors.
5. The system of claim 1 comprised for sensing and/or monitoring and/or controlling ongoing events where the sensors monitor temperature, temperature gradients, motion, position, environmental or chemical levels, or other such information.
6. The system of claim 1 comprised for sensing events or other information including mounting multiple distributed sensors for obtaining spatial and/or temporal distribution in the data and/or multiple sensors sensing different information and data.
7. The system of claim 1 comprising a camera and an image recognition module to determine kinematic movement.
8. The system of claim 1 including a statistical recognizer to determine kinematic movement.
9. The system of claim 8, comprising a model-state that contains the extracted features of body signatures and other associated characteristics of body signatures.
10. The system of claim 1 comprising links connecting a root node (torso) with connected joint, left shoulder (LS), right shoulder (RS), left hip (LH), and right hip (RH), and left elbow (LE), right elbow (RE), left knee (LK), and right knee (RK) connect upper and lower extremities.
11. The system of claim 1 comprising a posture detection module.
12. The system of claim 1, comprising a module to detect a lying down state and a standing state.
13. The system of claim 1, comprising a hidden markov model module to detect muscle movement and exercise pattern.
14. The system of claim 1 comprising optimizing tennis shots to improve serve, groundstroke, volley, half volley, smash, forehand, backhand, flat, side spin, block, slice, topspin shot, lob, passing shot, dropshot, cross-court shot, down-the-line shot.
15. The system of claim 1, comprising an electromyography (EMG) sensor to detect muscle strength or weakness.
16. The system of claim 1, comprising an emotion detector wherein an exercise can be increased, decreased, or stopped based on detected emotion.
17. The system of claim 17, wherein the detector comprises video detection of faces or a GSR sensor.
18. The system of claim 1 comprising a cloud storage to receive sensor data.
19. The system of claim 1, comprising a golf training module that checks that a golfer has a low center of gravity to remain balanced throughout a swing path, that a swing starts with the arms moving back in a straight line, and when a club head reaches the level of the hip, a wrist cock acts as a hinge along with the left knee (for a right handed swing), building up torque by moving into the same line as the belly button before the start of the upswing. As the swing continues to the top of the backswing (again for right handed golf swing), the golfer's left arm is straight and a right arm is hinged at the elbow.
20. The system of claim 19, wherein the golf training module checks that a downswing begins with the hips and the lower body and as the golfer's hips turn into the shot, the right elbow drops down, hugging the right side of the golfer's torso and wrists begin to snap through from the wrist cock in the backswing.
21. The system of claim 1, comprising a soccer training module with kinematics of ball control, dribbling, passing, crossing, shooting, heading, volleying, taking throw-ins, penalties, corner kicks and free kicks, tackling, marking, juggling, receiving, shielding, clearing, and goalkeeping.
22. The system of claim 1, comprising a basketball training module with kinematics of crossover dribble, behind back, pull back dribble, low dribble, basic dribble, between legs dribble, Overhead Pass, Chest Pass, Push Pass, Baseball Pass, Off-the-Dribble Pass, Bounce Pass, Jump Shot, Dunk, Free throw, Layup, Three-Point Shot, Hook Shot.

23. The system of claim 1, comprising a baseball training module with kinematics of Hitting, Bunting, Base Running and Stealing, Sliding, Throwing, Fielding Ground Balls, Fielding Fly Balls, Double Plays and Relays, Pitching and Catching, Changing Speeds, Holding Runners, Pitching and Pitcher Fielding Plays, Catching and Catcher Fielding Plays.

Data from multiple exercise sessions may be collected and used to compile a history of the user's habits over an extended period of time, enabling the user's trainer to better understand user compliance issues. The trainer can review the data with the user and view the animations of the user's exercise sessions during an office visit, allowing the trainer to better instruct the user in proper brushing technique. The trainer can also review the patient's brushing history over time, to determine whether the patient's exercise technique is improving.

The sensor 14 can be integrated into objects already associated with the sporting activity. In one aspect, the sensing unit is integrated into the ski boot or other boot. In another aspect, the sensing unit is integrated into the binding for a ski boot or snowboarder boot. In still another aspect, the sensing unit is integrated into a ski, snowboard, mountain bike, windsurfer, windsurfer mast, roller blade boot, skate-board, kayak, or other sport vehicle. Collectively, the sport objects such as the ski boot and the variety of sport vehicles are denoted as "sport implements". Accordingly, when the sensing unit is not "stand alone", the housing which integrates the controller subsystem with one or more sensors and battery can be made from the material of the associated sport implement, in whole or in part, such that the sensing unit becomes integral with the sport implement. The universal interface is therefore not desired in this aspect.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The embodiments described herein may include the use of a special purpose or general-purpose computer including various computer hardware or software modules, as discussed in greater detail below.

Embodiments described herein may be implemented using computer-readable media for carrying or having computer-executable instructions or data structures stored thereon. Such computer-readable media may be any available media that may be accessed by a general purpose or special purpose computer. By way of example, and not limitation, such computer-readable media may include tangible computer-readable storage media including RAM, ROM, EEPROM, CD-ROM or other optical disk storage, magnetic disk storage or other magnetic storage devices, or any other storage medium which may be used to carry or store desired program code in the form of computer-executable instructions or data structures and which may be accessed by a general purpose or special purpose computer. Combinations of the above may also be included within the scope of computer-readable media. Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. As used herein, the term "module" or "component" may refer to software objects or routines that execute on the computing system. The different components, modules, engines, and services described herein may be implemented as objects or processes that execute on the computing system (e.g., as separate threads). While the system and methods described herein may be preferably implemented in software, implementations in hardware or a combination of software and hardware are also possible and contemplated. In this description, a "computing entity" may be any computing system as previously defined herein, or any module or combination of modulates running on a computing system. All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

What is claimed is:

1. An implement, comprising: an elongated body;
   a processor in the elongated body and coupled to a wireless transceiver;
   a camera coupled to the elongated body to determine a distance, shape, or dimension of an object proximal to the elongated body; and
   an accelerometer disposed within the elongated body to detect acceleration of the implement: and a module to record the motion of the implement using the camera and the accelerometer to compare with a proper motion suggestion by a third party to improve user action.

2. The implement of claim 1, wherein at least one sensor selected from a sensor set comprising: a pressure sensor configured to detect at least one pressure event at an external surface location; a motion sensor configured to detect at least one motion event of the implement; a digit motion sensor configured to detect at least one motion event of at least one digit of the user; a temperature sensor configured to detect a temperature at an external surface location.

3. The implement of claim 1, wherein the elongated body comprises a tooth brush, comprising one or more of: processor code to determine which side of a mouth is being brushed, processor code to determine a brushing time, processor code to determine a brush rotational orientation in the mouth, processor code to determine brushing on a predetermined mouth side, processor code to determine brushing on a top or a bottom, processor code to determine gum brushing.

4. The implement of claim 1, comprising a hand exercise regimen selected from a hand exercise regimen set comprising at least one of: a physical therapy hand exercise regimen; a physical training hand exercise regimen; or a physical performance hand exercise regimen.

5. The implement of claim 1, comprising a gesture identifying component configured to identify at least one hand gesture detected by at least one sensor; the memory configured to, upon receiving an indication of a hand gesture identified by the gesture identifying component, store data corresponding to the hand gesture in the memory; and the device interface configured to, upon connecting to the device, provide at least some of the stored data corresponding to the hand gesture to the device.

6. The implement of claim 1, comprising a plurality of finger receptacles, each having a sensor.

7. The implement of claim 1, comprising a sensor worn by an opponent in wireless communication with the processor to communicate the force of an impact from the implement.

8. The implement of claim 1, wherein the implement body comprises a racket body, a golf body, a brush body, or sword body.

9. The implement of claim 1, comprising a hidden markov model module to detect muscle movement and exercise pattern.

10. The implement of claim 1, comprising an emotion detector wherein an exercise can be increased, decreased, or stopped based on detected emotion.

11. A system with an elongated implement, comprising:
an accelerometer disposed in the implement for measuring a force on the implement;
a radio frequency transmitter disposed in the implement and coupled to the accelerometer for transmitting measurements;
a camera in the implement to determine a distance, shape, or dimension of an object near the implement;
a radio frequency receiver for receiving the measurements; and
a module to compare a third party motion with a user motion to improve user motion.

12. The system of claim 11, wherein at least one sensor selected from a sensor set comprising: a pressure sensor configured to detect at least one pressure event at a implement body external surface location; a implement motion sensor configured to detect at least one motion event of the implement; a digit motion sensor configured to detect at least one motion event of at least one digit of the user; a temperature sensor configured to detect a temperature at an external surface location.

13. The system of claim 11, wherein the elongated body comprises a tooth brush, comprising one or more of: processor code to determine which side of a mouth is being brushed, processor code to determine a brushing time, processor code to determine a brush rotational orientation in the mouth, processor code to determine brushing on a predetermined mouth side, processor code to determine brushing on a top or a bottom, processor code to determine gum brushing.

14. The system of claim 11, comprising a hand exercise regimen selected from a hand exercise regimen set comprising at least one of: a physical therapy hand exercise regimen; a physical training hand exercise regimen; or a physical performance hand exercise regimen.

15. The system of claim 11, wherein the implement comprising a gesture identifying component configured to identify at least one hand gesture detected by at least one sensor; the memory configured to, upon receiving an indication of a hand gesture identified by the gesture identifying component, store data corresponding to the hand gesture in the memory; and the device interface configured to, upon connecting to the device, provide at least some of the stored data corresponding to the hand gesture to the device.

16. The system of claim 11, wherein, the implement comprising a plurality of finger receptacles, each having a sensor.

17. The system of claim 11, comprising a sensor worn by an opponent in wireless communication with the processor to communicate the force of an impact from the implement.

18. The system of claim 11, wherein the implement body comprises a racket body, a golf body, or a sword body.

19. The system of claim 11, comprising a hidden markov model module to detect muscle movement and exercise pattern.

20. The system of claim 11, comprising an emotion detector wherein an exercise can be increased, decreased, or stopped based on detected emotion.

* * * * *